US012698285B2

(12) United States Patent
Wu et al.

(10) Patent No.: US 12,698,285 B2
(45) Date of Patent: Aug. 4, 2026

(54) RING-IN-RING COMPLEXES EXHIBITING TUNABLE MULTICOLOR PHOTOLUMINESCENCE

(71) Applicant: Northwestern University, Evanston, IL (US)

(72) Inventors: Huang Wu, Evanston, IL (US); James Fraser Stoddart, Evanston, IL (US); Yu Wang, Evanston, IL (US)

(73) Assignee: Northwestern University, Evanston, IL (US)

( * ) Notice: Subject to any disclaimer, the term of this patent is extended or adjusted under 35 U.S.C. 154(b) by 683 days.

(21) Appl. No.: 18/043,214

(22) PCT Filed: Aug. 25, 2021

(86) PCT No.: PCT/US2021/071284

§ 371 (c)(1),
(2) Date: Feb. 27, 2023

(87) PCT Pub. No.: WO2022/047481

PCT Pub. Date: Mar. 3, 2022

(65) Prior Publication Data

US 2023/0322781 A1 Oct. 12, 2023

Related U.S. Application Data

(60) Provisional application No. 63/070,113, filed on Aug. 25, 2020.

(51) Int. Cl.
*C07D 471/22* (2006.01)
*C09K 11/06* (2006.01)

(52) U.S. Cl.
CPC ............ *C07D 471/22* (2013.01); *C09K 11/06* (2013.01); *C09K 2211/1022* (2013.01)

(58) Field of Classification Search
CPC .. C07D 471/22; C09K 11/06; C09K 11/1022; C09K 2211/1022
See application file for complete search history.

(56) References Cited

U.S. PATENT DOCUMENTS

2014/0179017 A1 6/2014 Stoddart
2019/0382655 A1 12/2019 Kuwana et al.

FOREIGN PATENT DOCUMENTS

WO 2020160382 A1 8/2020

OTHER PUBLICATIONS

Cai et al., "Molecular Russian Dolls". Nat. Commun. 2018, 9, 5275. (Year: 2018) provided in IDS.*

Weigend, F. Accurate Coulomb-Fitting Basis Sets for H to Rn. Phys. Chem. Chem. Phys. 2006, 8, 1057-1065.

Weigend, F.; Ahlrichs, R. Balanced Basis Sets of Split Valence, Triple Zeta Valence and Quadruple Zeta Valence Quality for H to Rn: Design and Assessment of Accuracy. Phys. Chem. Chem. Phys. 2005, 7, 3297-3305.

Wu, G.; Bae, Y. J.; Olesińska, M.; Antón-García, D .; Szabó, I.; Rosta, E.; Wasielewski, M. R.; Scherman, O. A. Controlling the Structure and Photophysics of Fluorophore Dimers Using Multiple Cucurbit[8]uril Clampings. Chem. Sci. 2020, 11, 812-825.

Wu, G.; Szabo, I.; Rosta, E.; Scherman, O. A. Cucurbit[8]uril-Mediated Pseudo[2,3]rotaxanes. Chem. Commun. 2019, 55, 13227-13230.

Wu, H.; Chen, Y.; Dai, X.; Li, P.; Stoddart, J. F.; Liu, Y. In Situ Photoconversion of Multicolor Luminescence and Pure White Light Emission Based on Carbon Dot-Supported Supramolecular Assembly. J. Am. Chem. Soc. 2019, 141, 6583-6591.

Wu, H.; Chen, Y.; Liu, Y. Reversibly Photoswitchable Supramolecular Assembly and Its Application as a Photoerasable Fluorescent Ink. Adv. Mater. 2017, 29, 1605271.

Wu, H.; Chen, Y.; Zhang, L.; Anamimoghadam, O.; Shen, D.; Liu, Z.; Cai, K.; Pezzato, C.; Stern, C. L.; Liu, Y.; Stoddart, J. F. A Dynamic Tetracationic Macrocycle Exhibiting Photoswitchable Molecular Encapsulation. J. Am. Chem. Soc. 2019, 141, 1280-1289.

Xia, D.; Wang, P.; Ji, X.; Khashab, N. M.; Sessler, J. L.; Huang, F. Functional Supramolecular Polymeric Networks: The Marriage of Covalent Polymers and Macrocycle-Based Host-Guest Interactions. Chem. Rev. 2020, 120, 6070-6123.

Yang, H.; Ma, Z.; Yuan, B.; Wang, Z.; Zhang, X. Supramolecular Polymerization at the Interface: Layer-by-Layer Assembly Driven by Host-Enhanced TT-TT Interaction. Chem. Commun. 2014, 50, 11173-11176.

Yang, X.; Wang, R.; Kermagoret, A.; Bardelang, D. Oligomeric Cucurbituril Complexes: From Peculiar Assemblies to Emerging Applications. Angew. Chem. Int. Ed. 2020, DOI: 10.1002/anie.202004622.

Zhang, D.; Ronson, T. K.; Greenfield, J. L.; Brotin, T.; Berthault, P.; Leonce, E.; Zhu, J. L.; Xu, L.; Nitschke, J. R. Enantiopure [Cs+/Xe • Cryptophane]• FeII4L4 Hierarchical Superstructures. J. Am. Chem. Soc. 2019, 141, 8339-8345.

Zhang, K. D.; Tian, J.; Hanifi, D.; Zhang, Y.; Sue, A. C.; Zhou, T. Y.; Zhang, L.; Zhao, X.; Liu, Y.; Li, Z. T. Toward a Single-Layer Two-Dimensional Honeycomb Supramolecular Organic Framework in Water. J. Am. Chem. Soc. 2013, 135, 17913-17918.

Zhang, Q. W.; Li, D.; Li, X.; White, P. B.; Mecinovic, J.; Ma, X.; Agren, H.; Nolte, R. J. M.; Tian, H. Multicolor Photoluminescence Including White-Light Emission by a Single Host-Guest Complex. J. Am. Chem. Soc. 2016, 138, 13541-13550.

Zhiquan, L.; Polen, S.; Hadad, C. M.; RajanBabu, T. V.; Badjić, J. D. Russian Nesting Doll Complexes of Molecular Baskets and Zinc Containing TPA Ligands. J. Am. Chem. Soc. 2016, 138, 8253-8258.

Zhou, Z.; Chen, D. G.; Saha, M. L.; Wang, H.; Li, X.; Chou, P. T.; Stang, P. J. Designed Conformation and Fluorescence Properties of Self-Assembled Phenazine-Cored Platinum(II) Metallacycles. J. Am. Chem. Soc. 2019, 141, 5535-5543.

(Continued)

*Primary Examiner* — Matthew E. Hoban
*Assistant Examiner* — Lynne Edmondson
(74) *Attorney, Agent, or Firm* — Quarles & Brady LLP

(57) ABSTRACT

Disclosed herein are ring-in-ring photoluminescent complexes comprising a host cyclophane and a guest cyclophane threaded through the host cyclophane and methods of using and making the same. Further disclosed herein a method for tuning photo-luminescence, the method comprising providing a host cyclophane and a guest cyclophane, contacting the guest cyclophane with the host cyclophane thereby forming the ring-in-ring photoluminescent complex.

19 Claims, 36 Drawing Sheets

(56) References Cited

OTHER PUBLICATIONS

Zhu, K.; Baggi, G.; Loeb, S. J. Ring-through-Ring Molecular Shuttling in a Saturated [3]Rotaxane. Nat. Chem. 2018, 10, 625-630.
Zhu, L.; Li, X.; Zhang, Q.; Ma, X.; Li, M.; Zhang, H.; Luo, Z.; Agren, H.; Zhao, Y. Unimolecular Photoconversion of Multicolor Luminescence on Hierarchical Self-Assemblies. J. Am. Chem. Soc. 2013, 135, 5175-5182.
International Search Report, corresponding to PCT/US2021/071284, dated Dec. 23, 2021.
Pedersen, C. J. Cyclic Polyethers and Their Complexes with Metal Salts. J. Am. Chem. Soc. 1967, 89, 7017-7036.
Amabilino, D. B.; Ashton, P. R.; Boyd, S. E.; Lee, J. Y.; Menzer, S.; Stoddart, J. F.; Williams, D. J. The Five-Stage Self-Assembly of a Branched Heptacatenane. Angew. Chem., Int. Ed. Engl. 1997, 36, 2070-2072.
Ashton, P. R.; Brown, C. L.; Chrystal, E. J. T.; Goodnow, T. T.; Kaifer, A. E.; Parry, K. P.; Philp, D.; Slawin, A. M. Z.; Spencer, N.; Stoddart, J. F.; Williams, D. J. The Self-Assembly of a Highly Ordered [2]Catenane. J. Chem. Soc., Chem. Commun. 1991, 634-639.
Ashton, P. R.; Odell, B.; Reddington, M. V.; Slawin, A. M. Z.; Stoddart, J. F.; Williams, D. J. Isostructural, Alternately- Charged Receptor Stacks. The Inclusion Complexes of Hydroquinone and Catechol Dimethyl Ethers with Cyclobis (paraquat-p-phenylene). Angew. Chem., Int. Ed. Engl. 1988, 27, 1550-1553.
Barone, V.; Cossi, M. Quantum Calculation of Molecular Energies and Energy Gradients in Solution by a Conductor Solvent Model. J. Phys. Chem. A, 1998, 102, 1995-2001.
Barrow, S. J.; Kasera, S.; Rowland, M. J.; del Barrio, J.; Scherman, O. A. Cucurbituril-Based Molecular Recognition. Chem. Rev. 2015, 115, 12320-12406.
Becke, A. D. Density Functional Thermochemistry. III. The Role of Exact Exchange. J. Chem. Phys. 1993, 98, 5648-5652.
Biedermann, F.; Rauwald, U.; Cziferszky, M.; Williams, K. A.; Gann, L. D.; Guo, B. Y.; Urbach, A. R.; Bielawski, C. W.; Scherman, O. A. Benzobis(imidazolium)-Cucurbit[8]uril Complexes for Binding and Sensing Aromatic Compounds in Aqueous Solution. Chem. Eur. J. 2010, 16, 13716-13722.
Bush, M. E.; Bouley, N. D.; Urbach, A. R. Charge-Mediated Recognition of N-Terminal Tryptophan in Aqueous Solution by a Synthetic Host. J. Am. Chem. Soc. 2005, 127, 14511-14517.
Cai, K.; Lipke, M. C.; Liu, Z.; Nelson, J.; Cheng, T.; Shi, Y.; Cheng, C.; Shen, D.; Han, J. M.; Vemuri, S.; Feng, Y.; Stern, C. L.; Goddard, W. A., III; Wasielewski, M. R.; Stoddart, J. F. Molecular Russian Dolls. Nat. Commun. 2018, 9, 5275.
Carvalho, C. P.; Dominguez, Z.; Da Silva, J. P.; Pischel, U. A Supramolecular Keypad Lock. Chem. Commun. 2015, 51, 2698-2701.
Chang, X.; Zhou, Z.; Shang, C.; Wang, G.; Wang, Z.; Qi, Y.; Li, Z. Y.; Wang, H.; Cao, L.; Li, X.; Fang, Y.; Stang, P. J. Coordination-Driven Self-Assembled Metallacycles Incorporating Pyrene: Fluorescence Mutability, Tunability, and Aromatic Amine Sensing. J. Am. Chem. Soc. 2019, 141, 1757-1765.
Chen, W.; Guo, C.; He, Q.; Chi, X.; Lynch, V. M.; Zhang, Z.; Su, J.; Tian, H.; Sessler, J. L. Molecular Cursor Caliper: A Fluorescent Sensor for Dicarboxylate Dianions. J. Am. Chem. Soc. 2019, 141, 14798-14806.
Chiu, S.-H.; Pease, A. R.; Stoddart, J. F.; White, A. J. P.; Williams, D. J. A Ring-in-Ring Complex. Angew. Chem. Int. Ed. 2002, 41, 270-274.
Cram, D. J. The Design of Molecular Hosts, Guests, and Their Complexes (Nobel Lecture). Angew. Chem., Int. Ed. Engl. 1988, 27, 1009-1020.
Cram, D. J.; Cram, J. M. Host-Guest Chemistry: Complexes between Organic Compounds Simulate the Substrate Selectivity of Enzymes. Science 1974, 183, 803-809.
Dale, E. J.; Vermeulen, N. A.; Juríek, M.; Barnes, J. C.; Young, R. M.; Wasielewski, M. R.; Stoddart, J. F. Supramolecular Explorations: Exhibiting the Extent of Extended Cationic Cyclophanes. Acc. Chem. Res. 2016, 49, 262-273.
Dale, E. J.; Vermeulen, N. A.; Thomas, A. A.; Barnes, J. C.; Juríek, M.; Blackburn, A. K.; Strutt, N. L.; Sarjeant, A. A.; Stern, C. L.; Denmark, S. E.; Stoddart, J. F. Excage. J. Am. Chem. Soc. 2014, 136, 10669-10682.
Dalgarno, S. J.; Atwood, J. L.; Raston, C. L. Sulfonatocalixarenes: Molecular Capsule and 'Russian Doll' Arrays to Structures Mimicking Viral Geometry. Chem. Commun. 2006, 4567-4574.
Das, D.; Assaf, K. I.; Nau, W. M. Applications of Cucurbiturils in Medicinal Chemistry and Chemical Biology. Front. Chem. 2019, 7, 619.
Day, A. I.; Blanch, R. J.; Arnold, A. P.; Lorenzo, S.; Lewis, G. R.; Dance, I. A Cucurbituril-Based Gyroscane: A New Supramolecular Form. Angew. Chem. Int. Ed. 2002, 41, 275-277.
Dhara, A.; Flood, A. H. Cages Driven Away from Equilibrium Binding by Electric Fields. Chem 2019, 5, 1017-1019.
Dolomanov, O. V.; Bourhis, L. J.; Gildea, R. J.; Howard, J. A. K.; Puschmann, H. OLEX2: A Complete Structure Solution, Refinement and Analysis Program. J. Appl. Cryst. 2009, 42, 339-341.
Dumartin, M.; Lipke, M. C.; Stoddart, J. F. A Redox-Switchable Molecular Zipper. J. Am. Chem. Soc. 2019, 141, 18308-18317.
Fang, L.; Olson, M. A.; Benitez, D.; Tkatchouk, E.; Goddard, W. A., III; Stoddart, J. F. Mechanically Bonded Macromolecules. Chem. Soc. Rev. 2010, 39, 17-29.
Forgan, R. S.; Sauvage, J.-P.; Stoddart, J. F. Chemical Topology: Complex Molecular Knots, Links, and Entanglements. Chem. Rev. 2011, 111, 5434-5464.
Forgan, R. S.; Spruell, J. M.; Olsen, J.- C.; Stern, C., L.; Stoddart, J. F. Towards the Stepwise Assembly of Molecular Borromean Rings. A Donor-Acceptor Ring-in-Ring Complex. J. Mex. Chem. Soc. 2009, 53, 134-138.
Forgan, R. S.; Wang, C.; Friedman, D. C.; Spruell, J. M.; Stern, C. L.; Sarjeant, A. A.; Cao, D.; Stoddart, J. F. Donor-Acceptor Ring-in-Ring Complexes. Chem. Eur. J. 2012, 18, 202-212.
Freeman, W. A.; Mock, W. L.; Shih, N. Y. Cucurbituril. J. Am. Chem. Soc. 1981, 103, 7367-7368.
Gong, W.; Yang, X.; Zavalij, P. Y.; Isaacs, L.; Zhao, Z.; Liu, S. From Packed "Sandwich" to "Russian Doll": Assembly by Charge-Transfer Interactions in Cucurbit[10]uril. Chem. Eur. J. 2016, 22, 17612-17618.
Gu, L.; Shi, H.; Bian, L.; Gu, M.; Ling, K.; Wang, X.; Ma, H.; Cai, S.; Ning, W.; Fu, L.; Wang, H.; Wang, S.; Gao, Y.; Yao, W.; Huo, F.; Tao, Y.; An, Z.; Liu, X.; Huang, W. Colour-Tunable Ultra-Long Organic Phosphorescence of a Single-Component Molecular Crystal. Nat. Photonics. 2019, 13, 406-411.
Hanwell, M. D.; Curtis, D. E.; Lonie, D. C.; Vandermeersch, T.; Zurek, E.; Hutchison, G. R. Avogadro: An Advanced Semantic Chemical Editor, Visualization, and Analysis Platform. J. Cheminf. 2012, 4, 17.
Harada, A.; Takashima, Y.; Yamaguchi, H. Cyclodextrin-Based Supramolecular Polymers. Chem. Soc. Rev. 2009, 38, 875-882.
Hua, Y.; Flood, A. H. Click Chemistry Generates Privileged CH Hydrogen-Bonding Triazoles: The Latest Addition to Anion Supramolecular Chemistry. Chem. Soc. Rev. 2010, 39, 1262-1271.
Huang, Z.; Yang, L.; Liu, Y.; Wang, Z.; Scherman, O. A.; Zhang, X. Supramolecular Polymerization Promoted and Controlled through Self-Sorting. Angew. Chem. Int. Ed. 2014, 53, 5351-5355.
Ihde, J. Le Châtelier and Chemical Equilibrium. J. Chem. Educ. 1989, 66, 238.
Ikeda, A.; Shinkai, S. Novel Cavity Design Using Calix[n]arene Skeletons: Toward Molecular Recognition and Metal Binding. Chem. Rev. 1997, 97, 1713-1734.
Isaacs, L. Stimuli Responsive Systems Constructed Using Cucurbit[n]uril-Type Molecular Containers. Acc. Chem. Res. 2014, 47, 2052-2062.
Iwanaga, T.; Nakamoto, R.; Yasutake, M.; Takemura, H.; Sako, K.; Shinmyozu, T. Cyclophanes within Cyclophanes: The Synthesis of a Pyromellitic Diimide-Based Macrocycle as a Structural Unit in a Molecular Tube and Its Inclusion Phenomena. Angew. Chem. Int. Ed. 2006, 45, 3643-3647.
Izsák, R.; Neese, F. An Overlap Fitted Chain of Spheres Exchange Method, J. Chem. Phys., 2011, 135, 144105.

(56) References Cited

OTHER PUBLICATIONS

Jeon, W. S.; Kim, H. J.; Lee, C.; Kim, K. Control of the Stoichiometry in Host-Guest Complexation by Redox Chemistry of Guests: Inclusion of Methylviologen in Cucurbit[8]uril. Chem. Commun. 2002, 1828-1829.
Ji, X.; Chi, X.; Ahmed, M.; Long, L.; Sessler, J. L. Soft Materials Constructed Using Calix[4]pyrrole- and "Texas-Sized" Box-Based Anion Receptors. Acc. Chem. Res. 2019, 52, 1915-1927.
Kim, E.; Lee, Y.; Lee, S.; Park, S. B. Discovery, Understanding, and Bioapplication of Organic Fluorophore: A Case Study with an Indolizine-Based Novel Fluorophore, Seoul-Fluor. Acc. Chem. Res. 2015, 48, 538-547.
Kim, H. J.; Jeon, W. S.; Ko, Y. H.; Kim, K. Inclusion of Methylviologen in Cucurbit[7]uril. Proc. Natl. Acad. Sci. U. S. A. 2002, 99, 5007-5011.
Kim, H.-J.; Heo, J.; Jeon, W. S.; Lee, E.; Kim, J.; Sakamoto, S.; Yamaguchi, K.; Kim, K. Selective Inclusion of a Hetero-Guest Pair in a Molecular Host: Formation of Stable Charge-Transfer Complexes in Cucurbit[8]uril. Angew. Chem. Int. Ed. 2001, 40, 1526-1529.
Kim, J.; Jung, I.-S.; Kim, S.-Y.; Lee, E.; Kang, J.-K.; Sakamoto, S.; Yamaguchi, K.; Kim, K. New Cucurbituril Homologues: Syntheses, Isolation, Characterization, and X-Ray Crystal Structures of Cucurbit[n]uril (n=5, 7, and 8). J. Am. Chem. Soc. 2000, 122, 540-541.
Kim, S.-Y.; Jung, I.-S.; Lee, E.; Kim, J.; Sakamoto, S.; Yamaguchi, K.; Kim, K. Macrocycles within Macrocycles: Cyclen, Cyclam, and Their Transition Metal Complexes Encapsulated in Cucurbit[8]uril. Angew. Chem. Int. Ed. 2001, 40, 2119-2121.
Klosterman, J. K.; Veliks, J.; Frantz, D. K.; Yasui, Y.; Loepfe, M.; Zysman-Colman, E.; Linden, A.; Siegel, J. S. Conformations of Large Macrocycles and Ring-in-Ring Complexes. Org. Chem. Front. 2016, 3, 661-666.
Koshland, D. E. Application of a Theory of Enzyme Specificity to Protein Synthesis. Proc. Natl. Acad. Sci. U. S. A. 1958, 44, 98-104.
Koshland, D. E. The Key-Lock Theory and the Induced Fit Theory. Angew. Chem., Int. Ed. Engl. 1995, 33, 2375-2378.
Lee, S.; Chen, C. H.; Flood, A. H. A Pentagonal Cyanostar Macrocycle with Cyanostilbene CH Donors Binds Anions and Forms Dialkylphosphate [3]Rotaxanes. Nat. Chem. 2013, 5, 704-710.
Lehn, J.-M. Supramolecular Chemistry: Receptors, Catalysts, and Carriers. Science 1985, 227, 849-856.
Lehn, J.-M. Supramolecular Chemistry—Scope and Perspectives Molecules, Supermolecules, and Molecular Devices (Nobel Lecture). Angew. Chem., Int. Ed. Engl. 1988, 27, 89-112.
Leininger, S.; Olenyuk, B.; Stang, P. J. Self-Assembly of Discrete Cyclic Nanostructures Mediated by Transition Metals. Chem. Rev. 2000, 100, 853-908.
Li, S.; Peele, B. N.; Larson, C. M.; Zhao, H.; Shepherd, R. F. A Stretchable Multicolor Display and Touch Interface Using Photopatterning and Transfer Printing. Adv. Mater. 2016, 28, 9770-9775.
Lipke, M. C.; Cheng, T.; Wu, Y.; Arslan, H.; Xiao, H.; Wasielewski, M. R.; Goddard, W. A., III; Stoddart, J. F. Size-Matched Radical Multivalency. J. Am. Chem. Soc. 2017, 139, 3986-3998.
Lipke, M. C.; Wu, Y.; Roy, I.; Wang, Y.; Wasielewski, M. R.; Stoddart, J. F. Shuttling Rates, Electronic States, and Hysteresis in a Ring-in-Ring Rotaxane. ACS Cent. Sci. 2018, 4, 362-371.
Liu, S.; Ruspic, C.; Mukhopadhyay, P.; Chakrabarti, S.; Zavalij, P. Y.; Isaacs, L. The Cucurbit[n]uril Family: Prime Components for Self-Sorting Systems. J. Am. Chem. Soc. 2005, 127, 15959-15967.
Liu, S.; Zavalij, P. Y.; Isaacs, L. Cucurbit[10]uril. J. Am. Chem. Soc. 2005, 127, 16798-16799.
Liu, Y.; Zhao, W.; Chen, C. H.; Flood, A. H. Chloride Capture Using a C-H Hydrogen-Bonding Cage. Science 2019, 365, 159-161.
Loren, J. C.; Yoshizawa, M.; Haldimann, R. F.; Linden, A.; Siegel, J. S. Synthetic Approaches to a Molecular Borromean Link: Two-Ring Threading with Polypyridine Templates. Angew. Chem. Int. Ed. 2003, 42, 5702-5705.
Lu, Y.; Zhang, H. N.; Jin, G. X. Molecular Borromean Rings Based on Half-Sandwich Organometallic Rectangles. Acc. Chem. Res. 2018, 51, 2148-2158.
Lukinavicius, G.; Reymond, L.; Umezawa, K.; Sallin, O.; D'Este, E.; Gottfert, F.; Ta, H.; Hell, S. W.; Urano, Y.; Johnsson, K. Fluorogenic Probes for Multicolor Imaging in Living Cells. J. Am. Chem. Soc. 2016, 138, 9365-9368.
Marenich, A. V.; Cramer, C. J.; Truhlar, D. G. Universal Solvation Model Based on Solute Electron Density and on a Continuum Model of the Solvent Defined by the Bulk Dielectric Constant and Atomic Surface Tensions. J. Phys. Chem. B, 2009, 113, 6378-6396.
Mei, J.; Leung, N. L.; Kwok, R. T.; Lam, J. W.; Tang, B. Z. Aggregation-Induced Emission: Together We Shine, United We Soar! Chem. Rev. 2015, 115, 11718-11940.
Mena-Hernando, S.; Perez, E. M. Mechanically Interlocked Materials. Rotaxanes and Catenanes Beyond the Small Molecule. Chem. Soc. Rev. 2019, 48, 5016-5032.
Mock, W. L.; Shih, N. Y. Host-Guest Binding Capacity of Cucurbituril. J. Org. Chem. 1983, 48, 3618-3619.
Neese, F. An Improvement of the Resolution of the Identity Approximation for the Calculation of the Coulomb Matrix. J. Comp. Chem., 2003, 24, 1740-1747.
Neese, F. The ORCA Program System. Wiley Interdiscip. Rev.: Comput. Mol. Sci., 2012, 2, 73-78.
Ni, X. L.; Chen, S.; Yang, Y.; Tao, Z. Facile Cucurbit[8]uril-Based Supramolecular Approach to Fabricate Tunable Luminescent Materials in Aqueous Solution. J. Am. Chem. Soc. 2016, 138, 6177-6183.
Odell, B.; Reddington, M. V.; Slawin, A. M. Z.; Spencer, N.; Stoddart, J. F.; Williams, D. J. Cyclobis(paraquat-p-phenylene). A Tetracationic Multipurpose Receptor. Angew. Chem., Int. Ed. Engl. 1988, 27, 1547-1550.
Ogoshi, T.; Yamagishi, T. A.; Nakamoto, Y. Pillar-Shaped Macrocyclic Hosts Pillar[n]arenes: New Key Players for Supramolecular Chemistry. Chem. Rev. 2016, 116, 7937-8002.
Olesinska, M.; Wu, G.; Gomez-Coca, S.; Anton-Garcia, D.; Szabo, I.; Rosta, E.; Scherman, O. A. Modular Supramolecular Dimerization of Optically Tunable Extended Aryl Viologens. Chem. Sci. 2019, 10, 8806-8811.
Ong, W.; Kaifer, A. E. Salt Effects on the Apparent Stability of the Cucurbit[7]uril-Methyl Viologen Inclusion Complex. J. Org. Chem. 2004, 69, 1383-1385.
Peck, E. M.; Liu, W.; Spence, G. T.; Shaw, S. K.; Davis, A. P.; Destecroix, H.; Smith, B. D. Rapid Macrocycle Threading by a Fluorescent Dye-Polymer Conjugate in Water with Nanomolar Affinity. J. Am. Chem. Soc. 2015, 137, 8668-8671.
Pedersen, C. J. Cyclic Polyethers and Their Complexes with Metal Salts. J. Am. Chem. Soc. 1967, 89, 2495-2496.
Pedersen, C. J. The Discovery of Crown Ethers (Nobel Lecture). Angew. Chem., Int. Ed. Engl. 1988, 27, 1021-1027.
Peng, S.; He, Q.; Vargas-Zuniga, G. I.; Qin, L.; Hwang, I.; Kim, S. K.; Heo, N. J.; Lee, C. H.; Dutta, R.; Sessler, J. L. Strapped Calix[4]pyrroles: From Syntheses to Applications. Chem. Soc. Rev. 2020, 49, 865-907.
Philp, D.; Slawin, A. M. Z.; Spencer, N.; Stoddart, J. F.; Williams, D. J. The Complexation of Tetrathiafulvalene by Cyclobis(paraquat-p-phenylene). J. Chem. Soc., Chem. Commun. 1991, 1584-1586.
Qi, Q.; Li, C.; Liu, X.; Jiang, S.; Xu, Z.; Lee, R.; Zhu, M.; Xu, B.; Tian, W. Solid-State Photoinduced Luminescence Switch for Advanced Anticounterfeiting and Super-Resolution Imaging Applications. J. Am. Chem. Soc. 2017, 139, 16036-16039.
Rappe, A. K.; Casewit, C. J.; Colwell, K. S.; Goddard, W. A.; Skiff, W. M. Uff, A Full Periodic Table Force Field for Molecular Mechanics and Molecular Dynamics Simulations. J. Am. Chem. Soc. 1992, 114, 10024-10035.
Rappe, A. K.; Colwell, K. S.; Casewit, C. J. Application of a Universal Force Field to Metal Complexes. Inorg. Chem. 1993, 32, 3438-3450.
Raymo, F. M.; Stoddart, J. F. Interlocked Macromolecules. Chem. Rev. 1999, 99, 1643-1664.
Rekharsky, M. V.; Inoue, Y. Complexation Thermodynamics of Cyclodextrins. Chem. Rev. 1998, 98, 1875-1918.

(56) References Cited

OTHER PUBLICATIONS

Rousseaux, S. A.; Gong, J. Q.; Haver, R.; Odell, B.; Claridge, T. D.; Herz, L. M.; Anderson, H. L. Self-Assembly of Russian Doll Concentric Porphyrin Nanorings. J. Am. Chem. Soc. 2015, 137, 12713-12718.
Sawada, T.; Hisada, H.; Fujita, M. Mutual Induced Fit in a Synthetic Host-Guest System. J. Am. Chem. Soc. 2014, 136, 4449-4451.
Sheldrick, G. M. A Short History of SHELX. Acta. Cryst. 2008, A64, 112-122.
Sheldrick, G. M. SHELXT• Integrated Space-Group and Crystal-Structure Determination. Acta. Cryst. 2015, A71, 3-8.
Sinn, S.; Spuling, E.; Brase, S.; Biedermann, F. Rational Design and Implementation of a Cucurbit[8]uril-Based Indicator-Displacement Assay for Application in Blood Serum. Chem. Sci. 2019, 10, 6584-6593.
Spruell, J. M.; Coskun, A.; Friedman, D. C.; Forgan, R. S.; Sarjeant, A. A.; Trabolsi, A.; Fahrenbach, A. C.; Barin, G.; Paxton, W. F.; Dey, S. K.; Olson, M. A.; Benitez, D.; Tkatchouk, E.; Colvin, M. T.; Carmielli, R.; Caldwell, S. T.; Rosair, G. M.; Hewage, S. G.; Duclairoir, F.; Seymour, J. L.; Slawin, A. M.; Goddard, W. A., III; Wasielewski, M. R.; Cooke, G.; Stoddart, J. F. Highly Stable Tetrathiafulvalene Radical Dimers in [3]Catenanes. Nat. Chem. 2010, 2, 870-879.
Stoddart, J. F. The Chemistry of the Mechanical Bond. Chem. Soc. Rev. 2009, 38, 1802-1820.
Stoychev, G. L.; Auer, A. A.; Neese, F. Automatic Generation of Auxiliary Basis Sets. J. Theo. Comp. Chem. 2017, 13, 554-562.
Su, Y.; Phua, S. Z. F.; Li, Y.; Zhou, X.; Jana, D.; Liu, G.; Lim, W. Q.; Ong, W. K.; Yang, C.; Zhao, Y. Ultralong Room Temperature Phosphorescence from Amorphous Organic Materials toward Confidential Information Encryption and Decryption. Sci. Adv. 2018, 4, eaas9732.
Su, Y.; Zhang, Y.; Wang, Z.; Gao, W.; Jia, P.; Zhang, D.; Yang, C.; Li, Y.; Zhao, Y. Excitation-Dependent Long-Life Luminescent Polymeric Systems under Ambient Conditions. Angew. Chem. Int. Ed. 2020, 59, 9967-9971.
Sun, B.; Wang, M.; Lou, Z.; Huang, M.; Xu, C.; Li, X.; Chen, L. J.; Yu, Y.; Davis, G. L.; Xu, B.; Yang, H. B.; Li, X. From Ring-in-Ring to Sphere-in-Sphere: Self-Assembly of Discrete 2D and 3D Architectures with Increasing Stability. J. Am. Chem. Soc. 2015, 137, 1556-1564.
Tang, X.; Huang, Z.; Chen, H.; Kang, Y.; Xu, J. F.; Zhang, X. Supramolecularly Catalyzed Polymerization: From Consecutive Dimerization to Polymerization. Angew. Chem. Int. Ed. 2018, 57, 8545-8549.
Te Velde, G.; Bickelhaupt, F. M.; Baerends, E. J.; Fonseca Guerra, C.; van Gisbergen, S. J. A.; Snijders, J. G.; Ziegler, T. Chemistry with ADF. J. Comput. Chem. 2001, 22, 931-967.
Tian, J.; Zhou, T. Y.; Zhang, S. C.; Aloni, S.; Altoe, M. V.; Xie, S. H.; Wang, H.; Zhang, D. W.; Zhao, X.; Liu, Y.; Li, Z. T. Three-Dimensional Periodic Supramolecular Organic Framework Ion Sponge in Water and Microcrystals. Nat. Commun. 2014, 5, 5574.
Van Lenthe, E.; Baerends, E. J. Optimized Slater-Type Basis Sets for the Elements 1-118. J. Comput. Chem. 2003, 24, 1142-1156.
Wang, Q.; Zhang, Q.; Zhang, Q. W.; Li, X.; Zhao, C. X.; Xu, T. Y.; Qu, D. H.; Tian, H. Color-Tunable Single-Fluorophore Supramolecular System with Assembly-Encoded Emission. Nat. Commun. 2020, 11, 158.
Wei, P.; Zhang, X.; Liu, J.; Shan, G. G.; Zhang, H.; Qi, J.; Zhao, W.; Sung, H. H.; Williams, I. D.; Lam, J. W. Y.; Tang, B. Z. New Wine in Old Bottles: Prolonging Room-Temperature Phosphorescence of Crown Ethers by Supramolecular Interactions. Angew. Chem. Int. Ed. 2020, 59, 9293-9298.

* cited by examiner (c)

Figure 13
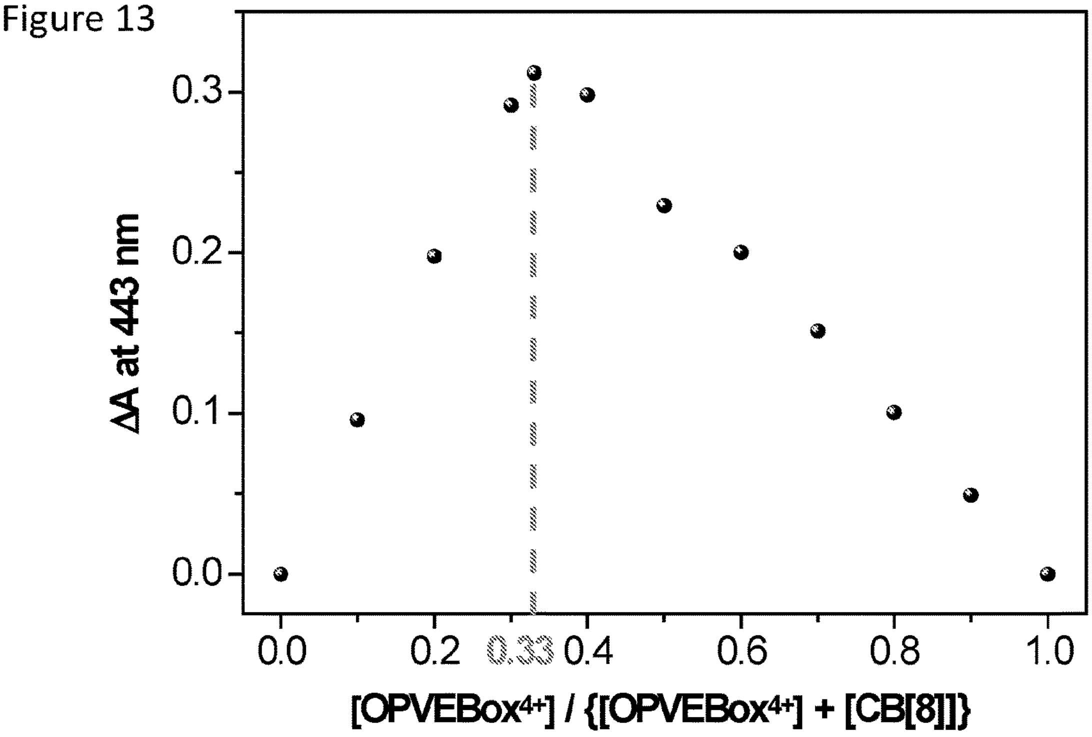
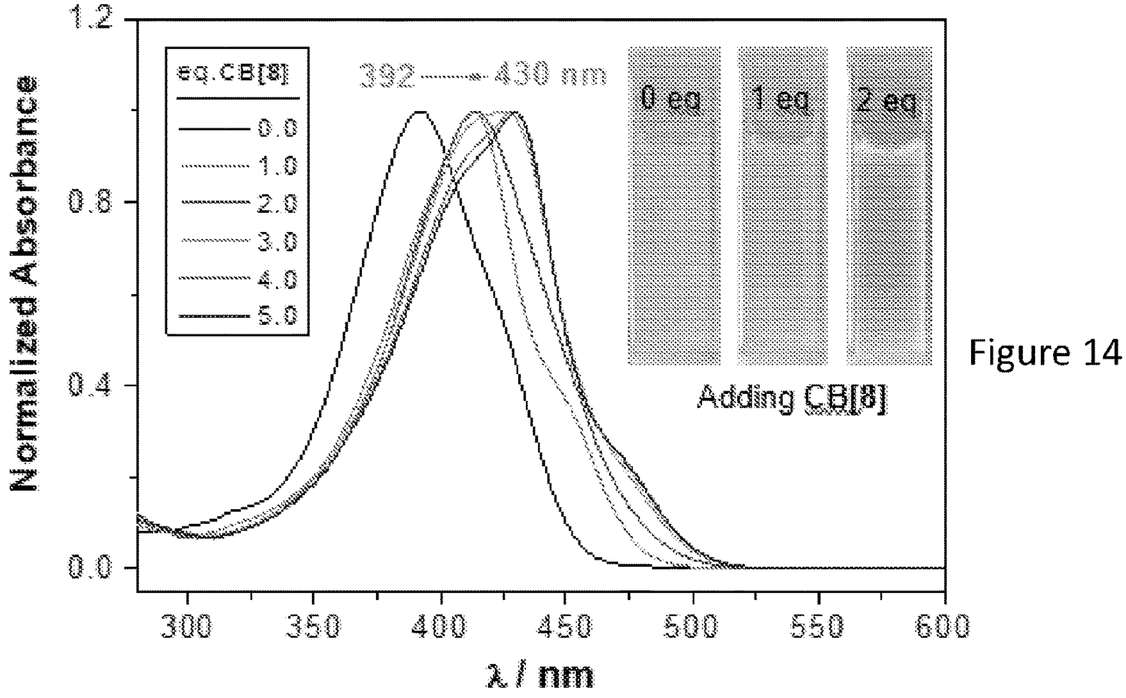
Figure 14

(a)

(b)

(a) (b)

(a) (b)

RING-IN-RING COMPLEXES EXHIBITING TUNABLE MULTICOLOR PHOTOLUMINESCENCE

CROSS-REFERENCE TO RELATED APPLICATIONS

This application represents the national stage entry of PCT/US2021/071284 filed Aug. 25, 2021, which claims benefit of priority to US Application Ser. No. 63/070,113, filed Aug. 25, 2020, the contents of each are incorporated by reference in their entireties.

BACKGROUND OF THE INVENTION

One ring threaded by two other rings to form a non-intertwined ternary ring-in-rings motif is a challenging task in noncovalent synthesis. Fluorescent molecules with tunable emission colors have attracted an increasing amount of attention because of their potential applications in multidimensional bioimaging, encryption materials, and visual displays. Conventional methods of controlling the emission of fluorescent molecules involve mainly covalent modification. In contrast to conventional approaches, noncovalent strategies can be an efficient way to fabricate smart optical materials, in which fluorescent molecules display distinctive photophysical properties when participating in host-guest complexation. As a result, there is a need for constructing luminescent host-guest complexes, which can integrate the features of wavelength tunability, water solubility, and applicability to a wide concentration range.

BRIEF SUMMARY OF THE INVENTION

Disclosed herein is a ring-in-ring photoluminescent complex comprising a host cyclophane and a guest cyclophane threaded through the host cyclophane. The ring-in-ring photoluminescent complex may be a 1:1 host-guest complex, a 2:1 host-guest complex, or a combination thereof, wherein the guest cyclophane has a first photoluminescent emission maxima, the 1:1 host-guest complex has a second photoluminescent emission maxima, the 2:1 host-guest complex with the host cyclophane has a third photoluminescent emission maxima, and each of the first, second, and third photoluminescent emission maxima is different. In some embodiments, the complex is the 1:1 host-guest complex. In some embodiments, the complex is the 2:1 host-guest complex.

In some embodiments, the host cyclophane is a cucurbit[n]uril or the guest cyclophane is a tetracationic cyclophane. In some embodiments, the host cyclophane is cucurbit[8]uril. In some embodiments, the guest cyclophane is

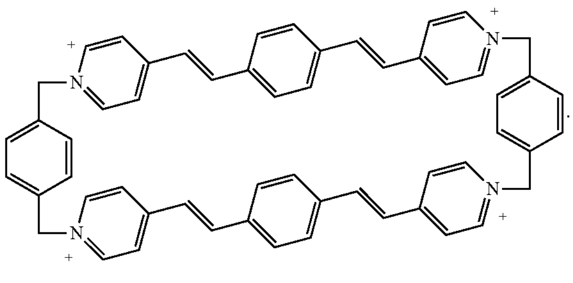

.

Another aspect of the invention provides for a photoluminescent composition. The photoluminescent composition may comprise the host cyclophane and the guest cyclophane, wherein the composition is capable of forming any of the ring-in-ring photoluminescent complexes as described herein and wherein molar ratio of the host cyclophane to the guest cyclophane in the composition determines the frequency of emitted radiation.

Another aspect of the invention provides for a method of inducing photoluminescence. The method may comprise irradiating any of the ring-in-ring photoluminescent complexes as described herein. The method may comprise irradiating any of the compositions as described herein.

Another aspect of the invention provides for a method for tuning photoluminescence. The method may comprise providing a host cyclophane and a guest cyclophane, contacting the guest cyclophane with the host cyclophane thereby forming any of the ring-in-ring photoluminescent complex as described herein, and irradiating the complex, wherein a molar ratio of host cyclophane to the guest cyclophane determines the frequency of emitted radiation.

These and other aspects of the invention will be further described herein.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention.

FIG. 13. Job's experiment for OPVEBox$^{4+}$ upon complexation with CB[8] in aqueous solution at 298 K. Absorbance intensity changes of OPVEBox$^{4+}$ recorded at 443 nm was used to analyze the binding ratio. The total concentration of host and guest is constant ([OPVEBox$^{4+}$]+[CB[8]]=100 μM).

FIG. 14. Normalized UV-Vis absorption spectra ([OPVEBox·$^{4+}$]=4 μM, [CB[8]]=0-20 μM, $H_2O$, 298 K) of OPVEBox$^{4+}$ with adding different equiv of CB[8]. The maximum absorption wavelength red shifted from 392 to 430 nm.

DETAILED DESCRIPTION OF THE INVENTION

Figure 1:
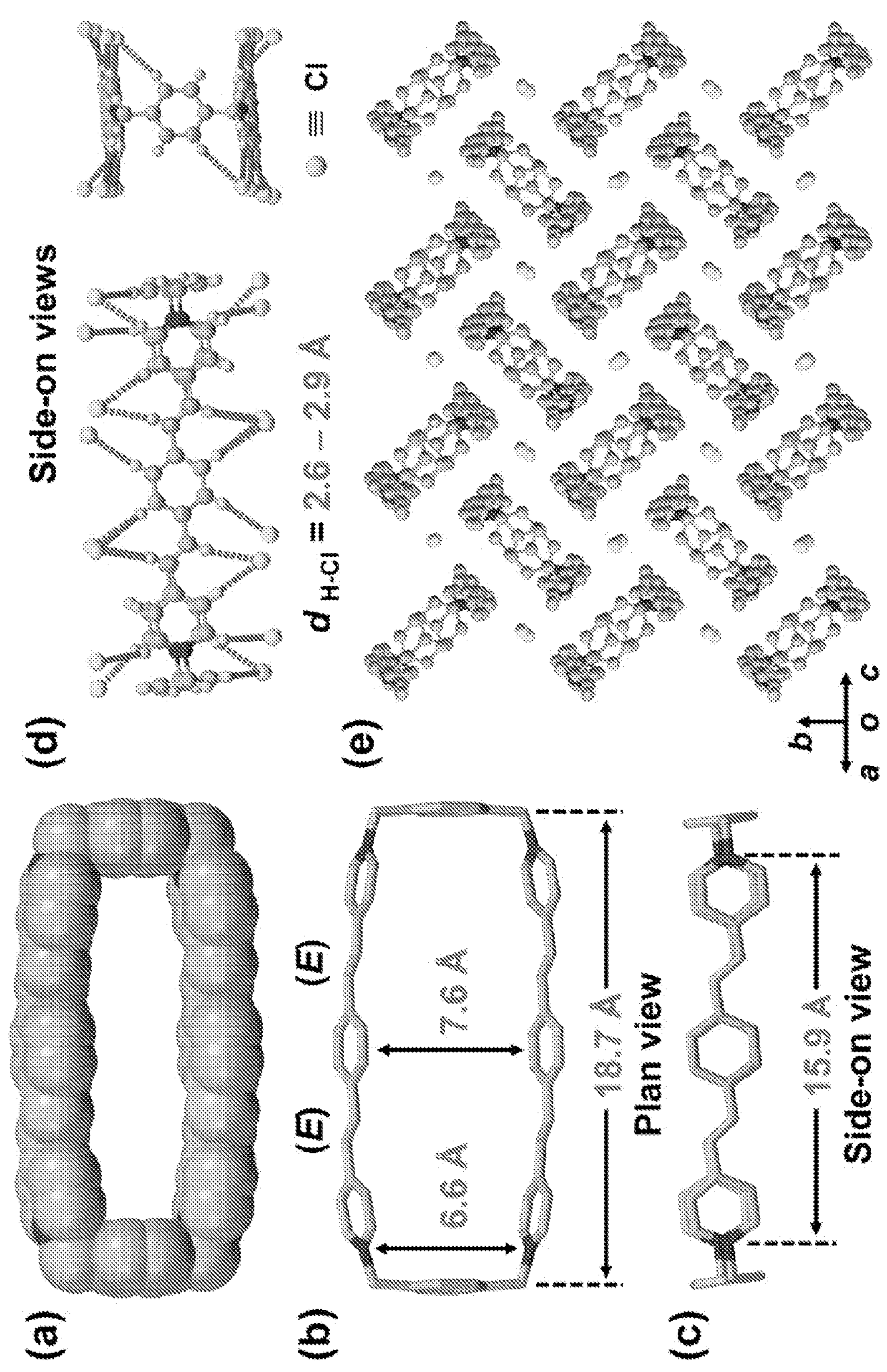
FIG. 1. Solid-state (super)structure of OPVEBox$^{4+}$ obtained by X-ray crystallography on single crystals of OPVEBox·4Cl. (a) Space-filling representation, showing the box-like geometry of OPVEBox$^{4+}$. (b-c) Capped-stick representations of plan and side-on views, showing the distances defining the box-like geometry of OPVEBox$^{4+}$. (d) Ball-and-stick representations of different side-on views, showing how OPVEBox$^{4+}$ interacts with 16 Cl anions by [C—HCl . . . Cl$^-$] hydrogen bonding. (e) Solid-state superstructure of OPVEBox·4Cl, revealing how OPVEBox$^{4+}$ and the Cl$^-$ anions adopt an alternating arrangement. Solvent molecules have been omitted for the sake of clarity. H gray, C sky-blue, N blue, Cl green. (f) Structural formulas and schematic illustrations of the different binding behaviors of CBPQT$^{4+}$. (g) Structural formulas and schematic illustrations of the different binding behaviors of OPVEBox$^{4+}$ with CB[8].
Figure 1:
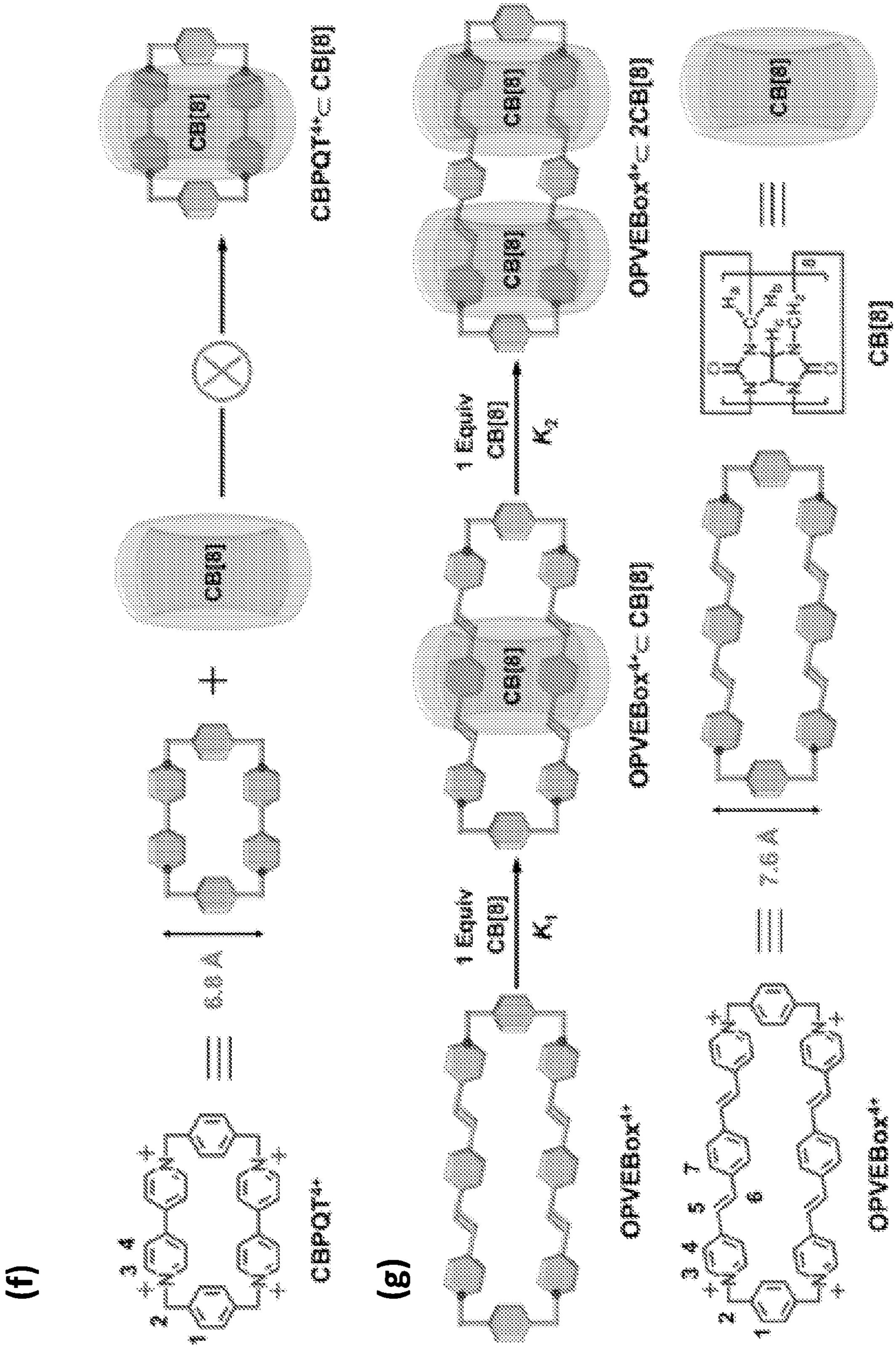

Herein, we describe the design and synthesis of binary and ternary ring-in-ring(s) complexes. The formation of these complexes may be accompanied by tunable multi-color-photoluminescent outputs. On mixing host and guest cyclophanes, a 1:1 ring-in-ring complex may be formed as a result of noncovalent interactions between the host and guest cyclophane. With the addition of additional host cyclophane, 2:1 host-guest complexes may be formed, facilitated by additional noncovalent interactions. The interaction between the guest cyclophane and host cyclophane may result in a narrowing or broadening of the energy gaps of a photoluminescent component within the cavity of a first host cyclophane. The energy gap of the photoluminescent guest cyclophane may be further narrowed or broadened with the cavity of a second cyclophane. A series of color-tunable emissions is achievable with the formation different relative proportions of fluorescent guest cyclophane, 1:1 host-guest complex, and 2:1 host complexes because each have a different photoluminescent emission maxima. Increased photoluminescent lifetimes may also be achieved by adding the host cyclophane to a solution of the guest cyclophane.

Ring-in-ring complex refers to complex formed by two or more macrocycles where at least one of the macrocycle is threaded through another macrocycle. Macrocycle refers to a cyclic macromolecular or a macromolecular cyclic portion of a macromolecule. Macromolecule refers to a molecule of high relative molecular mass, the structure of which essentially comprises the multiple repetition of units derived, actually or conceptually, from molecules of low relative molecular mass. The macrocycle threaded, or capable of being threaded, into the cavity of another macrocycle is referred to as a guest. The macrocycle surrounding, or capable of being surrounding, another macrocycle is referred to as the host. The ring-in-ring complex may comprise a 1:1 host-guest complex, 2:1 host-guest complex, or a combination thereof. A 1:1 host-guest complex refers to a complex having one guest and one host. A 2:1 host-guest complex refers to a complex having one guest and two hosts.

In some embodiments, the macrocycle is cyclophane. Cyclophane refers to compounds having (i) mancude-ring systems, or assemblies of mancude-ring systems, and (ii) atoms and/or saturated or unsaturated chains as alternate components of a large ring. Mancude-ring systems refers to rings having (formally) the maximum number of noncumulative double bonds, e.g. benzene, indene, indole, 4H-1,3-dioxine, and the like.

The guest may be a tetracationic cyclophane. Tetracationic cyclophanes comprise a 4+ charge. In some embodiments, the tetracationic cyclophane comprises two viologen units and two linker units. The two viologens may be the same or different. The units of the cyclophane may comprise an ordered, cyclic arrangement alternating between viologen unit and linker unit. Suitably, these cyclophanes comprise rigid or semi-rigid, box-like compositions.

A viologen refers to structural unit composed of two pyridine groups, where each pyridine is capable of carrying a 1+ charge. Viologens may comprise a conjugated spacer interposed between the two pyridine groups. The spacer may be selected by size to allow the guest to be threaded into two hosts, by complexing interactions to allow for stable complexation of the host and guest in certain environments and/or promote complex dissociation in other environments, and/or by photoluminescent properties to allow for tuning photoluminescent outputs. Suitably the conjugated spacer may be an aromatic spacer or an unsaturated alkyl spacer to allow for resonance across the extended viologen. Exemplary conjugated spacers include, without limitation, homocyclic aromatic spacers (e.g., a phenyl spacer, a naphthyl spacer, or an anthracene spacer), heterocyclic aromatic spacers (e.g., a thiazolothiazole spacer, a benzobisthiadiazole spacer, a thiophene spacer, a pyrrole spacer), alkenyl spacers (e.g., ethene), or alkynyl spacers. The conjugated spacer may be substituted by one of more substituents. Suitably the extended viologen comprises an aromatic spacer and two alkenyl spacers. As exemplified in the Examples, the viologen may be

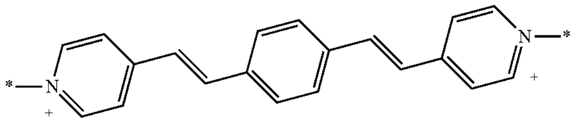

where * indicates how the viologen is installed into the guest.

The linker unit may be selected by size to fix the distance between the viologen units. In some embodiments, the linker unit may comprise a central aryl moiety, such as a phenyl. As exemplified in the Examples, the linker unit may be

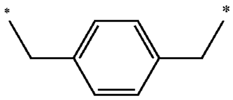

where * indicates how the linker unit is installed into the guest.

An exemplary guest is the tetracationic cyclophane OPVEBox

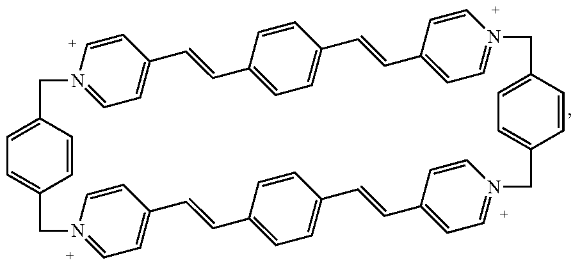

, incorporating two extended viologen units (1,4-BPEB) linked end-to-end by two p-xylylene linkers.

The host may be a cucurbituril. Cucurbituril refers to a macrocyclic molecule made of glycoluril ($=C_4H_2N_4O_2=$) monomers linked by methylene bridges ($-CH_2-$). Cucurbituril may generically be referred to as cucurbit[n]uril or CB [n] wherein n is the number of glycoluril units. Cucurbiturils are amidals and synthesized from urea and a dialdehyde (e.g., glyoxal) via a nucleophilic addition to give the intermediate glycoluril. This intermediate is condensed with formaldehyde to give cucurbit[n]uril. Controlling the temperature during condensation allows access to other sizes of cucurbiturils, including CB[5], CB[6], CB[7], CB[8], and CB[10]. In exemplary embodiments, the host is CB[8].

Photoluminescence refers to light emission from any form of matter after irradiation and absorption of photons. Following excitation, relaxation processes occur in which other photons are radiated. The radiated photons typically have a longer wavelength, i.e., have lower energy, than the absorbed photons. In some embodiments, the matter is irradiated with photons in the ultraviolet or visible spectrum and the radiated photons may be in the visible or infrared spectrum. The matter may be irradiated with photons over a range of wavelengths, resulting in a characteristic emission profile having one or more maxima. Suitably, photoluminescence may refer to a resonant process such as fluorescence.

Photoluminescent complex refers to a complex capable of emitting photons after irradiation. In some embodiments, the guest is a photoluminescent. In other embodiments, the host may be photoluminescent. The interaction between the host and the guest can modulate the emission profile, resulting in a shift the emission maxima. This modulation will result in a visibly detectable change if the emission occurs in the visible spectrum.

Photoluminescent compositions refers to substance comprising hosts and guests that are capable of forming ring-in-ring photoluminescent complexes. The composition may be comprised of ring-in-ring photoluminescent complexes, including 1:1 host-guest complexes and/or 2:1 host-guest complexes, as well as uncomplexed or free hosts and/or guests. The relative proportion of each of these components will modulate the photoluminescent output. By selecting the molar ratio of the host and guest in the composition, the frequency of emitted radiation, including its maxima, may be determined.

One or more additional components may be used to tune the photoluminescent output. In some embodiments, the photoluminescent composition further comprises a competitive complexation agent. Competitive complexation agent refers to a substance or compound that can bind with either the host or the guest and inhibit complex formation. Competitive guest refers to a substance that can bind with the host to inhibit complex formation. Competitive host refers to substance that can bind with the guest to inhibit complex formation. An exemplary competitive guest is memantine hydrochloride (Mem).

As disclosed in the Examples, binary and ternary ring-in-ring(s) complexes based on an extended tetracationic cyclophane and cucurbit[8]uril have been prepared. The formation of these complexes is accompanied by tunable multicolor-fluorescence outputs. On mixing equimolar amounts of the cyclophane and cucurbit[8]uril, a 1:1 ring-in-ring complex is formed as a result of hydrophobic interactions associated with a favorable change in entropy. With the addition of another equivalent of cucurbit[8]uril, a 1:2 ring-in-rings complex is formed, facilitated by additional ion-dipole interactions involving the pyridinium units in the cyclophane and the carbonyl groups in cucurbit[8]uril. Because of the narrowing in the energy gaps of the cyclophane within the rigid hydrophobic cavities of cucurbit[8]urils, the binary and ternary ring-in-ring(s) complexes emit green and bright yellow fluorescence, respectively. A series of color-tunable emissions, such as sky-blue, cyan, green, and yellow with increased fluorescence lifetimes, can be achieved by simply adding cucurbit[8]uril to an aqueous solution of the tetracationic cyclophane. Notably, the smaller cyclobis(paraquat-p-phenylene), which contains the same p-xylylene linkers as the extended tetracationic cyclophane, does not form ring-in-ring(s) complexes with cucurbit[8]uril. The encapsulation of this extended tetracationic cyclophane by both one and two cucurbit[8]urils provides a feasible approach toward achieving tunable multicolor photoluminescence with a single chromophore.

The rigid tetracationic cyclophane, cyclobis(paraquat-p-phenylene)[15] ($CBPQT^{4+}$), which is composed of two π-electron-deficient bipyridinium ($BIPY^{2+}$) units connected by p-xylylene linkers, has an centroid-to-centroid width of 6.8 Å. The well-defined inner cavity enables the cyclophane to encapsulate π-electron-rich guests. The square-shaped diradical cyclophane [cyclobis(paraquat-4,4'-biphenylene)] $2^{(+\cdot)}$ can encapsulate selectively a [cyclobis(paraquat-m-phenylene)]$2^{(+\cdot)}$ in its cavity to form a tetraradical tetracationic host-guest complex.[21] Upon lengthening the centroid-to-centroid distance between the two $BIPY^{2+}$ units in the outer cyclophane to 13.1 Å, it can form[22] a box-in-box complex with $CBPQT^{4+}$ in their two-electron reduced states. This complex is able to accommodate small aromatic guest molecules inside the void of $CBPQT2^{(+\cdot)}$, forming Russian doll-like assemblies. These two box-in-box superstructures, however, can only survive in an inert atmosphere, because of the instability of the $BIPY^{+\cdot}$ radical under ambient conditions.

Cucurbit[n]uril[23] (CB[n]), benefiting from their well-defined electron negative carbonyl portals and hydrophobic cavities, show high binding affinities for methyl viologen dications and its derivatives,[24] including[25] the tetracationic cyclophane $CBPQT^{4+}$ in aqueous solutions. Cucurbit[8]uril (CB[8]), with a portal diameter[26] of 9.9 Å, is a relatively large homologue within the CB[n] family. It can (i) bind simultaneously electron-accepting and electron-donating guests in its cavity,[27] or (ii) accommodate two identical guests, e.g., naphthalene[28], arylpyridinium,[29] and others,[30] inside its cavity resulting in compact [π . . . π] stacking. The tetracationic cyclophane $CBPQT^{4+}$, however, is not encapsulated by CB[8] forming a ring-in-ring complex, on account of the rigid conformation of CBPQT4+ and the limited space inside the cavity of CB[8].[25] In this investigation, we found that (FIGS. 1*f* and 1*g*), when installing the oligo(p-phenylenevinylene) bipyridinium ($OPV^{2+}$) units in an extended tetracationic cyclophane, $OPVEBox^{4+}$, CB[8] is able to bind to the outside of this cyclophane, forming ring-in-ring(s) complexes. The binary and ternary ring-in-ring(s) complexes, corresponding to 1:1 and 1:2 stoichiometries between $OPVEBox^{4+}$ and CB[8], can be easily obtained, as confirmed by NMR spectroscopy and electrospray ionization-mass spectrometry (ESI-MS). The formation of the binary $OPVEBox^{4+}\subset$CB[8] and ternary $OPVEBox^{4+}\subset$2CB[8] ring-in-ring(s) complexes are sustained, for the most part, by hydrophobic and ion-dipole interactions. Moreover, on account of the specific electronic distributions of $OPVEBox^{4+}$ inside the rigid hydrophobic cavity of CB[8], the binary and ternary ring-in-ring(s) complexes display green and bright yellow fluorescence, respectively. They are red shifted significantly compared with the sky-blue fluorescence of free $OPVEBox^{4+}$. Fluorescence spectroscopy and visual images reveal a variety of fluorescence colors, e.g., sky-blue, cyan, green, and yellow with increased fluorescence lifetimes, which can be reversibly obtained by adding different equivalents of CB[8] to an aqueous solution of OPVEBox·4Cl, and following with the addition of competitive guest.

Synthesis of $OPVEBox^{4+}$ $OPVEBox^{4+}$ was prepared (SCHEME 1) in three steps. The key building block, 1,4-BPEB, was synthesized in 60% yield from a Knoevenagel condensation between terephthalaldehyde and 4-picoline in acetic anhydride solution. Subsequently, 1,4-BPEB was added dropwise into a MeCN solution of an excess of p-xylylene dibromide under refluxing conditions, leading to the formation of BrOPV·$2PF_6$ after counterion exchange ($NH_4PF_6/H_2O$) in a yield of 82%. Finally, a mixture of equimolar amounts of BrOPV·$2PF_6$ and 1,4-BPEB, as well as 0.2 equiv tetrabutylammonium iodide (TBAI), was heated under refluxing in MeCN for 3 days. A crude product was obtained after precipitating with tetrabutylammonium chloride (TBACl). The desired product $OPVEBox^{4+}$ was obtained as its $PF_6$ salt in 40% yield following reverse-phase column chromatography and counterion exchange ($NH_4PF_6/H_2O$). The water-soluble counterpart, namely OPVEBox·4Cl, was then obtained from OPVEBox·$4PF_6$ by counterion exchange (TBACl/MeCN).

Characterization of $OPVEBox^{4+}$

Figure 11:
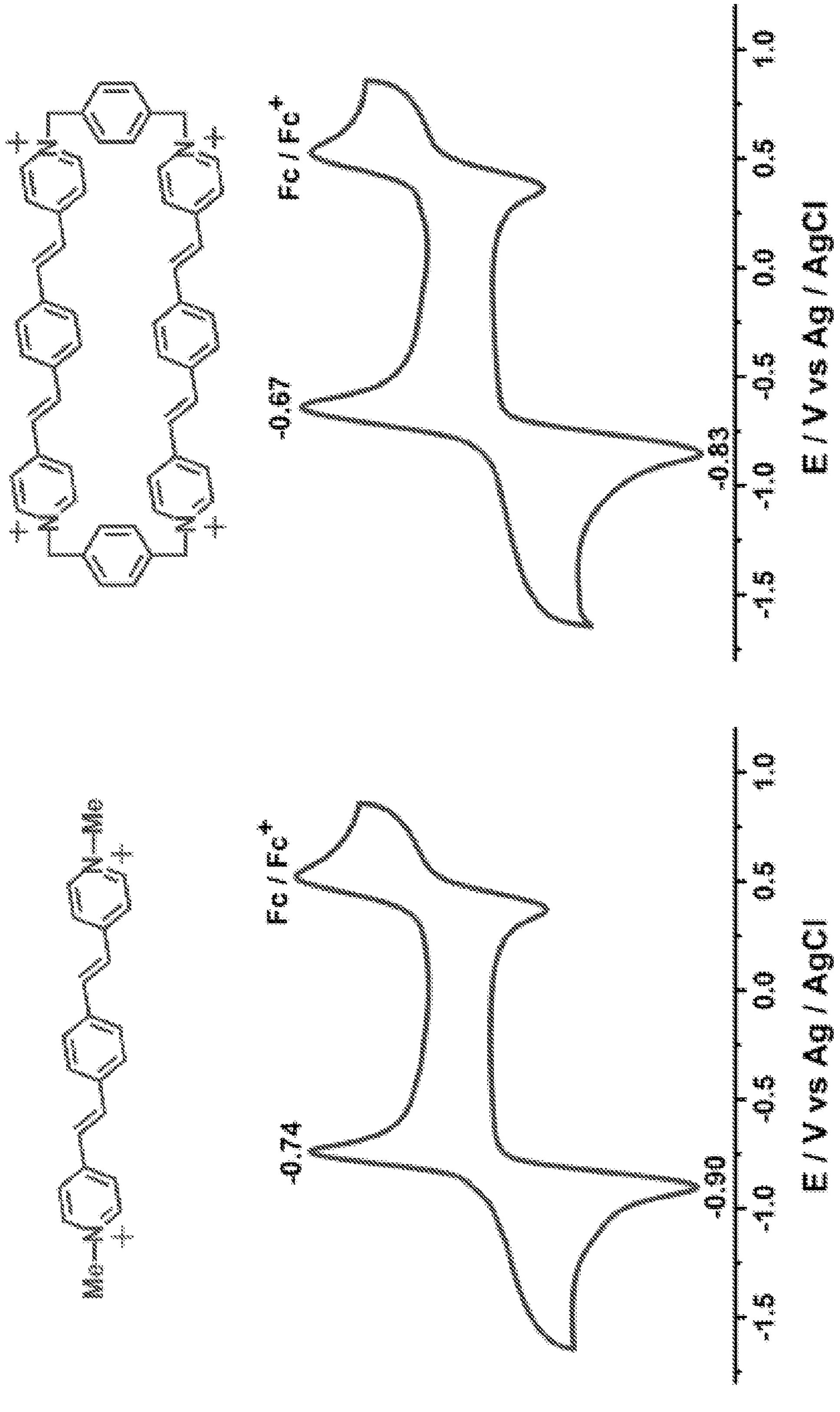
FIG. 11. Cyclic voltammograms ([OPV$^{2+}$]=1.0 mM, [OPVEBox$^{4+}$]=0.5 mM) of OPV$^{2+}$ (left) and OPVEBox$^{4+}$ (right). The results show similar cyclic voltammogram with one set of reversible redox peaks, indicating the absence of electron communication between the pyridinium units.
Figure 12:
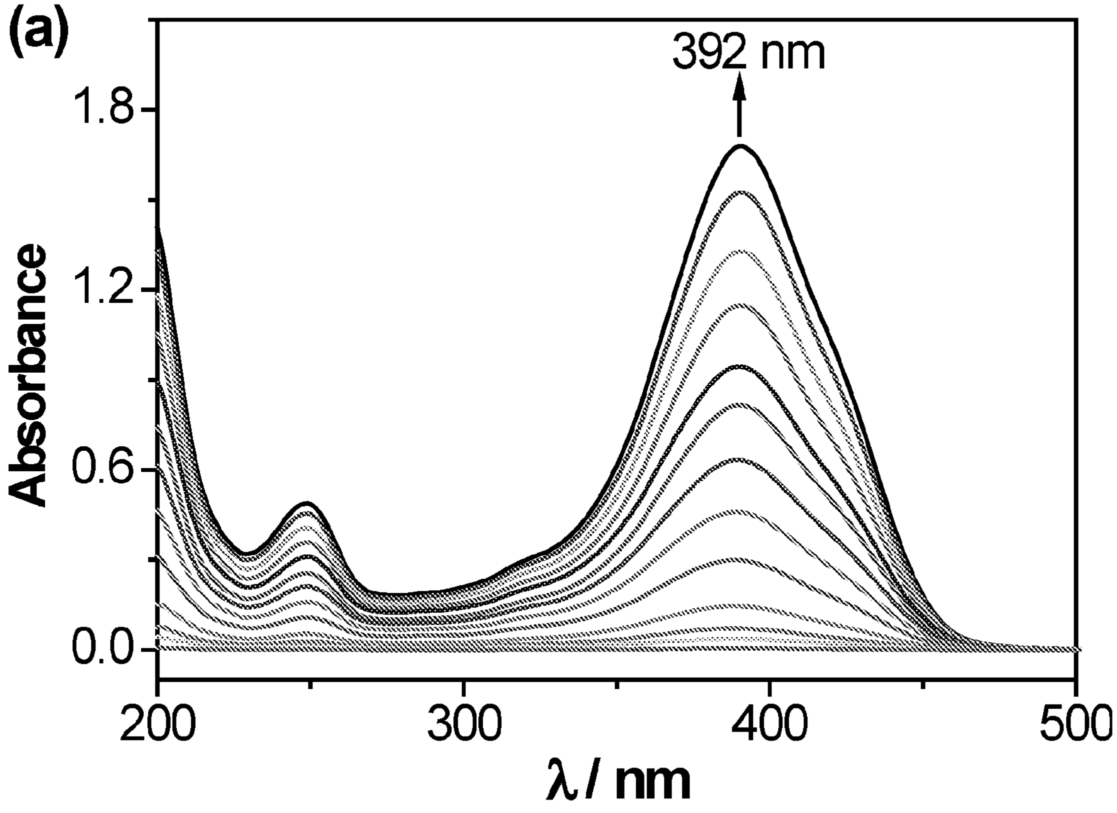
FIG. 12. (a) UV-Vis Absorption spectra ([OPVEBox·$^{4+}$]=0.1-20.0 μM, $H_2O$, 298 K) of OPVEBox$^{4+}$ in different concentrations; (b) Absorbance changes at 392 nm with increasing concentration. The linear relation between absorbance and concentration indicates that there is no aggregation occurring for OPVEBox$^{4+}$ at the concentrations used in the analysis.
Figure 12:
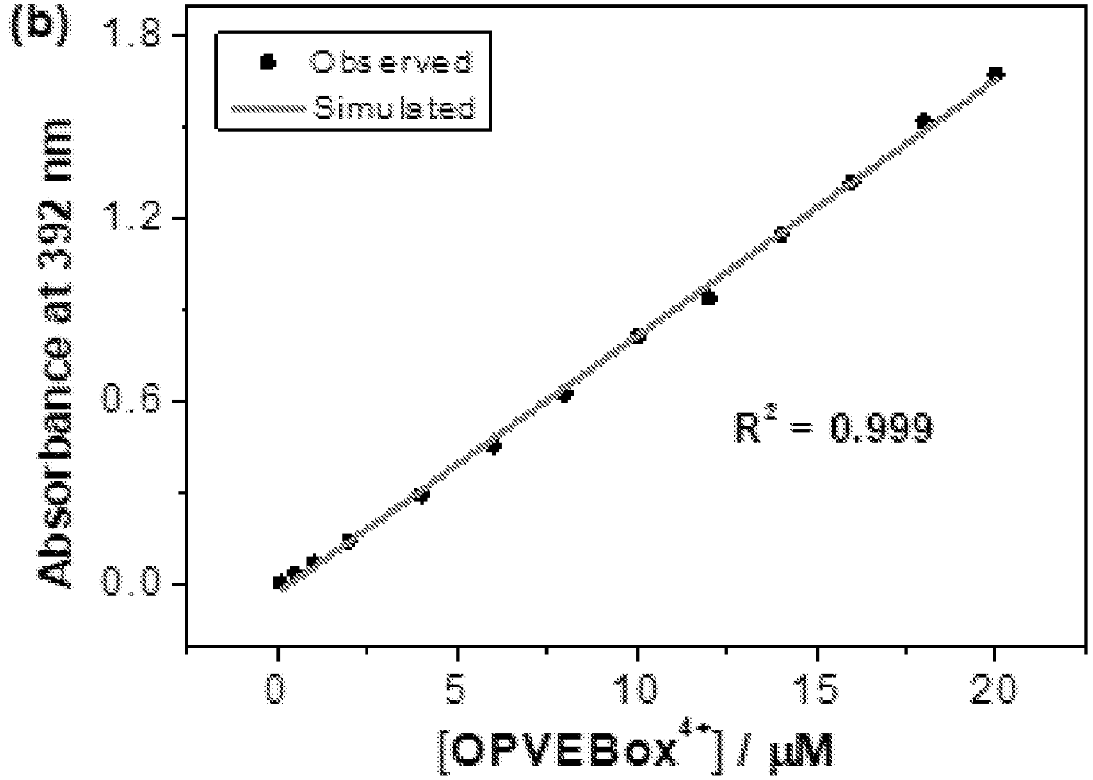
Figure 18:
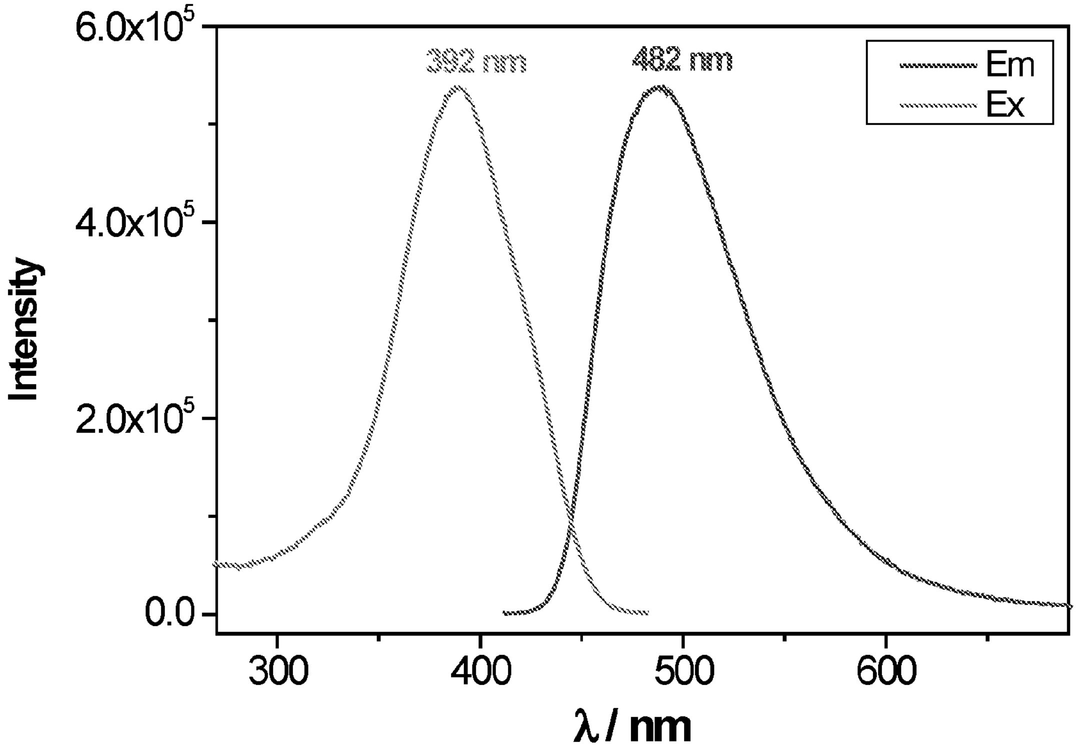
FIG. 18. Excitation and emission spectra ([OPVEBox·$^{4+}$]= 2 μM, $H_2O$, 298 K) of OPVEBox$^{4+}$ in an aqueous solution.
Figure 19:
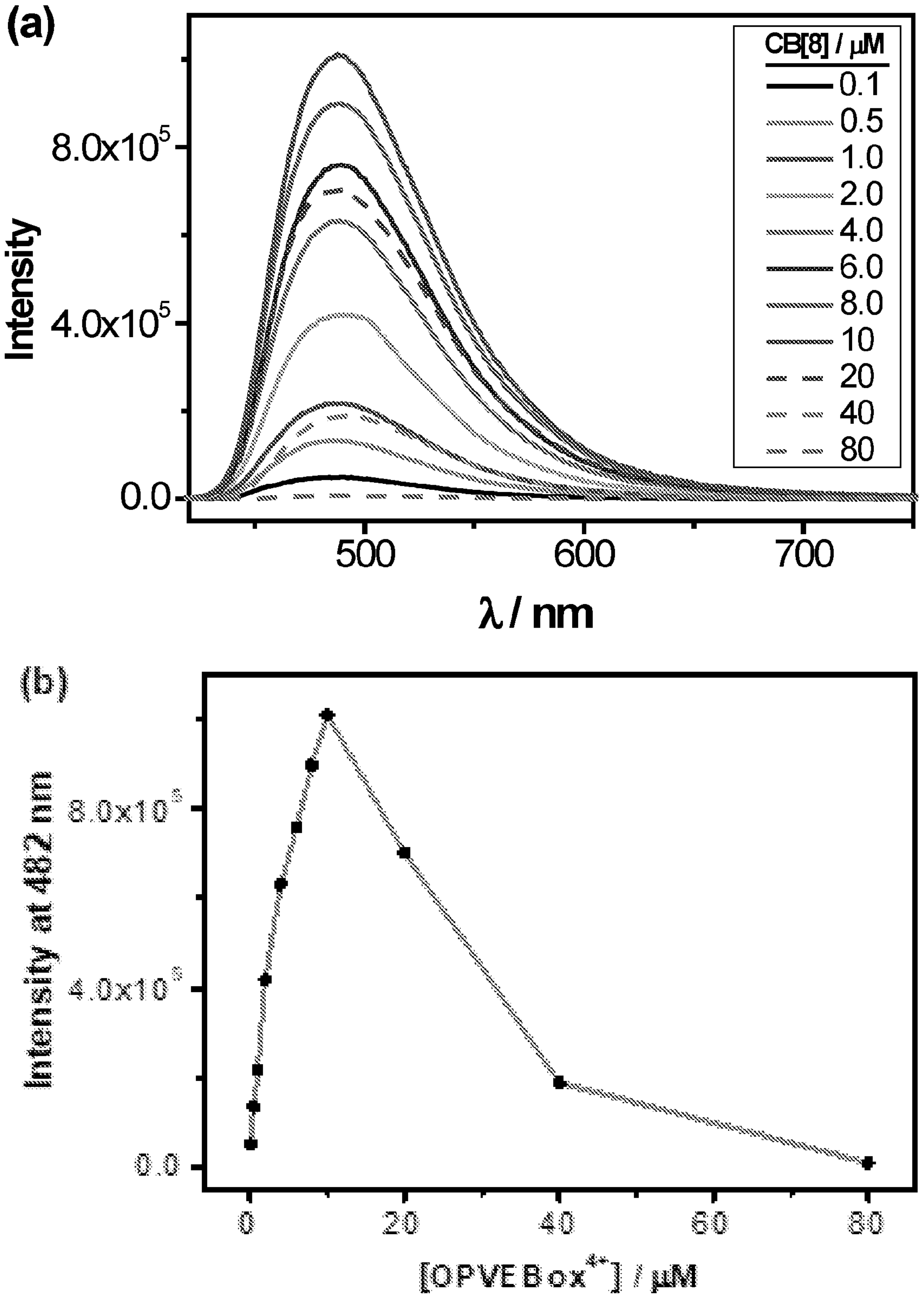
FIG. 19. (a) Emission spectra ([OPVEBox·$^{4+}$]=0.1-80.0 μM, λex=392 nm, $H_2O$, 298 K) of OPVEBox$^{4+}$ in different concentration, (b) Emission intensity changes at 482 nm with increasing concentration, indicating there are no obvious aggregation for $OPVEBox^{4+}$ at the concentration lower than 10.0 μM.

OPVEBox·4Cl was fully characterized by one dimensional and two dimensional (2D) $^1$H and $^{13}$C NMR spectroscopies, as well as by ESI-MS, which revealed the presence of $[M-2Cl]^{2+}$ and $[M-4Cl]^{4+}$ ions with m/z values of 423.16 and 194.10, respectively. The UV-Vis absorption spectrum (FIG. 12) of OPVEBox·4Cl shows a strong absorption peak at 392 nm, and its aqueous solution exhibits (FIG. 18) sky-blue fluorescence with a maximum emission wavelength at 482 nm. When changing the concentration of $OPVEBox^{4+}$ from 0.1 to 10.0 μM, the intensity of the fluorescence increases (FIG. 19) more or less linearly with concentration. The intensity, however, shows a downward trend upon changing the concentration from 10.0 to 80.0 μM. These observations indicate that there is no obvious aggregation-induced fluorescence quenching on the part of $OPVEBox^{4+}$ at concentrations lower than 10.0 μM. The cyclic voltammogram (CV) of $OPVEBox^{4+}$ exhibits (FIG. 11) only one set of reversible redox peaks in degassed DMF, indicating the absence of electronic communications between the pyridinium units within the extended tetracationic cyclophane.

A yellow single crystal of OPVEBox·4Cl was obtained by slow vapor diffusion of $Me_2CO$ into an aqueous solution of OPVEBox·4Cl during the course of one week. Its solid-state structure reveals (FIG. 1*a*) a box-like geometry, with average dimensions (FIG. 1*b*) of 18.7×7.6 Å. The centroid-tocentroid distance (7.6 Å) between two $OPV^{2+}$ units is larger than that[15a] (6.8 Å) in CBPQT4+. The distance between the two nitrogen atoms in the $OPV^{2+}$ unit is (FIG. 1*c*) 15.9 Å, a value which is more than twice the width[26] (6.1 Å) of CB[8]. The solid-state superstructure (FIG. 1) of OPVEBox·4Cl reveals that it crystallizes in a monoclinic space group $P2_1/c$. Every $OPVEBox^{4+}$ molecule interacts (FIG. 1*d*) with 16 Cl anions. The [C—HCl] hydrogen bonding distances range from 2.6 to 2.9 Å. Accordingly, $OPVEBox^{4+}$ and Cl anions adopt an alternating arrangement to form (FIG. 1*e*) a well-ordered array that constitutes the solid-state superstructure. By contrast, the $OPVEBox·4PF_6$ superstructure reveals (FIG. 10) that the $OPVEBox^{4+}$ molecules crystallize in a herringbone fashion, stabilized by [π . . . π] stacking between pairs of $OPV^{2+}$ units, as well as there being [π . . . π] interaction between these $OPV^{2+}$ units and the p-phenylene rings in adjacent cyclophane molecules, with plane-to-plane distances of 2.7 and 3.9 Å, respectively. This observation indicates that merely changing counterions provides a way of modulating solid-state superstructures.

Formation of Diverse Ring-in-Ring(s) Complexes

Figure 2:
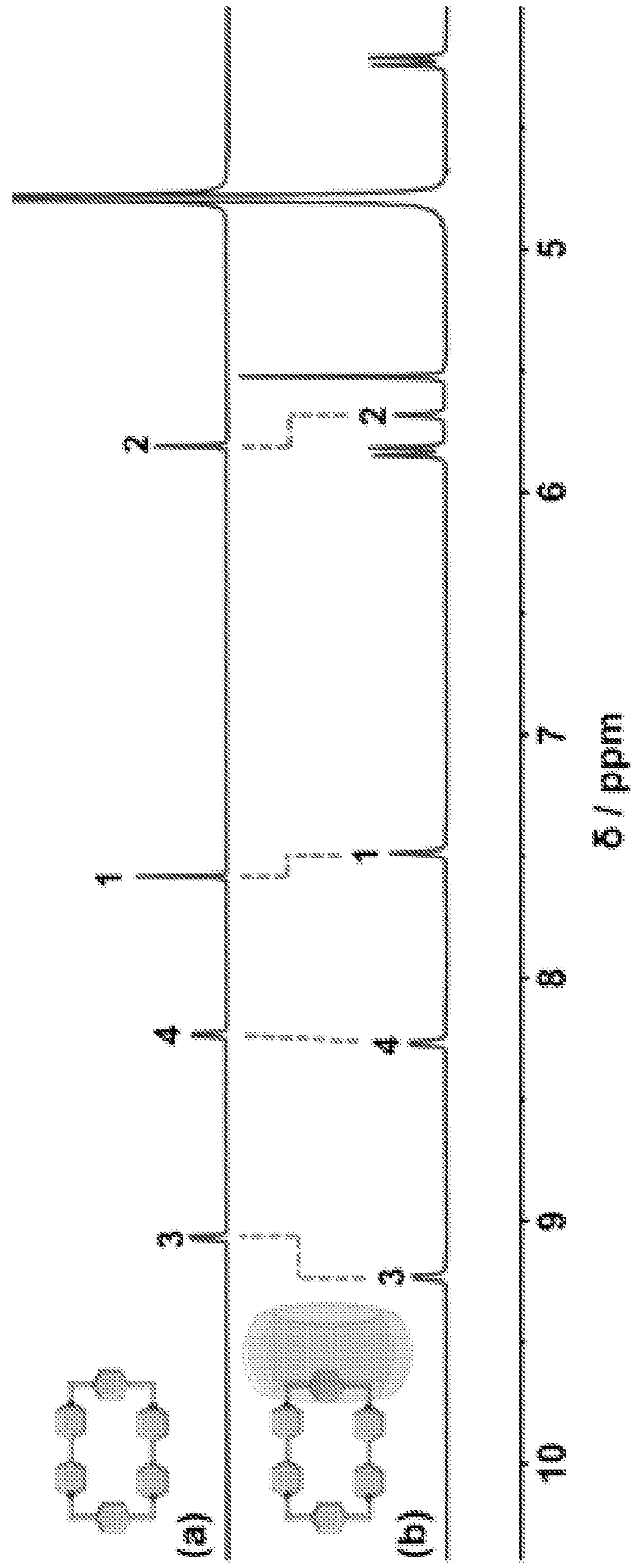
FIG. 2. $^1$H NMR Spectra (600 MHz, $D_2O$, 298 K) of (a) CBPQT·4Cl, and (b) CBPQT·4Cl with an equimolar amount of CB[8], (c) OPVEBox·4Cl, (d) the binary OPVEBox$^{4+}$ $\subset$ CB[8], and (e) the ternary OPVEBox$^{4+}$ $\subset$ 2CB[8] ring-in-ring(s) complexes.
Figure 2:
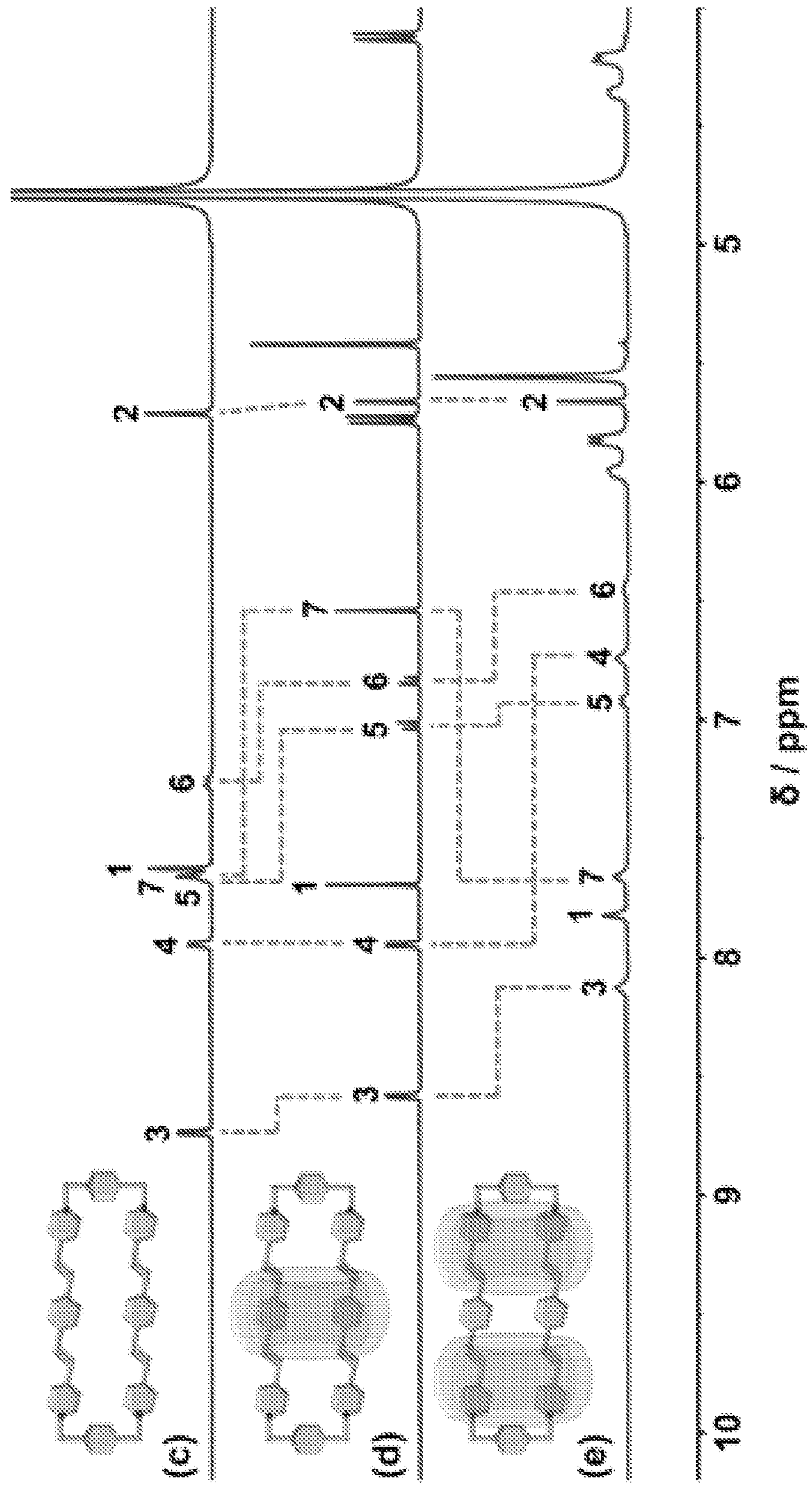

Upon adding an excess of CB[8] to an aqueous solution of OPVEBox·4Cl, the fluorescence of the solution changed from sky-blue to yellow, indicating the occurrence of non-covalent bonding interactions between CB[8] and $OPVEBox^{4+}$. $^1$H NMR spectroscopy and MS analyses were carried out in order to gain further insight into the nature of these interactions. Upon adding an equimolar amount of CB[8] to a $D_2O$ solution of OPVEBox·4Cl, the chemical shifts for protons in both the $OPVEBox^{4+}$ and CB[8] all show (FIGS. 2*d* and 7) marked changes in the $^1$H NMR spectrum, indicating the formation of a host-guest complex. The peaks in the spectrum were assigned on the basis of in-depth analyses of their 2D $^1$H-$^1$H COSY and ROESY spectra. The chemical shifts of H-7, residing on the central phenylene groups, as well as H-5 and H-6, attached to the C═C double bonds, show (FIG. 2*d*) large upfield shifts (Δδ=−0.64, −0.43 and −1.12 for H-5, H-6, and H-7, respectively). While the protons on CB[8] display (FIG. 7) small upfield shifts (Δδ=−0.09, −0.11 and −0.13 for H-a, H-b, and H-c, respectively). These results indicate that CB[8] is bound in the middle of $OPVEBox^{4+}$, forming a 1:1 ring-in-ring complex. In the 1H NMR spectrum (FIG. 2*b*) of an equimolar mixture of CBPQT4+ and CB[8], the chemical shift of H-4 shows no change, while protons associated with the p-xylylene linkers in $CBPQT^{4+}$ exhibit small upfield shifts (Δδ=−0.10 and −0.13 for H-1 and H-2, respectively). Hence, CB[8] may bind very weakly to the p-xylylene linkers, instead of forming ring-in-ring complex with CBPQT4+. Taken together, it can be concluded that, although $OPVEBox^{4+}$ and $CBPQT^{4+}$ have the same p-xylylene linkers, only $OPVEBox^{4+}$ can form ring-in-ring(s) complexes with CB[8] in aqueous solutions. A possible reasons for this observation is that the long $OPV^{2+}$ building blocks in $OPVEBox^{4+}$ is much more flexible than the $BIPY^{2+}$ units in $CBPQT^{4+}$.

Figure 3:
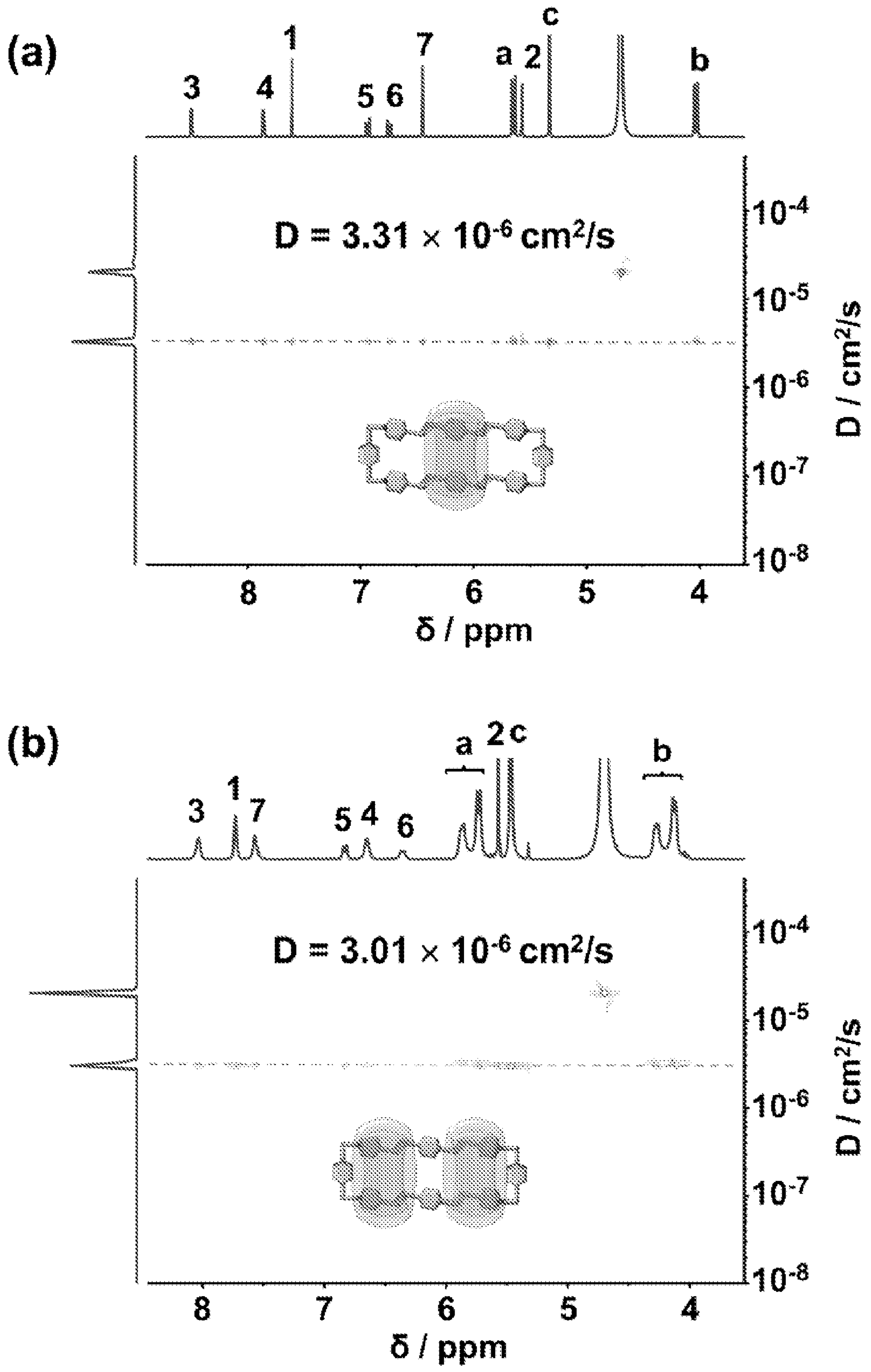
FIG. 3. 2D DOSY Spectra (600 MHz, $D_2O$, 298 K) of (a) binary OPVEBox$^{4+}$ $\subset$ CB[8] and (b) ternary OPVEBox$^{4+}$ $\subset$ 2CB[8] ring-in-ring(s) complexes. Electrospray ionization-mass spectra (ESI-MS) of (c) binary OPVEBox$^{4+}$ $\subset$ CB[8] and (d) ternary OPVEBox$^{4+}$ $\subset$ 2CB[8] ring-in-ring(s) complexes. The inset in ESI-MS represents the theoretical and experimental isotope patterns for the 4+ charge states of the binary and ternary ring-in-ring(s) complexes. The brown "4+" represents the four positively charged state of the OPVEBox$^{4+}$⊂CB[8] complex, while the blue "4+, 5+, 6+" represent the four, five, six positively charged states of the OPVEBox$^{4+}$⊂2CB[8] complex, accompanied by additions of differing numbers of $Na^+$ ions.
Figure 3:
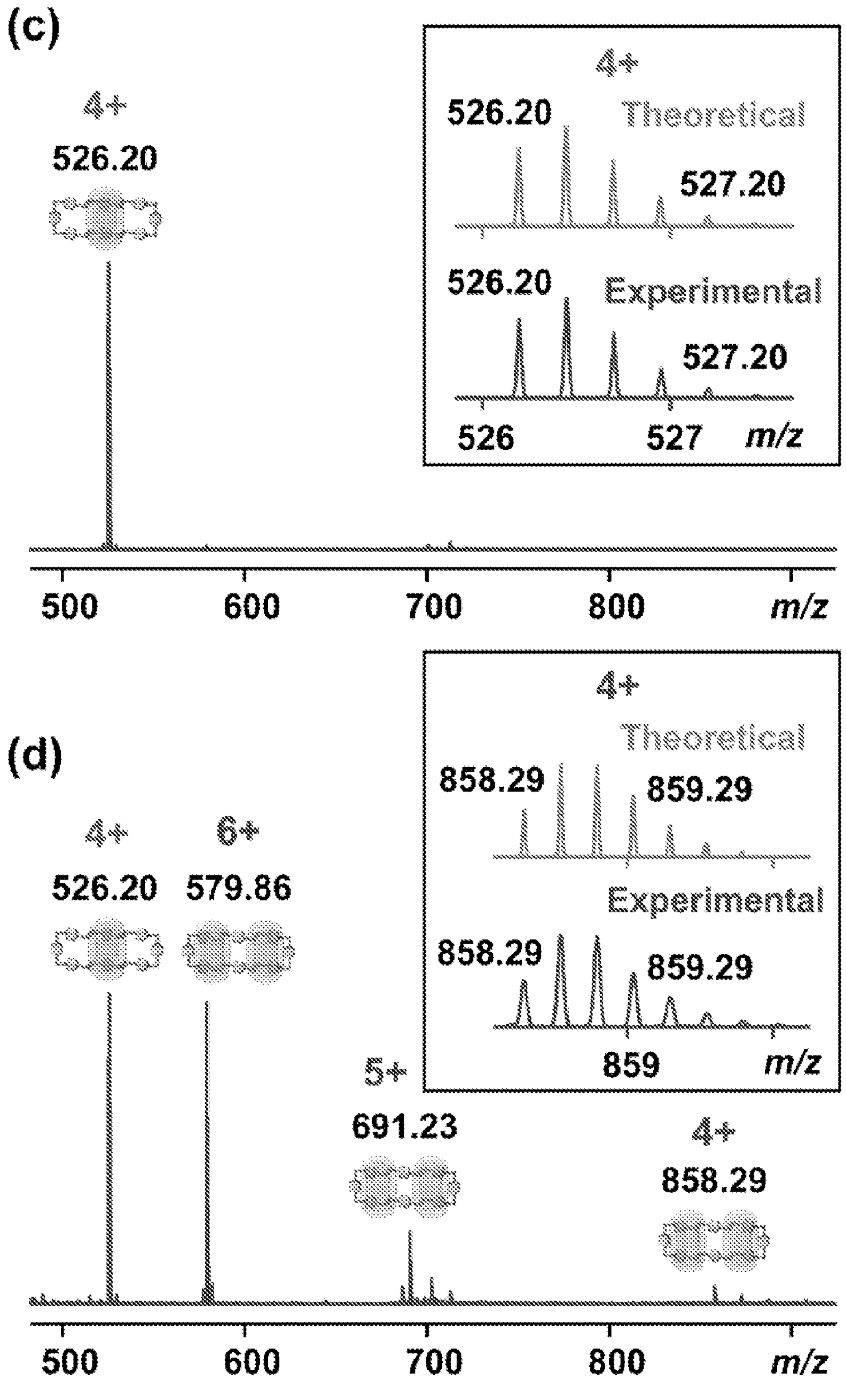

Upon the addition of another 1 equiv of CB[8] to a $D_2O$ solution of OPVEBox·4Cl⊂CB[8], a new set of resonances, accompanied by severely broadened, appeared (FIG. 2*e*) in the $^1$H NMR spectrum. On analysis of the 2D $^1$H-$^1$H COSY and ROESY spectra, all the peaks in the spectra could be assigned. Diagnostic changes in chemical shifts, on comparing (FIG. 8) with the 1H NMR spectra of free $OPVEBox^{4+}$ and CB[8], indicate the formation of a 1:2 ternary ring-in-rings complex, $OPVEBox^{4+}$⊂2CB[8]. All the protons residing on the pyridinium units and C═C double bonds display (FIG. 2*e*) large upfield shifts (Δδ=−0.61, −1.20, −0.75 and −0.81 for H-3, H-4, H-5, and H-6, respectively), while the chemical shift of H-7 does not change. The methylene protons (H-a and H-b) on CB[8] were separated (FIG. 8) into two sets of peaks (δ=5.96/5.82 and 4.36/4.22 for H-a and H-b, respectively), indicating that the centrosymmetric geometry of CB[8] molecules has been broken. All these results reveal that two CB[8] molecules are bound to the pairs of pyridinium units and C═C double bonds at both ends of the extended cyclophane in the ternary $OPVEBox^{4+}$⊂2CB[8] ring-in-rings complex. On continuing to add CB[8] into the $D_2O$ solution of OPVEBox·4Cl⊂2CB[8], the chemical shifts of both host and guest protons showed (FIG. 9) no appreciable changes. This observation suggests that the 1:2 complex is thermodynamically stable, despite the presence of an excess of CB[8]. 2D Diffusion-ordered NMR spectroscopy (DOSY) confirmed the formation of the binary and ternary ring-in-ring(s) complexes. The spectra of $OPVEBox^{4+}$, $OPVEBox^{4+}$⊂CB[8] (FIG. 3*a*), and $OPVEBox^{4+}$⊂2CB[8] (FIG. 3*b*) display narrow signal bands with diffusion coefficients of $3.94\times10^{-6}$, $3.31\times10^{-6}$, and $3.01\times10^{-6}$ $cm^2/s$, respectively. Furthermore, $^1$H NMR titrations revealed (FIG. 9) that the association and disassociation of both $OPVEBox^{4+}$⊂CB[8] and $OPVEBox^{4+}$⊂2CB[8] complexes undergo slow exchange on the $^1$H NMR time scale.

In addition, ESI-MS provided strong evidence for the formation of these two ring-in-ring(s) superstructures. In the ESI-MS of an equimolar mixture of OPVEBox·4Cl and CB[8], only one peak (m/z=526.20) is present (FIG. 3*c*), corresponding to the 1:1 complex with four positive charges, namely, $[OPVEBox^{4+}⊂CB[8]]^{4+}$. Upon further addition of CB[8] to the solution of $OPVEBox^{4+}$⊂CB[8], a series of new peaks appears (FIG. 3*d*) in the ESI-MS, as a result of the formation of the 1:2 $OPVEBox^{4+}$⊂2CB[8] ring-in-rings complex, accompanied by the additions of differing numbers of $Na^+$ ions. The isotopic patterns (FIG. 3*d*) with four, five, and six positive charges at m/z=858.29 ($[OPVEBox^{4+}$⊂2CB[8]4+), 691.23 ($[OPVEBox^{4+}⊂2CB[8]+Na^+]^{5+}$), and 579.86 ($[OPVEBox^{4+}⊂2CB[8]+2Na^+]^{6+}$), respectively, match well with their theoretical values, strongly supporting the formation of the ternary ring-in-rings complex. Based on the NMR spectroscopic and ESI-MS experiments, it is can be concluded that two kinds of new ring-in-ring(s) complexes can be assembled by simply mixing the tetracationic cyclophane $OPVEBox^{4+}$ with 1 or 2 equiv of CB[8] in aqueous solution.

DFT Calculations

Figure 4:
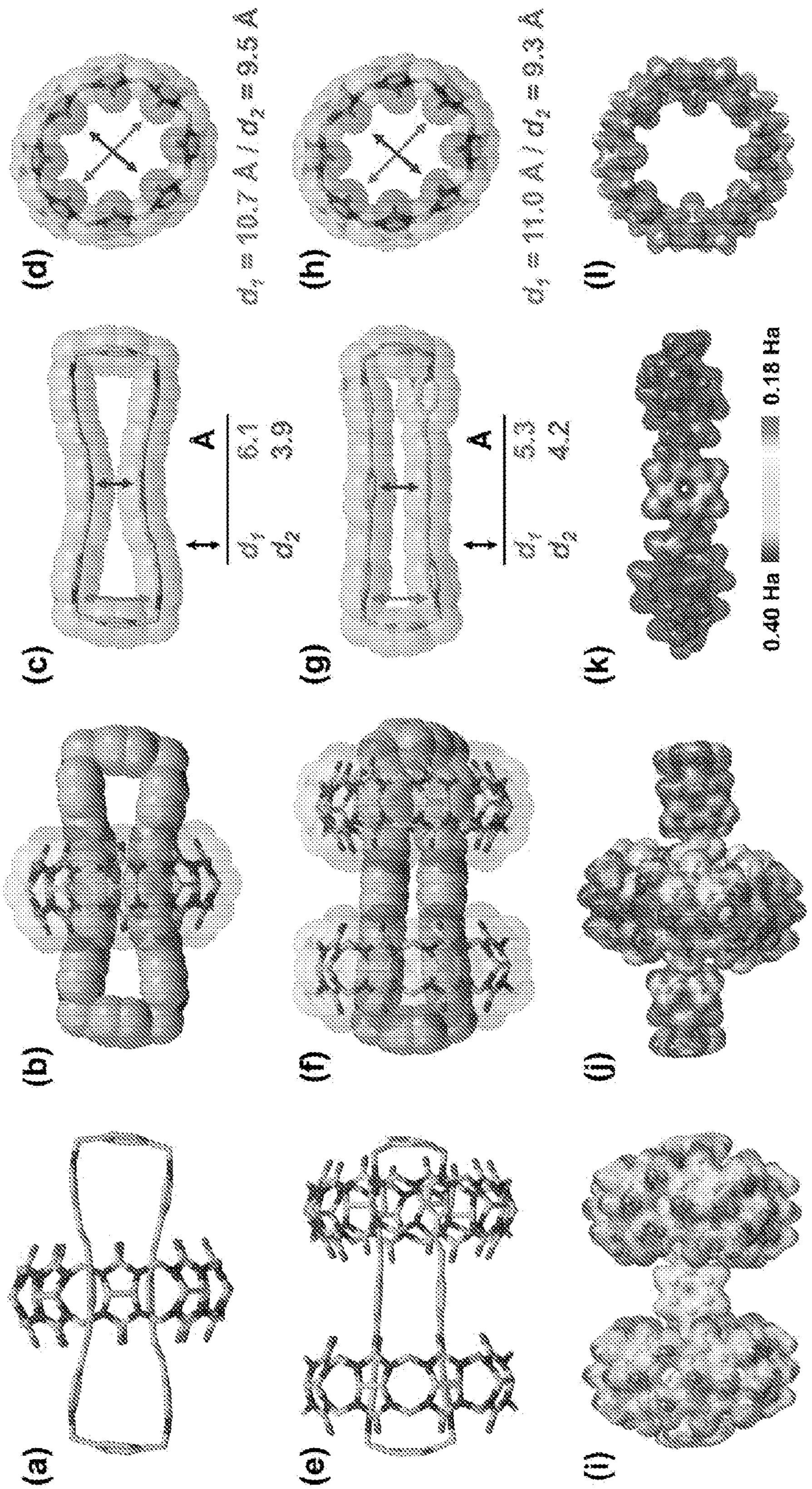
FIG. 4. (a-b) Capped-stick and space-filling representations of the optimized superstructure of the binary OPVEBox$^{4+}$⊂CB[8] complex determined by DFT calculations. (c-d) The structures of individual OPVEBox$^{4+}$ and CB[8] in the binary complex, showing the characteristic distances defining their geometries. (e-f) Capped-stick and space-filling representations of the optimized superstructure of the ternary OPVEBox$^{4+}$⊂2CB[8] complex determined by DFT calculations. (g-h) The structures of individual OPVEBox$^{4+}$ and CB[8] in the ternary complex, showing the characteristic distances defining their geometries. (i-l) Electrostatic potential maps of the ternary OPVEBox$^{4+}$⊂2CB[8] and binary OPVEBox$^{4+}$⊂CB[8] ring-in-ring(s) complexes, as well as the free OPVEBox$^{4+}$ and CB[8], respectively. Red and deep-blue colors in the maps represent negative and positive electrostatic potentials, respectively.

In order to gain a better understanding of the superstructures and electronic properties of both the binary $OPVEBox^{4+}$⊂CB[8] and ternary $OPVEBox^{4+}$⊂2CB[8] ring-in-ring(s) complexes, density functional theory (DFT) calculations were performed. The optimized superstructure of $OPVEBox^{4+}$⊂CB[8] was determined to be (FIGS. 4 and 30) such that the central phenylene groups and C═C double bonds are included inside the cavity of CB[8], in accordance with the results obtained from $^1$H NMR spectroscopy. The $OPVEBox^{4+}$ no longer adopts a box-like conformation in the optimized superstructure (FIG. 4*c*) of $OPVEBox^{4+}$⊂CB[8], wherein the $OPV^{2+}$ units are compelled to bend into the cavity of the cyclophane with the centroid-to-centroid distance being reduced to 3.9 Å, on account of the tight encapsulation by the CB[8] ring. The strain energy (Table 6) for the compressed $OPVEBox^{4+}$ in this ring-in-ring complex is 28.6 kcal/mol according to DFT calculations. In the case of $OPVEBox^{4+}$⊂2CB[8] complex, two CB[8] are bound (FIGS. 4 and 31) to the two sides of $OPVEBox^{4+}$, which is also in agreement with the $^1$H NMR spectroscopic results. As a consequence of the compression by the two CB[8]

rings, the entire $OPVEBox^{4+}$ is squeezed, and its strain energy is (Table 6) 42.9 kcal/mol, a value which is higher than that (28.6 kcal/mol) present in the binary ring-in-ring complex. The p-xylylene linkers are forced to bend, with the distance (FIG. 4*g*) between their two peripheral nitrogen atoms of 5.3 Å. Meanwhile, the CB[8] rings assume (FIGS. 4*d* and 4*h*) an ellipsoidal deformation in order to form the ring-in-ring(s) complexes. According to the electrostatic potential analysis, after complexing with one and two CB[8] rings, the electronic cloud density in the original electron deficient $OPVEBox^{4+}$ cyclophane increases gradually (FIGS. 4*i-k*) as a result of intermolecular charge transfer.

UV-Vis Absorption Spectroscopy

Figure 5:
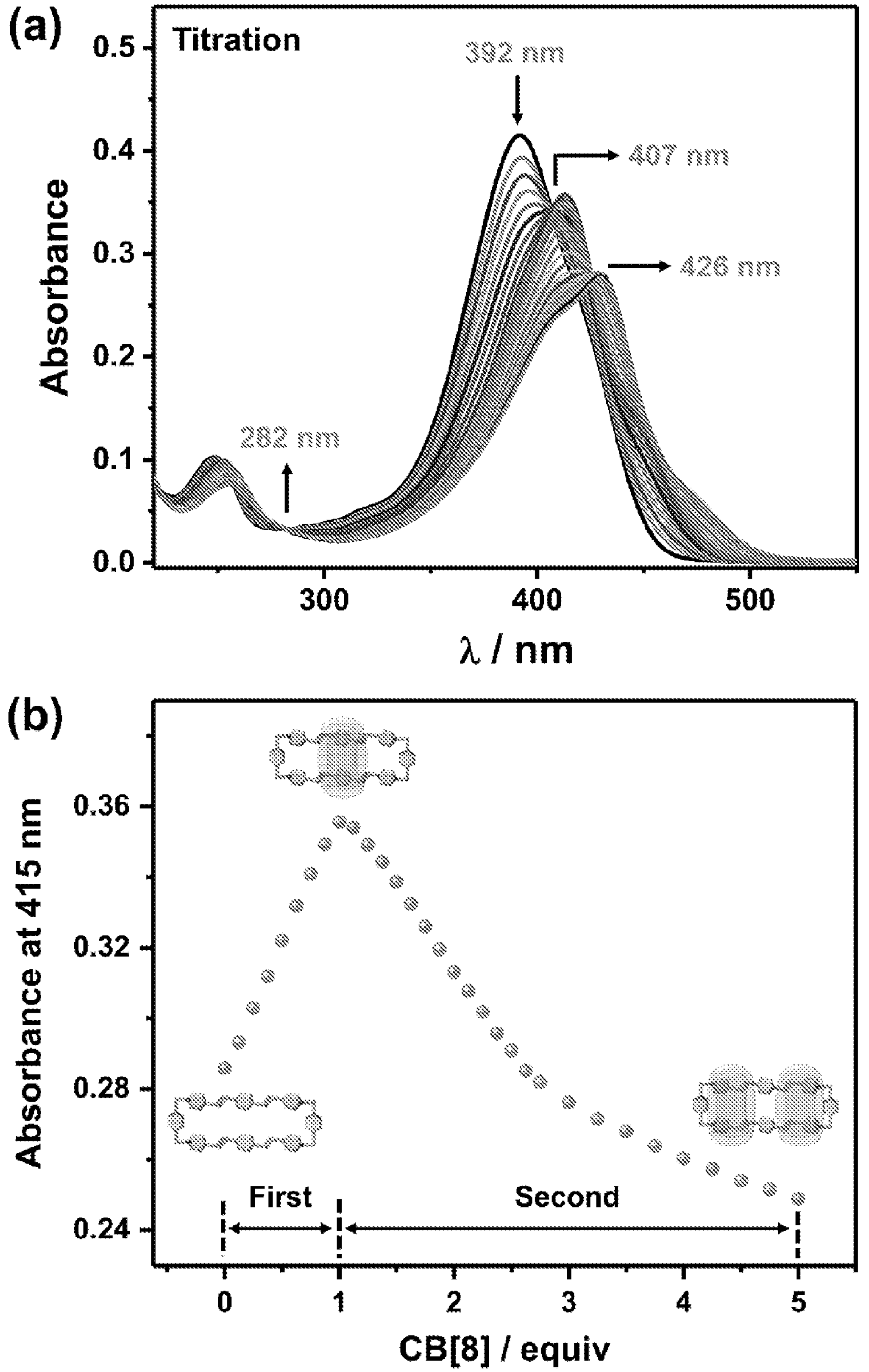
FIG. 5. (a) UV-Vis Absorption spectra ([OPVEBox·4Cl] =4 μM, [CB[8]]=0-20 μM, $H_2O$, 298 K) and (b) absorbance intensity changes at 415 nm of OPVEBox·4Cl upon gradual addition of CB[8] in an aqueous solution.
Figure 16:
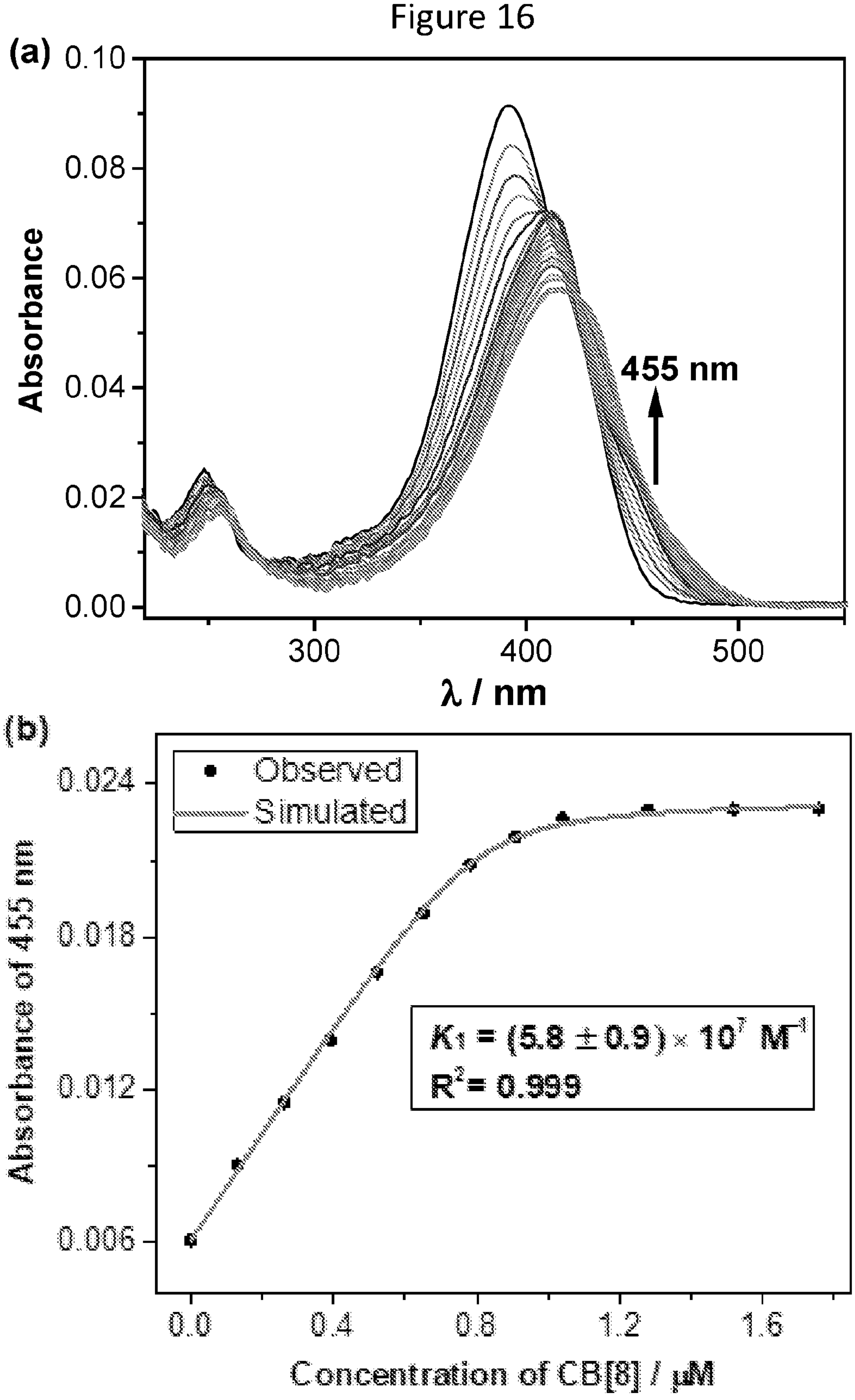
FIG. 16. (a) UV-Vis Titration experiment ([OPVEBox·$^{4+}$] =0.8 μM, [CB[8]]=0-1.76 μM, $H_2O$, 298 K) on adding CB[8] to a aqueous solution of OPVEBox$^{4+}$ at 298 K. (b) Nonlinear least-squares analysis of the absorbance intensity changes at 455 nm in the UV-Vis titration experiment as shown in (a), the first-stage binding constant ($K_1$) was determined to be 5.8×10$^7$ M$^{-1}$.

The changes in the absorption spectra induced by the formation of the ring-in-ring(s) complexes provide for a way to track molecular recognition processes. In a UV-Vis titration (FIG. 5*a*), the absorbance at 415 nm increases (FIG. 5*b*) gradually with the stepwise addition of 1 equiv of CB[8] to an aqueous solution of OPVEBox·4Cl. On the contrary, the absorbance shows a downward trend when continuing to add another 4 equiv of CB[8]. These observations indicate there is a two-stage binding process happening during titration of $OPVEBox^{4+}$ with CB[8]. In the first stage of the stepwise addition of 1 equiv of CB[8] to an aqueous solution of OPVEBox·4Cl, the absorption peak of $OPVEBox^{4+}$, centered on 392 nm, decreases (FIG. 16) gradually with a red shift of 21 nm. Also, two clear isosbestic points appear (FIG. 5*a*) at 282 and 407 nm in the UV-Vis spectra. These observations reflect the formation of the binary $OPVEBox^{4+} \subset CB[8]$ ring-in-ring complex. In the second stage, upon the further addition of 4 equiv of CB[8], the absorption peak intensity of $OPVEBox^{4+} \subset CB[8]$, centered on 413 nm, continues to decrease. The peak is red shifted to 430 nm (FIG. 14), accompanied by the appearance (FIG. 5*a*) of a new isobestic point at 426 nm. These changes are a result of the transformation from the binary $OPVEBox^{4+} \subset CB[8]$ to the ternary $OPVEBox^{4+} \subset 2CB[8]$ complexes. A Job plot shows (FIG. 13) a maximum at a molar fraction of 0.33, confirming the 1:2 stoichiometry between $OPVEBox^{4+}$ and CB[8].

Frontier molecular orbital calculations reveal the origin of the changes in photophysical properties upon the formation of these two complexes. The frontier molecular orbital diagrams show (FIGS. 36 and 37) that both the HOMOs and LUMOs of the ring-in-ring(s) complexes are localized predominantly on $OPVEBox^{4+}$. The HOMO-LUMO energy gaps (Table 4) for the $OPVEBox^{4+}$, $OPVEBox^{4+} \subset CB[8]$ and $OPVEBox^{4+} \subset 2CB[8]$ are 2.79, 2.61 and 2.55 eV, respectively, which become narrower upon binding one and then two CB[8] molecules. These gradually narrowing energy gaps are consistent with the red shift in the absorption spectra upon the encapsulation of $OPVEBox^{4+}$ by CB[8].

Binding Thermodynamics

Figure 15:
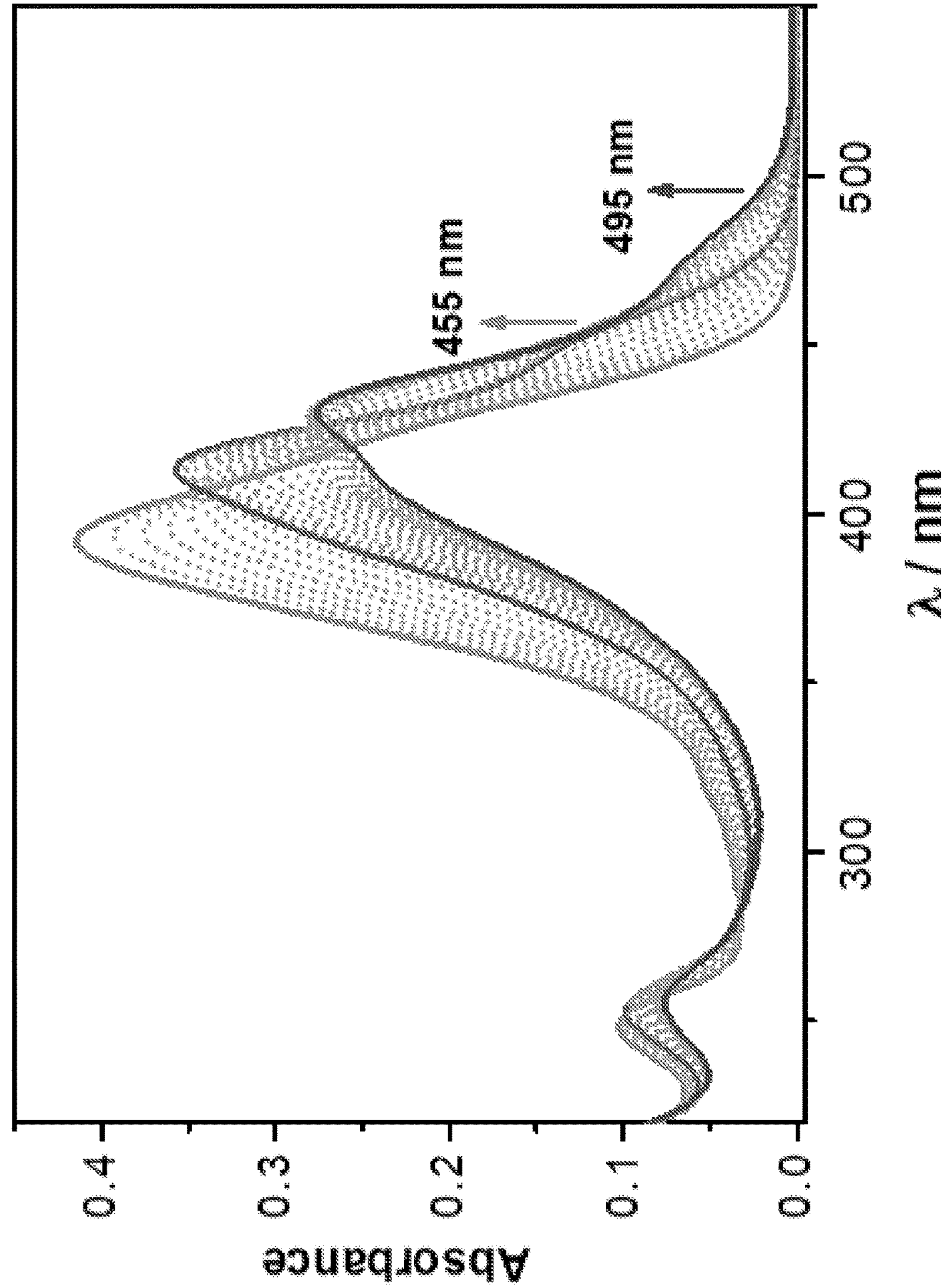
FIG. 15. UV-Vis Titration experiment ([OPVEBox·$^{4+}$]=4 μM, [CB[8]]=0-20 μM, $H_2O$, 298 K) on adding CB[8] to a aqueous solution of OPVEBox$^{4+}$ at 298 K. A typical two-stage bonding process is uncovered. First stage (red curves): the formation of binary OPVEBox$^{4+}$⊂CB[8] ring-in-ring complex upon the addition of 1 equiv of CB[8]. Second stage (blue curves): the ternary OPVEBox$^{4+}$⊂2CB[8] ring-in-rings complex formed gradually upon continue to add 4 equiv of CB[8].
Figure 17:
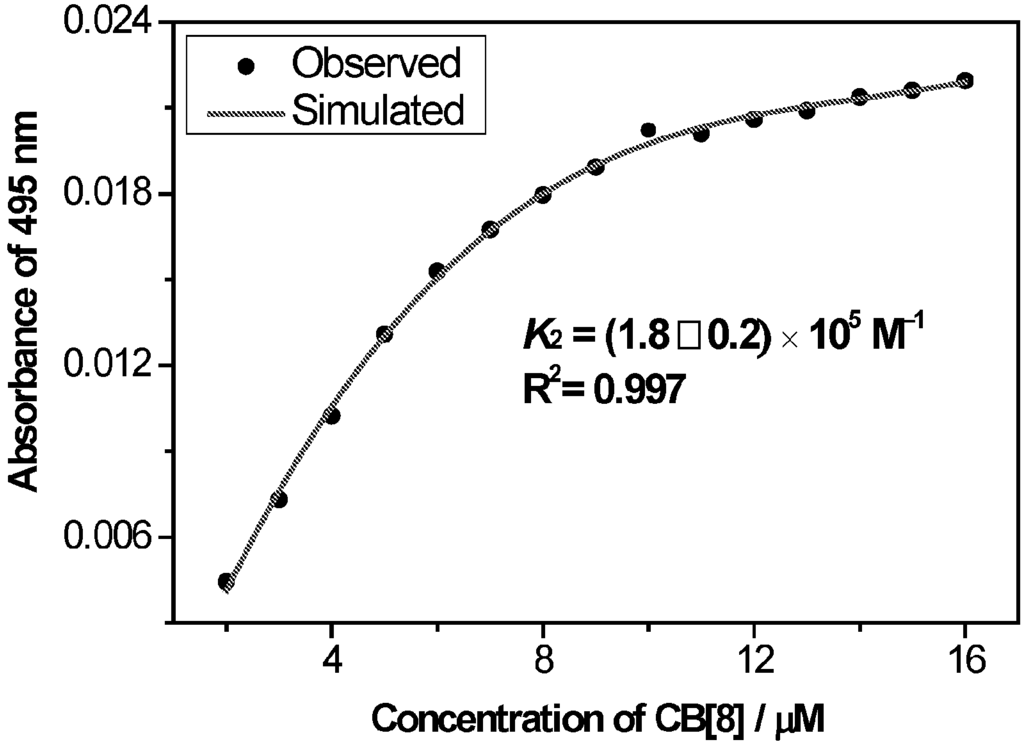
FIG. 17. Nonlinear least-squares analysis of the absorbance intensity changes at 495 nm in the UV-Vis titration experiment as shown in FIG. 15, in order to calculate the second-stage binding constant ($K_2$) for the formation of ternary OPVEBox$^{4+}$⊂2CB[8] ring-in-rings complex in aqueous solutions.

The binding constants for the formation of the binary and ternary ring-in-ring(s) complexes can be obtained from the UV-Vis titration spectroscopy and isothermal titration calorimetry (ITC). The absorption band in the range from 450 to 460 nm increases (FIG. 15) upon formation of the binary complex, while it shows almost no change during the formation of the ternary complex. Accordingly, the first-stage binding constant ($K_1$) for the formation of the binary $OPVEBox^{4+} \subset CB[8]$ complex has been determined (FIG. 16) to be $5.8\times10^7$ $M^{-1}$, based on the change in absorbance at 455 nm upon titrating $OPVEBox^{4+}$ with CB[8]. Although it is difficult to evaluate the $K_1$ using ITC, because of the low solubility of CB[8] in $H_2O$, the change of enthalpy (ΔH) was estimated (FIG. 25) to be −2.0 kcal/mol from the isotherm of a single injection experiment.[32] The Gibbs free energy (ΔG) was determined (Table 1) from the UV-Vis titration carried out at 25° C., and then the value of TΔS was calculated to be 8.6 kcal/mol. It follows that the formation of the $OPVEBox^{4+} \subset CB[8]$ complex in aqueous solution is driven mainly by a favorable entropy change with a small contribution from the change of enthalpy, indicating that this binding process is dominated by hydrophobic effect. When the binary $OPVEBox^{4+} \subset CB[8]$ complex is converted into the ternary $OPVEBox^{4+} \subset 2CB[8]$ complex during the second binding event, a new absorption peak appears (FIG. 15) at approximately 480 nm in the UV-Vis absorption spectra. Consequently, the second-stage binding constant (K2) was calculated (FIG. 17) to be $1.8\times10^5$ $M^{-1}$ by following the change in absorbance at 495 nm. The complex of $OPVEBox^{4+} \subset CB[8]$ has a high water solubility, allowing us to perform ITC experiment for the second-stage binding by titrating $OPVEBox^{4+} \subset CB[8]$ complex into a dilute aqueous solution of CB[8]. A value of $K_2$ was determined (FIG. 24) to be $1.5\times10^5$ $M^{-1}$, which is matched well with that ($1.8\times10^5$ $M^{-1}$) estimated from the UV-Vis titration. The change of enthalpy (ΔH) was determined to be −11.8 kcal/mol and the TΔS was calculated to be −4.7 kcal/mol for the second stage binding event, indicating that the formation of the $OPVEBox^{4+} \subset 2CB[8]$ complex is enthalpically driven. It is clear that the formation of the 1:2 complex involves a more favorable binding enthalpy (−11.8 kcal/mol) than that (−2.0 kcal/mol) associated with the formation of the 1:1 complex. This difference might be a result of multiple [$N^+$ . . . O═C] ion-dipole interactions in the 1:2 complex, while the [$N^+$ . . . O═C] ion-dipole interactions are negligible when CB[8] is located in the middle of $OPVEBox^{4+}$ in the case of the 1:1 complex.

TABLE 1

Overview of Thermodynamic Date for Ring-in Ring Complexes at 298K[a]

| | Ka ($M^{-1}$) | | ΔG | ΔH | TΔS | ΔS |
|---|---|---|---|---|---|---|
| Stages | UV-Vis | ITC | (kcal/mol) | | | (cal/mol K) |
| First Stage | $5.8\times10^7$ | ND[b] | −10.6[c] | −2.0 | 8.6 | 28.9 |
| Second Stage | $1.8\times10^5$ | $1.5\times10^5$ | −7.1[d] | −11.8 | −4.7 | −15.8 |

[a]Standard error is presented in Supporting Information.
[b]Not determined.
[c]Estimated from UV-Vis titrations.
[d]Directly determined by ITC.

Multicolor Fluorescent Outputs

Figure 6:
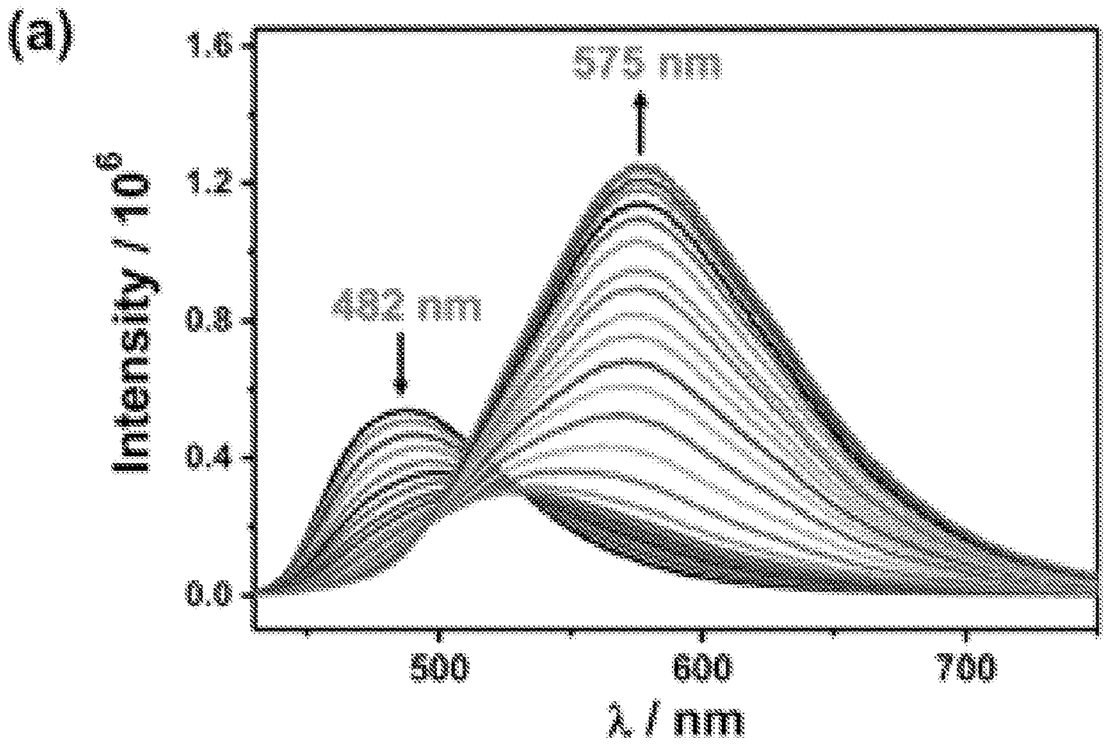
FIG. 6. (a) Fluorometric titration and (b) Fluorescence intensity changes at 482 and 575 nm, when continuing to add CB[8] to an aqueous solution of OPVEBox·4Cl ([OPVEBox·4Cl]= 2 μM, [CB[8]]=0-11.6 μM, λex=392 nm, $H_2O$, 298 K). (c) The 1931 CIE chromaticity diagram illustrating the luminescent color changes of OPVEBox·4Cl with the continuous addition of CB[8], corresponding to (a). (d) Emission spectra recording the spectral changes for OPVEBox·4Cl ([OPVEBox·4Cl]=2 [CB[8]]=0-3 equiv., λex=392 nm, $H_2O$, 298 K) upon addition of different equiv of CB[8] in an aqueous solution. (e) Fluorescent photographs showing the visual changes in luminescent color of OPVEBox·4Cl with addition of increasing equivalents of CB[8] in aqueous solution.
Figure 6:
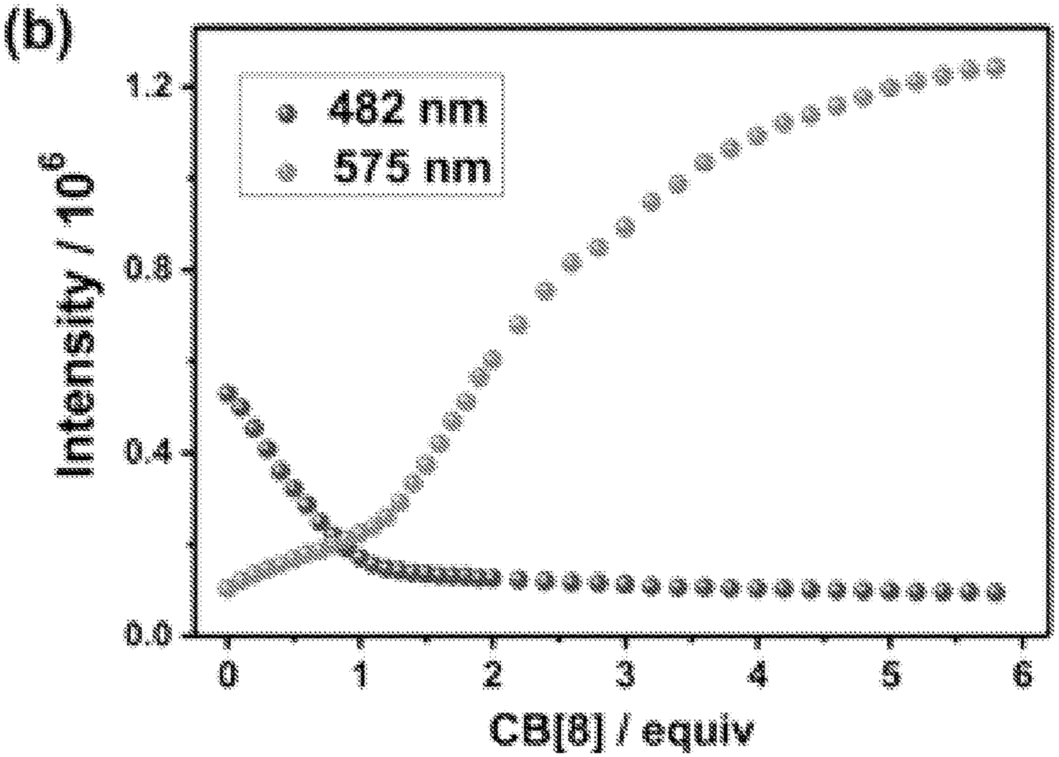
Figure 6:
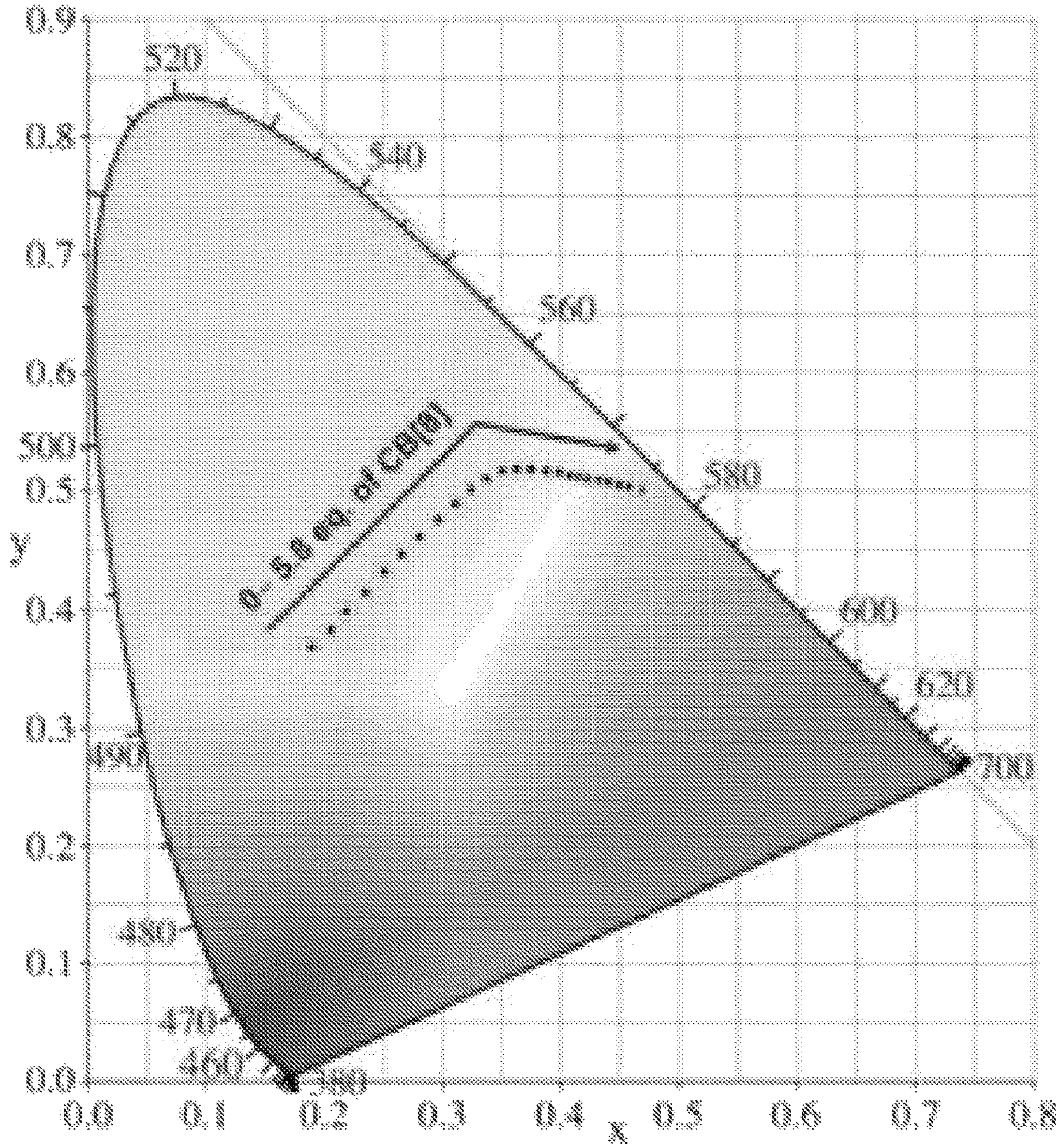
Figure 6:
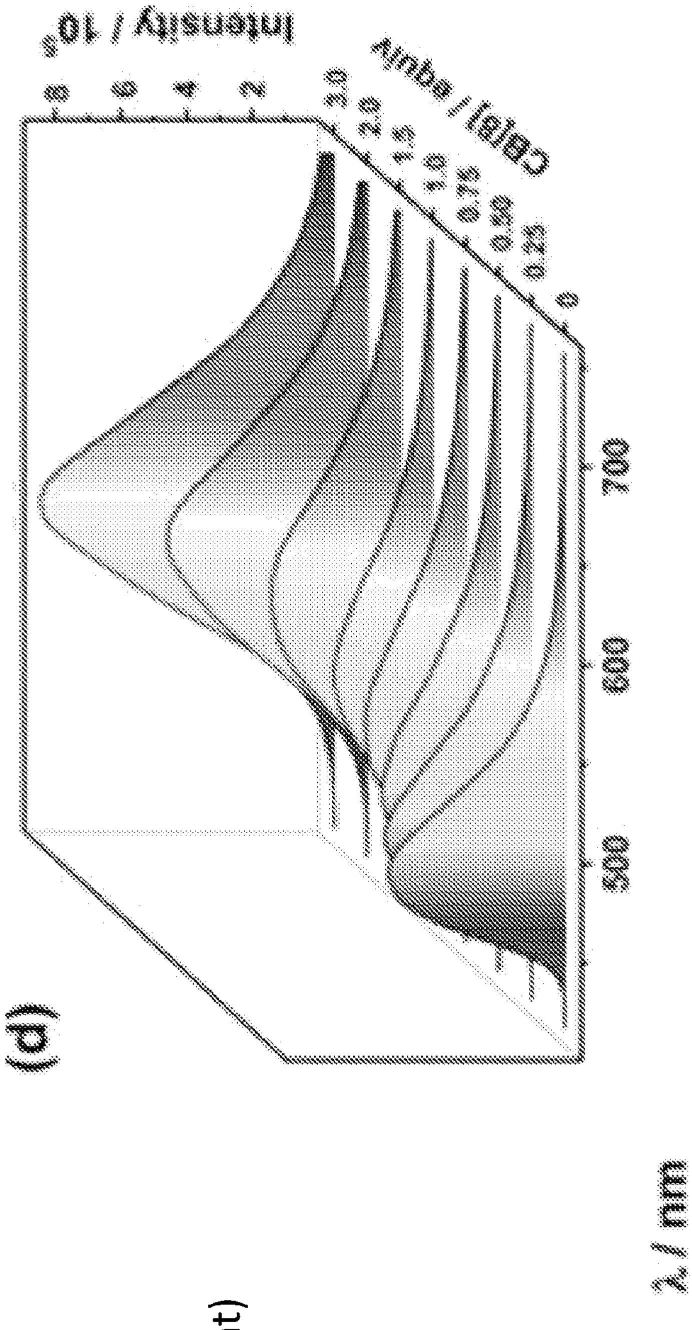
Figure 6:
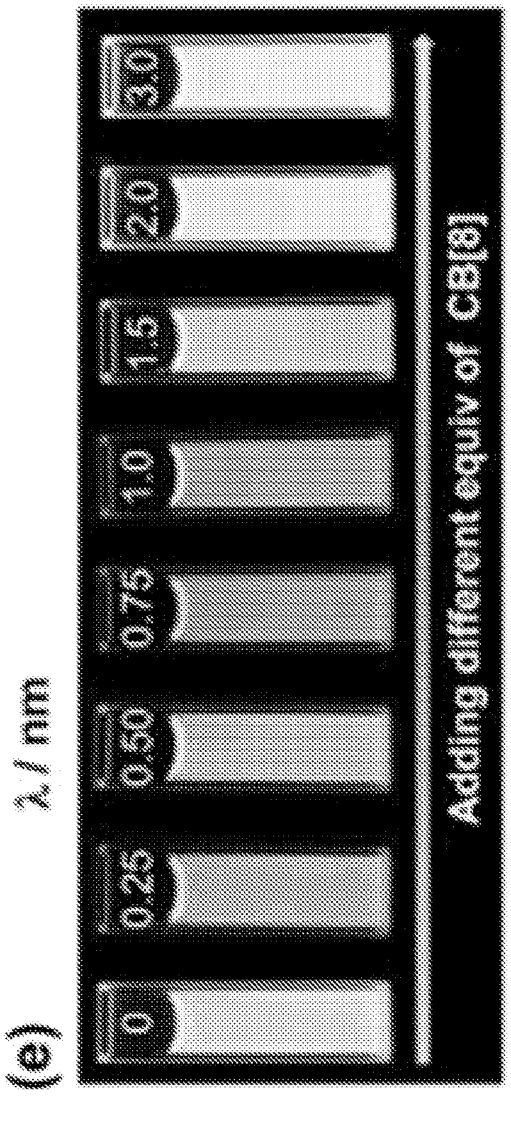
Figure 20:
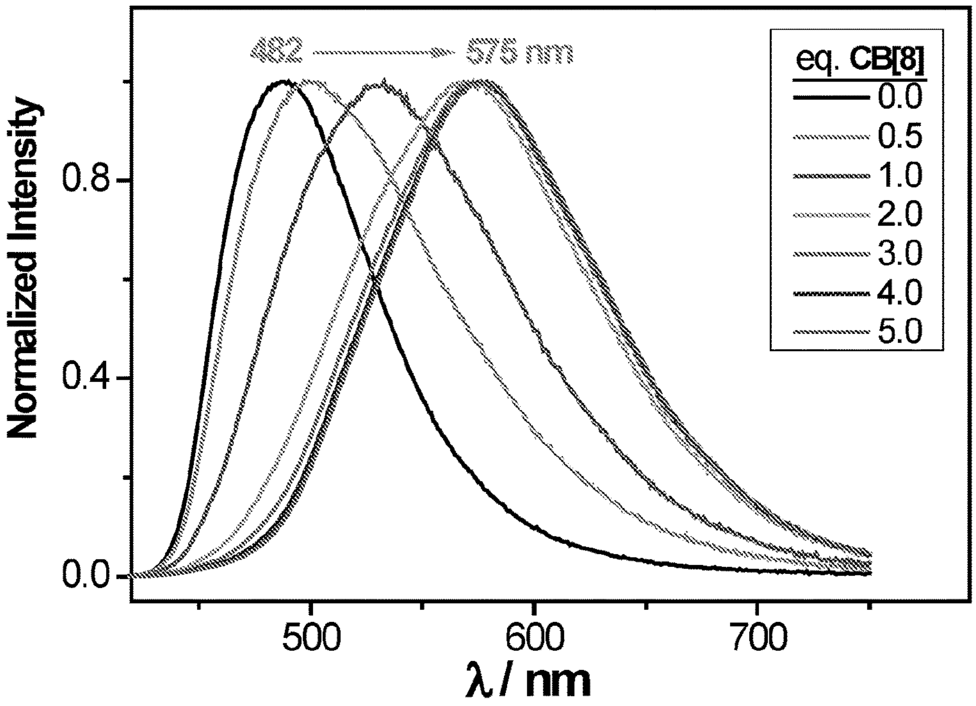
FIG. 20. Normalized emission spectra ([$OPVEBox\cdot^{4+}$]=2 μM, [CB[8]]=0-10 μM, λex=392 nm, $H_2O$, 298 K) of $OPVEBox^{4+}$ with adding different equiv of CB[8]. The maximum emission wavelength red shifted from 482 to 575 nm.
Figure 22:
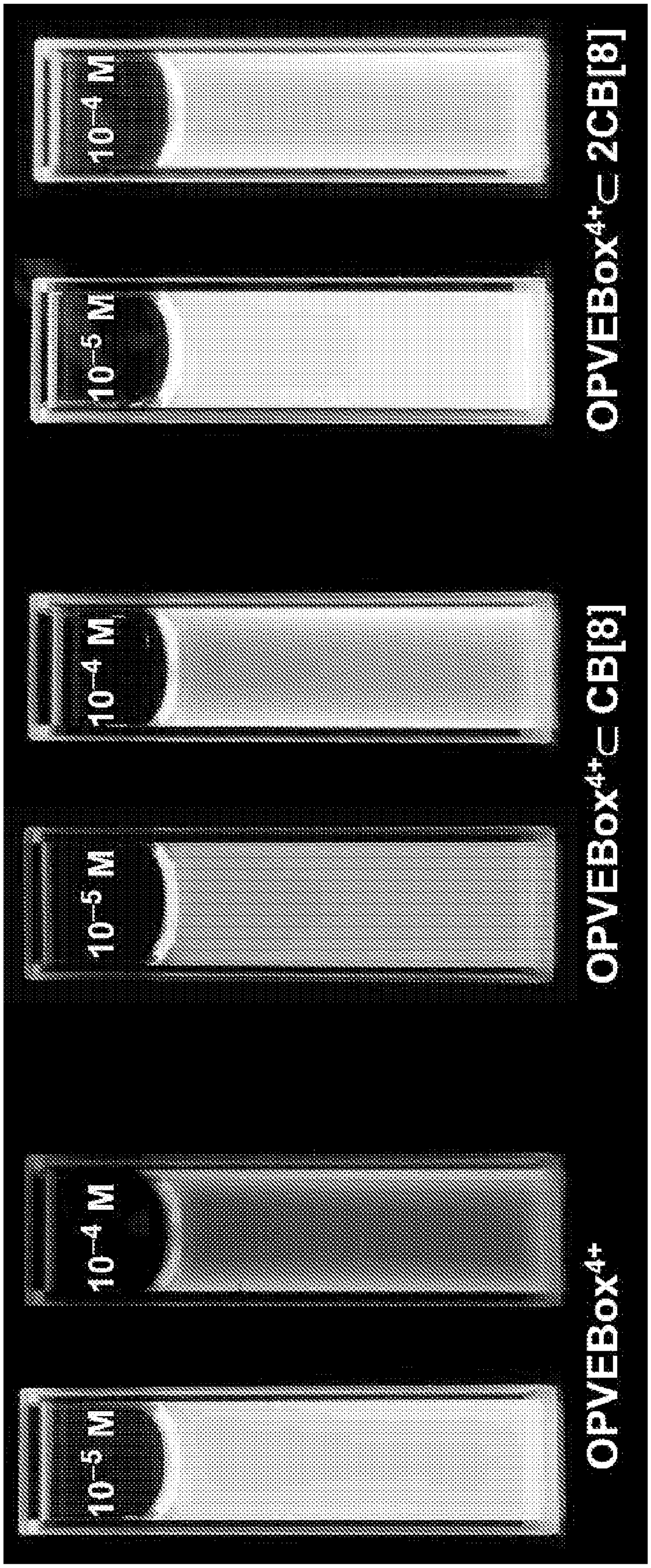
Figure 23:
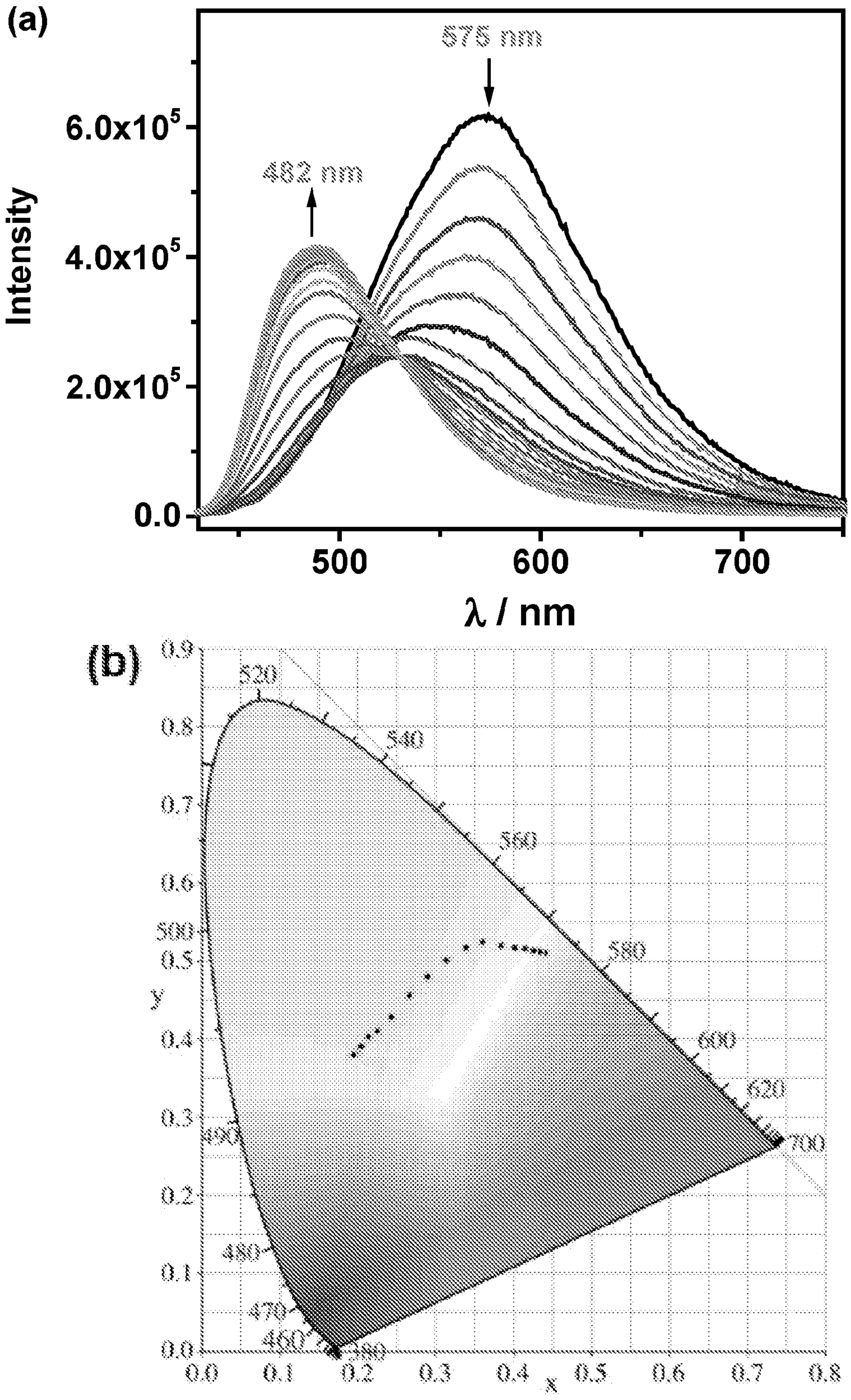
FIG. 23. (a) Emission spectra recorded during the continuous addition of memantine hydrochloride (Mem) to an aqueous solution of OPVEBox·4Cl$\subset$2CB[8] ring-in-rings complex ([OPVEBox·4Cl]=2 μM, [CB[8]]=41.1M, [Mem]=0-6 μM, λex=392 nm, $H_2O$, 298 K). (b) The 1931 CIE chromaticity diagram illustrating the luminescent color changes, with the continuous addition of Mem to an aqueous solution of the ternary ring-in-rings complex corresponding to (a).

During the formation of the binary $OPVEBox^{4+} \subset CB[8]$ and ternary $OPVEBox^{4+} \subset 2CB[8]$ ring-in-ring(s) complexes, tunable fluorescent emissions ranging from sky-blue to bright yellow are observed. Upon adding an equimolar amount of CB[8] to a 2 μM aqueous solution of OPVEBox·4Cl, the fluorescence intensity of $OPVEBox^{4+}$ decreases (FIG. 6*a*) and the maximum emission wavelength is red shifted (FIG. 20) from 482 to 533 nm, as a result of the formation of the 1:1 complex. The fluorescence quantum yield of $OPVEBox^{4+} \subset CB[8]$ is measured (Table 2) to be 2.4%, a value which is the same as that (2.4%) for the free $OPVEBox^{4+}$. By contrast, when continuing to add 1 equiv of CB[8] to the solution of 1:1 complex, the fluorescence intensity increases (FIG. 6*a*) and the maximum emission wavelength shifts to 575 nm, which is red shifted by 93 nm compared with that (482 nm) of free OPVEBox$^{4+}$. The fluorescence quantum yield reaches (Table 2) 8.1%, on account of the formation of the OPVEBox$^{4+}$⊂2CB[8] complex. With increasing concentration of CB[8] from 2 to 5 equiv, the fluorescence intensity of the resulting solution shows (FIG. 6*a*) an upward trend, although the peaks are no longer red shifted (FIG. 20), and a higher fluorescence quantum yield of 18.6% is obtained (Table 2). These results are attributable to the larger proportion of the ternary OPVEBox$^{4+}$⊂2CB[8] complex in the resulting aqueous solution with increasing concentration of CB[8]. Upon complexing with 1 and 2 equiv CB[8], the average fluorescence lifetimes (Table 3) of OPVEBox$^{4+}$ increases from 0.3 ns to 6.0 and 12.0 ns, respectively, indicating that CB[8] is able to stabilize the excited states of OPVEBox$^{4+}$. In a higher-concentration solution of OPVEBox$^{4+}$ (10 μM) and CB[8] (50 μM), the fluorescence quantum yield (Table 2) reaches 30.0%, and the proportion of the long fluorescence-lifetimes (12.0 ns) species, arising from the OPVEBox$^{4+}$⊂2CB[8] complex, is 95%. These observations may be the result of the association and dissociation equilibrium shifting to produce larger amounts of the ternary complex at higher concentration according to Le Chatelier's principles.[33] The higher fluorescence quantum yields maybe benefit from the fact that CB[8] molecules restrict the free pedal motion about the C═C double bonds within OPVEBox$^{4+}$. Both binary and ternary ring-in-ring(s) complexes exhibit (FIG. 22) bright fluorescence even at concentrations of 0.1 mM in aqueous solutions, an observation which demonstrates that the photoluminescence properties of the ring-in-ring(s) complexes persist over a wide range of concentrations. In addition, upon the stepwise addition of CB[8] to an aqueous solution of OPVEBox·4Cl, the resulting mixtures show multicolor fluorescent outputs. All of the luminescent color coordinates, which have been calculated and plotted (FIG. 6*c*) in the CIE 1931 chromaticity diagram, demonstrate that the fluorescent color changes from sky-blue to bright yellow with the addition of 0-5.8 equiv of CB[8] to an solution of OPVEBox·4Cl. The fluorescent conversion process can also be detected by the naked eye. Aqueous solutions of OPVEBox·4Cl with different equivalents of CB[8] exhibit (FIG. 6*e*) remarkable colorful emission capacities, e.g., sky-blue, cyan, green, yellow and gold. These observations signify that the encapsulation of OPVEBox$^{4+}$ by CB[8], not only improves significantly the luminescent properties of tetracationic cyclophane by endowing it with higher quantum yield and a longer lifetime, but also realizes multicolor fluorescent outputs from a single fluorophore in aqueous solution. Because of the strong binding affinity[34] ($K_a$=8.3×$10^{12}$ $M^{-1}$) of memantine hydrochloride (Mem) for CB[8], it is possible to investigate the dissociative behavior of the ring-in-ring(s) complexes by exploiting Mem as a competitive guest. Upon the stepwise addition of Mem to an aqueous solution of the OPVEBox·4Cl⊂2CB[8] ring-in-rings complex, the fluorescence intensity at 575 nm decreased (FIG. 23*a*) gradually, while the maximum emission wavelength was blue shifted to 482 nm, owing to the breakup of the ring-in-ring(s) complexes, affording the free OPVEBox$^{4+}$. Also, the fluorescent color changes (FIG. 23*b*) from yellow back to sky-blue. These results demonstrate that the emission colors can be tuned reversibly by adding a competitive guest.

Summary

A semi-rigid tetracationic cyclophane, OPVEBox$^{4+}$, which has been designed and synthesized, is able to serve as a guest instead of as a host, forming two ring-in-ring(s) complexes with CB[8] molecules. The smaller tetracationic cyclophane CBPQT$^{4+}$, which has the same p-xylylene linkers as OPVEBox$^{4+}$, however, does not form ring-in-ring(s) complexes with CB[8]. The formation of 1:1 and 1:2 complexes are driven, for the most part, by hydrophobic effect and ion-dipole interactions.

Notably, benefiting from the excellent photophysical properties of OPVEBox$^{4+}$ and the rigid hydrophobic cavity provided by CB[8], the resulting binary and ternary complexes show green and yellow fluorescence, respectively, both of which are red-shifted significantly compared with the sky-blue fluorescence of the free tetracationic cyclophane. Furthermore, multicolor fluorescent emission—e.g., sky-blue, cyan, green, and yellow—can be achieved by simply adding different equivalents of CB[8] to an aqueous solution of OPVEBox·4Cl. And the emission colors can be reversibly tuned by adding the competitive guests. The use of macrocycles to regulate the emission of organic molecules provides a simple strategy for fabricating multicolor smart luminescent materials in aqueous solutions, which have potential applications in the design and synthesis of multicolor biological imaging reagents and encryption materials.

Miscellaneous

Unless otherwise specified or indicated by context, the terms "a", "an", and "the" mean "one or more." For example, "a molecule" should be interpreted to mean "one or more molecules."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion additional components other than the components recited in the claims. The term "consisting essentially of" should be interpreted to be partially closed and allowing the inclusion only of additional components that do not fundamentally alter the nature of the claimed subject matter.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

All references, including publications, patent applications, and patents, cited herein are hereby incorporated by reference to the same extent as if each reference were individually and specifically indicated to be incorporated by reference and were set forth in its entirety herein.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES (1) (a) Pedersen, C. J. Cyclic Polyethers and Their Complexes with Metal Salts. J. Am. Chem. Soc. 1967, 89, 2495-2496. (b) Pedersen, C. J. Cyclic Polyethers and Their Complexes with Metal Salts. J. Am. Chem. Soc. 1967, 89, 7017-7036. (c) Pedersen, C. J. The Discovery of Crown Ethers (Nobel Lecture). Angew. Chem., Int. Ed. Engl. 1988, 27, 1021-1027.

(2) (a) Cram, D. J.; Cram, J. M. Host-Guest Chemistry: Complexes between Organic Compounds Simulate the Substrate Selectivity of Enzymes. Science 1974, 183, 803-809. (b) Lehn, J.-M. Supramolecular Chemistry: Receptors, Catalysts, and Carriers. Science 1985, 227, 849-856. (c) Lehn, J.-M. Supramolecular Chemistry—Scope and Perspectives Molecules, Supermolecules, and Molecular Devices (Nobel Lecture). Angew. Chem., Int. Ed. Engl. 1988, 27, 89-112. (d) Cram, D. J. The Design of Molecular Hosts, Guests, and Their Complexes (Nobel Lecture). Angew. Chem., Int. Ed. Engl. 1988, 27, 1009-1020. (e) Leininger, S.; Olenyuk, B.; Stang, P. J. Self-Assembly of Discrete Cyclic Nanostructures Mediated by Transition Metals. Chem. Rev. 2000, 100, 853-908. (f) Harada, A.; Takashima, Y.; Yamaguchi, H. Cyclodextrin-Based Supramolecular Polymers. Chem. Soc. Rev. 2009, 38, 875-882. (g) Lee, S.; Chen, C. H.; Flood, A. H. A Pentagonal Cyanostar Macrocycle with Cyanostilbene CH Donors Binds Anions and Forms Dialkylphosphate [3] Rotaxanes. Nat. Chem. 2013, 5, 704-710. (h) Peng, S.; He, Q.; Vargas-Zuniga, G. I.; Qin, L.; Hwang, I.; Kim, S. K.; Heo, N. J.; Lee, C. H.; Dutta, R.; Sessler, J. L. Strapped Calix[4]pyrroles: From Syntheses to Applications. Chem. Soc. Rev. 2020, 49, 865-907.

(3) (a) Ikeda, A.; Shinkai, S. Novel Cavity Design Using Calix[n]arene Skeletons: Toward Molecular Recognition and Metal Binding. Chem. Rev. 1997, 97, 1713-1734. (b) Rekharsky, M. V.; Inoue, Y. Complexation Thermodynamics of Cyclodextrins. Chem. Rev. 1998, 98, 1875-1918. (c) Ogoshi, T.; Yamagishi, T. A.; Nakamoto, Y. Pillar-Shaped Macrocyclic Hosts Pillar[n]arenes: New Key Players for Supramolecular Chemistry. Chem. Rev. 2016, 116, 7937-8002. (d) Ji, X.; Chi, X.; Ahmed, M.; Long, L.; Sessler, J. L. Soft Materials Constructed Using Calix[4]pyrrole- and "Texas-Sized" Box-Based Anion Receptors. Acc. Chem. Res. 2019, 52, 1915-1927. (e) Liu, Y.; Zhao, W.; Chen, C. H.; Flood, A. H. Chloride Capture Using a C—H Hydrogen-Bonding Cage. Science 2019, 365, 159-161.

(4) (a) Day, A. I.; Blanch, R. J.; Arnold, A. P.; Lorenzo, S.; Lewis, G. R.; Dance, I. A Cucurbituril-Based Gyroscane: A New Supramolecular Form. Angew. Chem. Int. Ed. 2002, 41, 275-277. (b) Chiu, S.-H.; Pease, A. R.; Stoddart, J. F.; White, A. J. P.; Williams, D. J. A Ring-in-Ring Complex. Angew. Chem. Int. Ed. 2002, 41, 270-274. (c) Loren, J. C.; Yoshizawa, M.; Haldimann, R. F.; Linden, A.; Siegel, J. S. Synthetic Approaches to a Molecular Borromean Link: Two-Ring Threading with Polypyridine Templates. Angew. Chem. Int. Ed. 2003, 42, 5702-5705. (d) Iwanaga, T.; Nakamoto, R.; Yasutake, M.; Takemura, H.; Sako, K.; Shinmyozu, T. Cyclophanes within Cyclophanes: The Synthesis of a Pyromellitic Diimide-Based Macrocycle as a Structural Unit in a Molecular Tube and Its Inclusion Phenomena. Angew. Chem. Int. Ed. 2006, 45, 3643-3647. (e) Sun, B.; Wang, M.; Lou, Z.; Huang, M.; Xu, C.; Li, X.; Chen, L. J.; Yu, Y.; Davis, G. L.; Xu, B.; Yang, H. B.; Li, X. From Ring-in-Ring to Sphere-in-Sphere: Self-Assembly of Discrete 2D and 3D Architectures with Increasing Stability. J. Am. Chem. Soc. 2015, 137, 1556-1564.

(5) (a) Kim, S.-Y.; Jung, I.-S.; Lee, E.; Kim, J.; Sakamoto, S.; Yamaguchi, K.; Kim, K. Macrocycles within Macrocycles: Cyclen, Cyclam, and Their Transition Metal Complexes Encapsulated in Cucurbit[8]uril. Angew. Chem. Int. Ed. 2001, 40, 2119-2121. (b) Dalgarno, S. J.; Atwood, J. L.; Raston, C. L. Sulfonatocalixarenes: Molecular Capsule and 'Russian Doll' Arrays to Structures Mimicking Viral Geometry. Chem. Commun. 2006, 4567-4574. (c) Rousseaux, S. A.; Gong, J. Q.; Haver, R.; Odell, B.; Claridge, T. D.; Herz, L. M.; Anderson, H. L. Self-Assembly of Russian Doll Concentric Porphyrin Nanorings. J. Am. Chem. Soc. 2015, 137, 12713-12718. (d) Zhiquan, L.; Polen, S.; Hadad, C. M.; RajanBabu, T. V.; Badjie, J. D. Russian Nesting Doll Complexes of Molecular Baskets and Zinc Containing TPA Ligands. J. Am. Chem. Soc. 2016, 138, 8253-8258. (e) Zhang, D.; Ronson, T. K.; Greenfield, J. L.; Brotin, T.; Berthault, P.; Leonce, E.; Zhu, J. L.; Xu, L.; Nitschke, J. R. Enantiopure [$Cs^+$/Xe ⊂Cryptophane]⊂$Fe^{II}_4L_4$ Hierarchical Superstructures. J. Am. Chem. Soc. 2019, 141, 8339-8345.

(6) (a) Forgan, R. S.; Spruell, J. M.; Olsen, J.-C.; Stern, C., L.; Stoddart, J. F. Towards the Stepwise Assembly of Molecular Borromean Rings. A Donor-Acceptor Ring-in-Ring Complex. J. Mex. Chem. Soc. 2009, 53, 134-138. (b) Forgan, R. S.; Sauvage, J.-P.; Stoddart, J. F. Chemical Topology: Complex Molecular Knots, Links, and Entanglements. Chem. Rev. 2011, 111, 5434-5464. (c) Forgan, R. S.; Wang, C.; Friedman, D. C.; Spruell, J. M.; Stern, C. L.; Sarjeant, A. A.; Cao, D.; Stoddart, J. F. Donor-Acceptor Ring-in-Ring Complexes. Chem. Eur. J. 2012, 18, 202-212. (d) Klosterman, J. K.; Veliks, J.; Frantz, D. K.; Yasui, Y.; Loepfe, M.; Zysman-Colman, E.; Linden, A.; Siegel, J. S. Conformations of Large Macrocycles and Ring-in-Ring Complexes. Org. Chem. Front. 2016, 3, 661-666. (e) Lu, Y.; Zhang, H. N.; Jin, G. X. Molecular Borromean Rings Based on Half-Sandwich Organometallic Rectangles. Acc. Chem. Res. 2018, 51, 2148-2158.

(7) (a) Lipke, M. C.; Wu, Y.; Roy, I.; Wang, Y.; Wasielewski, M. R.; Stoddart, J. F. Shuttling Rates, Electronic States, and Hysteresis in a Ring-in-Ring Rotaxane. ACS Cent. Sci. 2018, 4, 362-371. (b) Zhu, K.; Baggi, G.; Loeb, S. J. Ring-through-Ring Molecular Shuttling in a Saturated [3] Rotaxane. Nat. Chem. 2018, 10, 625-630.

(8) (a) Zhu, L.; Li, X.; Zhang, Q.; Ma, X.; Li, M.; Zhang, H.; Luo, Z.; Agren, H.; Zhao, Y. Unimolecular Photoconversion of Multicolor Luminescence on Hierarchical Self-Assemblies. J. Am. Chem. Soc. 2013, 135, 5175-5182. (b) Mei, J.; Leung, N. L.; Kwok, R. T.; Lam, J. W.; Tang, B. Z. Aggregation-Induced Emission: Together We Shine, United We Soar! Chem. Rev. 2015, 115, 11718-11940. (c) Su, Y.; Phua, S. Z. F.; Li, Y.; Zhou, X.; Jana, D.; Liu, G.; Lim, W. Q.; Ong, W. K.; Yang, C.; Zhao, Y. Ultralong Room Temperature Phosphorescence from Amorphous Organic Materials toward Confidential Information Encryption and Decryption. Sci. Adv. 2018, 4, eaas9732. (d) Su, Y.; Zhang, Y.; Wang, Z.; Gao, W.; Jia, P.; Zhang, D.; Yang, C.; Li, Y.; Zhao, Y. Excitation-Dependent Long-Life Luminescent Polymeric Systems under Ambient Conditions. Angew. Chem. Int. Ed. 2020, 59, 9967-9971.

(9) Lukinavicius, G.; Reymond, L.; Umezawa, K.; Sallin, O.; D'Este, E.; Gottfert, F.; Ta, H.; Hell, S. W.; Urano, Y.; Johnsson, K. Fluorogenic Probes for Multicolor Imaging in Living Cells. J. Am. Chem. Soc. 2016, 138, 9365-9368.

(10) (a) Qi, Q.; Li, C.; Liu, X.; Jiang, S.; Xu, Z.; Lee, R.; Zhu, M.; Xu, B.; Tian, W. Solid-State Photoinduced Luminescence Switch for Advanced Anticounterfeiting and Super-Resolution Imaging Applications. J. Am. Chem. Soc. 2017, 139, 16036-16039. (b) Wu, H.; Chen, Y.; Liu, Y. Reversibly Photoswitchable Supramolecular Assembly and Its Application as a Photoerasable Fluorescent Ink. Adv. Mater. 2017, 29, 1605271. (c) Gu, L.; Shi, H.; Bian, L.; Gu, M.; Ling, K.; Wang, X.; Ma, H.; Cai, S.; Ning, W.; Fu, L.; Wang, H.; Wang, S.; Gao, Y.; Yao, W.; Huo, F.; Tao, Y.; An, Z.; Liu, X.; Huang, W. Colour-Tunable Ultra-Long Organic Phosphorescence of a Single-Component Molecular Crystal. Nat. Photonics. 2019, 13, 406-411.

(11) Li, S.; Peele, B. N.; Larson, C. M.; Zhao, H.; Shepherd, R. F. A Stretchable Multicolor Display and Touch Interface Using Photopatterning and Transfer Printing. Adv. Mater. 2016, 28, 9770-9775.

(12) Kim, E.; Lee, Y.; Lee, S.; Park, S. B. Discovery, Understanding, and Bioapplication of Organic Fluorophore: A Case Study with an Indolizine-Based Novel Fluorophore, Seoul-Fluor. Acc. Chem. Res. 2015, 48, 538-547.

(13) (a) Ni, X. L.; Chen, S.; Yang, Y.; Tao, Z. Facile Cucurbit[8]uril-Based Supramolecular Approach to Fabricate Tunable Luminescent Materials in Aqueous Solution. J. Am. Chem. Soc. 2016, 138, 6177-6183. (b) Wu, H.; Chen, Y.; Dai, X.; Li, P.; Stoddart, J. F.; Liu, Y. In Situ Photoconversion of Multicolor Luminescence and Pure White Light Emission Based on Carbon Dot-Supported Supramolecular Assembly. J. Am. Chem. Soc. 2019, 141, 6583-6591. (c) Chen, W.; Guo, C.; He, Q.; Chi, X.; Lynch, V. M.; Zhang, Z.; Su, J.; Tian, H.; Sessler, J. L. Molecular Cursor Caliper: A Fluorescent Sensor for Dicarboxylate Dianions. J. Am. Chem. Soc. 2019, 141, 14798-14806. (d) Chang, X.; Zhou, Z.; Shang, C.; Wang, G.; Wang, Z.; Qi, Y.; Li, Z. Y.; Wang, H.; Cao, L.; Li, X.; Fang, Y.; Stang, P. J. Coordination-Driven Self-Assembled Metallacycles Incorporating Pyrene: Fluorescence Mutability, Tunability, and Aromatic Amine Sensing. J. Am. Chem. Soc. 2019, 141, 1757-1765. (e) Zhou, Z.; Chen, D. G.; Saha, M. L.; Wang, H.; Li, X.; Chou, P. T.; Stang, P. J. Designed Conformation and Fluorescence Properties of Self-Assembled Phenazine-Cored Platinum(II) Metallacycles. J. Am. Chem. Soc. 2019, 141, 5535-5543. (f) Wei, P.; Zhang, X.; Liu, J.; Shan, G. G.; Zhang, H.; Qi, J.; Zhao, W.; Sung, H. H.; Williams, I. D.; Lam, J. W. Y.; Tang, B. Z. New Wine in Old Bottles: Prolonging Room-Temperature Phosphorescence of Crown Ethers by Supramolecular Interactions. Angew. Chem. Int. Ed. 2020, 59, 9293-9298.

(14) (a) Zhang, Q. W.; Li, D.; Li, X.; White, P. B.; Mecinovic, J.; Ma, X.; Agren, H.; Nolte, R. J. M.; Tian, H. Multicolor Photoluminescence Including White-Light Emission by a Single Host-Guest Complex. J. Am. Chem. Soc. 2016, 138, 13541-13550. (b) Wang, Q.; Zhang, Q.; Zhang, Q. W.; Li, X.; Zhao, C. X.; Xu, T. Y.; Qu, D. H.; Tian, H. Color-Tunable Single-Fluorophore Supramolecular System with Assembly-Encoded Emission. Nat. Commun. 2020, 11, 158.

(15) (a) Odell, B.; Reddington, M. V.; Slawin, A. M. Z.; Spencer, N.; Stoddart, J. F.; Williams, D. J. Cyclobis (paraquat-p-phenylene). A Tetracationic Multipurpose Receptor. Angew. Chem., Int. Ed. Engl. 1988, 27, 1547-1550. (b) Ashton, P. R.; Odell, B.; Reddington, M. V.; Slawin, A. M. Z.; Stoddart, J. F.; Williams, D. J. Isostructural, Alternately-Charged Receptor Stacks. The Inclusion Complexes of Hydroquinone and Catechol Dimethyl Ethers with Cyclobis(paraquat-p-phenylene). Angew. Chem., Int. Ed. Engl. 1988, 27, 1550-1553.

(16) Ashton, P. R.; Brown, C. L.; Chrystal, E. J. T.; Goodnow, T. T.; Kaifer, A. E.; Parry, K. P.; Philp, D.; Slawin, A. M. Z.; Spencer, N.; Stoddart, J. F.; Williams, D. J. The Self-Assembly of a Highly Ordered [2] Catenane. J. Chem. Soc., Chem. Commun. 1991, 634-639.

(17) Philp, D.; Slawin, A. M. Z.; Spencer, N.; Stoddart, J. F.; Williams, D. J. The Complexation of Tetrathiafulvalene by Cyclobis(paraquat-p-phenylene). J. Chem. Soc., Chem. Commun. 1991, 1584-1586.

(18) (a) Amabilino, D. B.; Ashton, P. R.; Boyd, S. E.; Lee, J. Y.; Menzer, S.; Stoddart, J. F.; Williams, D. J. The Five-Stage Self-Assembly of a Branched Heptacatenane. Angew. Chem., Int. Ed. Engl. 1997, 36, 2070-2072. (b) Stoddart, J. F. The Chemistry of the Mechanical Bond. Chem. Soc. Rev. 2009, 38, 1802-1820.

(19) (a) Spruell, J. M.; Coskun, A.; Friedman, D. C.; Forgan, R. S.; Sarjeant, A. A.; Trabolsi, A.; Fahrenbach, A. C.; Barin, G.; Paxton, W. F.; Dey, S. K.; Olson, M. A.; Benitez, D.; Tkatchouk, E.; Colvin, M. T.; Carmielli, R.; Caldwell, S. T.; Rosair, G. M.; Hewage, S. G.; Duclairoir, F.; Seymour, J. L.; Slawin, A. M.; Goddard, W. A., III; Wasielewski, M. R.; Cooke, G.; Stoddart, J. F. Highly Stable Tetrathiafulvalene Radical Dimers in [3] Catenanes. Nat. Chem. 2010, 2, 870-879. (b) Dale, E. J.; Vermeulen, N. A.; Thomas, A. A.; Barnes, J. C.; Jurioek, M.; Blackburn, A. K.; Strutt, N. L.; Sarjeant, A. A.; Stern, C. L.; Denmark, S. E.; Stoddart, J. F. Excage. J. Am. Chem. Soc. 2014, 136, 10669-10682. (c) Wu, H.; Chen, Y.; Zhang, L.; Anamimoghadam, O.; Shen, D.; Liu, Z.; Cai, K.; Pezzato, C.; Stern, C. L.; Liu, Y.; Stoddart, J. F. A Dynamic Tetracationic Macrocycle Exhibiting Photoswitchable Molecular Encapsulation. J. Am. Chem. Soc. 2019, 141, 1280-1289.

(20) Dale, E. J.; Vermeulen, N. A.; Juriček, M.; Barnes, J. C.; Young, R. M.; Wasielewski, M. R.; Stoddart, J. F. Supramolecular Explorations: Exhibiting the Extent of Extended Cationic Cyclophanes. Acc. Chem. Res. 2016, 49, 262-273.

(21) (a) Lipke, M. C.; Cheng, T.; Wu, Y.; Arslan, H.; Xiao, H.; Wasielewski, M. R.; Goddard, W. A., III; Stoddart, J. F. Size-Matched Radical Multivalency. J. Am. Chem. Soc. 2017, 139, 3986-3998. (b) Dumartin, M.; Lipke, M. C.; Stoddart, J. F. A Redox-Switchable Molecular Zipper. J. Am. Chem. Soc. 2019, 141, 18308-18317.

(22) Cai, K.; Lipke, M. C.; Liu, Z.; Nelson, J.; Cheng, T.; Shi, Y.; Cheng, C.; Shen, D.; Han, J. M.; Vemuri, S.; Feng, Y.; Stern, C. L.; Goddard, W. A., III; Wasielewski, M. R.; Stoddart, J. F. Molecular Russian Dolls. Nat. Commun. 2018, 9, 5275.

(23) (a) Freeman, W. A.; Mock, W. L.; Shih, N. Y. Cucurbituril. J. Am. Chem. Soc. 1981, 103, 7367-7368. (b) Mock, W. L.; Shih, N. Y. Host-Guest Binding Capacity of Cucurbituril. J. Org. Chem. 1983, 48, 3618-3619. (c) Liu, S.; Zavalij, P. Y.; Isaacs, L. Cucurbit[10]uril. J. Am. Chem. Soc. 2005, 127, 16798-16799. (d) Isaacs, L. Stimuli Responsive Systems Constructed Using Cucurbit[n]uril-Type Molecular Containers. Acc. Chem. Res. 2014, 47, 2052-2062. (e) Barrow, S. J.; Kasera, S.; Rowland, M. J.; del Barrio, J.; Scherman, O. A. Cucurbituril-Based Molecular Recognition. Chem. Rev. 2015, 115, 12320-12406. (f) Das, D.; Assaf, K. I.; Nau, W. M. Applications of Cucurbiturils in Medicinal Chemistry and Chemical Biology. Front. Chem. 2019, 7, 619.

(24) (a) Kim, H. J.; Jeon, W. S.; Ko, Y. H.; Kim, K. Inclusion of Methylviologen in Cucurbit[n]uril. Proc. Natl. Acad. Sci. U.S.A. 2002, 99, 5007-5011. (b) Ong, W.; Kaifer, A. E. Salt Effects on the Apparent Stability of the Cucurbit[7]uril-Methyl Viologen Inclusion Complex. J. Org. Chem. 2004, 69, 1383-1385. (c) Liu, S.; Ruspic, C.; Mukhopadhyay, P.; Chakrabarti, S.; Zavalij, P. Y.; Isaacs, L. The Cucurbit[n]uril Family: Prime Components for Self-Sorting Systems. J. Am. Chem. Soc. 2005, 127, 15959-15967.

(25) Gong, W.; Yang, X.; Zavalij, P. Y.; Isaacs, L.; Zhao, Z.; Liu, S. From Packed "Sandwich" to "Russian Doll": Assembly by Charge-Transfer Interactions in Cucurbit[10]uril. Chem. Eur. J. 2016, 22, 17612-17618.

(26) (a) Kim, J.; Jung, I.-S.; Kim, S.-Y.; Lee, E.; Kang, J.-K.; Sakamoto, S.; Yamaguchi, K.; Kim, K. New Cucurbituril Homologues: Syntheses, Isolation, Characterization, and X-Ray Crystal Structures of Cucurbit[n]uril (n=5, 7, and 8). J. Am. Chem. Soc. 2000, 122, 540-541. (b) All the distances defining the size of CB[8] in the current research were measured from atom to atom according to the single crystal of CB[8] in reference 26a.

(27) (a) Kim, H.-J.; Heo, J.; Jeon, W. S.; Lee, E.; Kim, J.; Sakamoto, S.; Yamaguchi, K.; Kim, K. Selective Inclusion of a Hetero-Guest Pair in a Molecular Host: Formation of Stable Charge-Transfer Complexes in Cucurbit[8]uril. Angew. Chem. Int. Ed. 2001, 40, 1526-1529. (b) Bush, M. E.; Bouley, N. D.; Urbach, A. R. Charge-Mediated Recognition of N-Terminal Tryptophan in Aqueous Solution by a Synthetic Host. J. Am. Chem. Soc. 2005, 127, 14511-14517. (c) Biedermann, F.; Rauwald, U.; Cziferszky, M.; Williams, K. A.; Gann, L. D.; Guo, B. Y.; Urbach, A. R.; Bielawski, C. W.; Scherman, O. A. Benzobis(imidazolium)-Cucurbit[8]uril Complexes for Binding and Sensing Aromatic Compounds in Aqueous Solution. Chem. Eur. J. 2010, 16, 13716-13722. (d) Yang, X.; Wang, R.; Kermagoret, A.; Bardelang, D. Oligomeric Cucurbituril Complexes: From Peculiar Assemblies to Emerging Applications. Angew. Chem. Int. Ed. 2020, DOI: 10.1002/anie.202004622.

(28) (a) Huang, Z.; Yang, L.; Liu, Y.; Wang, Z.; Scherman, O. A.; Zhang, X. Supramolecular Polymerization Promoted and Controlled through Self-Sorting. Angew. Chem. Int. Ed. 2014, 53, 5351-5355. (b) Yang, H.; Ma, Z.; Yuan, B.; Wang, Z.; Zhang, X. Supramolecular Polymerization at the Interface: Layer-by-Layer Assembly Driven by Host-Enhanced $\pi$-$\pi$ Interaction. Chem. Commun. 2014, 50, 11173-11176.

(29) (a) Zhang, K. D.; Tian, J.; Hanifi, D.; Zhang, Y.; Sue, A. C.; Zhou, T. Y.; Zhang, L.; Zhao, X.; Liu, Y.; Li, Z. T. Toward a Single-Layer Two-Dimensional Honeycomb Supramolecular Organic Framework in Water. J. Am. Chem. Soc. 2013, 135, 17913-17918. (b) Tian, J.; Zhou, T. Y.; Zhang, S. C.; Aloni, S.; Altoe, M. V.; Xie, S. H.; Wang, H.; Zhang, D. W.; Zhao, X.; Liu, Y.; Li, Z. T. Three-Dimensional Periodic Supramolecular Organic Framework Ion Sponge in Water and Microcrystals. Nat. Commun. 2014, 5, 5574.

(30) (a) Jeon, W. S.; Kim, H. J.; Lee, C.; Kim, K. Control of the Stoichiometry in Host-Guest Complexation by Redox Chemistry of Guests: Inclusion of Methylviologen in Cucurbit[8]uril. Chem. Commun. 2002, 1828-1829. (b) Carvalho, C. P.; Dominguez, Z.; Da Silva, J. P.; Pischel, U. A Supramolecular Keypad Lock. Chem. Commun. 2015, 51, 2698-2701. (c) Tang, X.; Huang, Z.; Chen, H.; Kang, Y.; Xu, J. F.; Zhang, X. Supramolecularly Catalyzed Polymerization: From Consecutive Dimerization to Polymerization. Angew. Chem. Int. Ed. 2018, 57, 8545-8549. (d) Olesinska, M.; Wu, G.; Gomez-Coca, S.; Anton-Garcia, D.; Szabo, I.; Rosta, E.; Scherman, O. A. Modular Supramolecular Dimerization of Optically Tunable Extended Aryl Viologens. Chem. Sci. 2019, 10, 8806-8811. (e) Wu, G.; Szabo, I.; Rosta, E.; Scherman, O. A. Cucurbit[8]uril-Mediated Pseudo[2,3]rotaxanes. Chem. Commun. 2019, 55, 13227-13230. (f) Wu, G.; Bae, Y. J.; Olesinska, M.; Anton-Garcia, D.; Szabo, I.; Rosta, E.; Wasielewski, M. R.; Scherman, O. A. Controlling the Structure and Photophysics of Fluorophore Dimers Using Multiple Cucurbit[8]uril Clampings. Chem. Sci. 2020, 11, 812-825.

(31) (a) Koshland, D. E. Application of a Theory of Enzyme Specificity to Protein Synthesis. Proc. Natl. Acad. Sci. U.S.A. 1958, 44, 98-104. (b) Koshland, D. E. The Key-Lock Theory and the Induced Fit Theory. Angew. Chem., Int. Ed. Engl. 1995, 33, 2375-2378. (c) Sawada, T.; Hisada, H.; Fujita, M. Mutual Induced Fit in a Synthetic Host-Guest System. J. Am. Chem. Soc. 2014, 136, 4449-4451.

(32) Peck, E. M.; Liu, W.; Spence, G. T.; Shaw, S. K.; Davis, A. P.; Destecroix, H.; Smith, B. D. Rapid Macrocycle Threading by a Fluorescent Dye-Polymer Conjugate in Water with Nanomolar Affinity. J. Am. Chem. Soc. 2015, 137, 8668-8671.

(33) (a) Ihde, J. Le Châtelier and Chemical Equilibrium. J. Chem. Educ. 1989, 66, 238. (b) Dhara, A.; Flood, A. H. Cages Driven Away from Equilibrium Binding by Electric Fields. Chem 2019, 5, 1017-1019.

(34) Sinn, S.; Spuling, E.; Brase, S.; Biedermann, F. Rational Design and Implementation of a Cucurbit[8]uril-Based Indicator-Displacement Assay for Application in Blood Serum. Chem. Sci. 2019, 10, 6584-6593.

(35) (a) Hua, Y.; Flood, A. H. Click Chemistry Generates Privileged CH Hydrogen-Bonding Triazoles: The Latest Addition to Anion Supramolecular Chemistry. Chem. Soc. Rev. 2010, 39, 1262-1271. (b) Xia, D.; Wang, P.; Ji, X.; Khashab, N. M.; Sessler, J. L.; Huang, F. Functional Supramolecular Polymeric Networks: The Marriage of Covalent Polymers and Macrocycle-Based Host-Guest Interactions. Chem. Rev. 2020, 120, 6070-6123.

(36) (a) Raymo, F. M.; Stoddart, J. F. Interlocked Macromolecules. Chem. Rev. 1999, 99, 1643-1664. (b) Fang, L.; Olson, M. A.; Benitez, D.; Tkatchouk, E.; Goddard, W. A., III; Stoddart, J. F. Mechanically Bonded Macromolecules. Chem. Soc. Rev. 2010, 39, 17-29. (c) Mena-Hernando, S.; Perez, E. M. Mechanically Interlocked Materials. Rotaxanes and Catenanes Beyond the Small Molecule. Chem. Soc. Rev. 2019, 48, 5016-5032.

EXAMPLES

Section A. Materials/General Methods/Instruments

All solvents and reagents were obtained commercially and used without further purification unless noted otherwise. 1,4-Bis((E)-2-(pyridin-4-yl)vinyl)benzene (1,4-BPEB), 1,4-phenylenebis(ethene-2,1-diyl))bis(1-(4-(bromomethyl)benzyl)pyridin-1-ium) ($BrOPV^{2+}$) and 4,4'-((1E,1'E)-1,4-phenylenebis(ethene-2,1-diyl))bis(1-methylpyridin-1-ium) ($OPV^{2+}$) were prepared according to the previous literature procedures.[1] Thin-layer chromatography (TLC) was performed on silica gel 60 F254 (E Merck). Developed plates were visualized using UV light at wavelengths of 254 and 365 nm. Reverse-phase liquid chromatography was performed on Combiflash Rf 200 purification system, using C18-columns and a binary solvent system (MeCN with 0.1% TFA and $H_2O$ with 0.1% TFA). Normal-phase column chromatography was carried out on silica gel 60F (Merck 9385, 0.040-0.063 mm). UV-Vis Absorption spectra were recorded in a conventional rectangular quartz cell (10×10×45 mm) on a UV-3600 Shimadzu spectrophotometer. Fluorescence spectra were measured in a rectangular quartz cell (10×10×45 mm) on a HORIBA FluoroMax-4 spectrometer, which was equipped with an integrating sphere for absolute fluorescence quantum yields determination and time-correlated single-photon counting (TCSPC) module for emission decays. All the photophysical (UV-Vis absorption and fluorescence spectroscopy) experiments were performed at 298 K in $H_2O$, except the nuclear magnetic resonance (NMR) experiments which were performed in $CD_3CN$ and $D_2O$. NMR Spectra were recorded on a Bruker Avance III 600 MHz and Agilent 500 MHz spectrometers, with working frequencies of 600 and 500 MHz for 41 NMR, as well as 150 and 125 MHz for $^{13}C$ NMR, respectively. 2D DOSY NMR Spectroscopy was conducted in $D_2O$ with the concentration of OPVEBox·4Cl held at 0.2 mM. The spectrometer was set with the following parameters: the pulse sequence: Bruker pulse program dstebpgp3s; the relaxation delay (D1): 2 s; the diffusion time (D20): 0.06 s; the diffusion gradient pulse length (P30): 1.0 ms; the number of scan (ns): 16; the number of gradient steps: 32 steps with linear spacing; the gradient range: 2-85%. Single crystal X-ray diffraction studies were measured on a Bruker Kappa APEX2 CCD or a Rigaku XtaLAB Synergy diffractometer using Cu-Kα radiation (λ=1.5407 Å) equipped with an Oxford cryostream variable temperature device, and data were collected using the Bruker APEX-II or Rigaku CrysAlis Pro program. Detailed experimental procedures are provided below in the appropriate sections. Cyclic voltammetry (CV) was performed on a Gamry Multipurpose instrument (Reference 600) interfaced to a PC with a three-electrode system under a $N_2$ atmosphere at 298 K. Microcalorimetric titrations were performed on a thermostated TA Nano Isothermal Titration calorimeter at atmospheric pressure and 298 K, the data were analyzed with NanoAnalyze software. Electrospray ionization-mass spectra (ESI-MS) were measured on Waters Synapt G2 mass spectrometer. The specific experimental conditions were employed as follow: ESI capillary voltage, 2.0 kV; sample cone voltage, 20 V; extraction cone voltage, 0.1 V; source temperature, 120° C.; desolvation temperature, 150° C.; cone gas flow, 10 L/h; desolvation gas flow, 700 L/h ($N_2$).

Section B. Synthetic Protocols

OPVEBox·$4PF_6$: Two different reactions, as shown in SCHEME 1, were carried out for the ring-closing step: (1) catalyst without template and (2) catalyst with a template.

SCHEME 1. Synthetic routes of OPVEBox•4PF6.

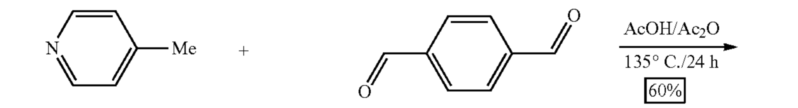

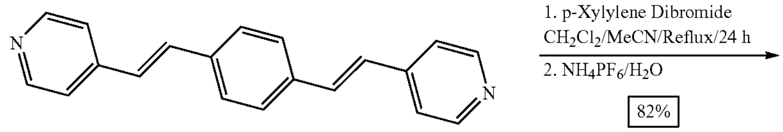

1,4-BPEB

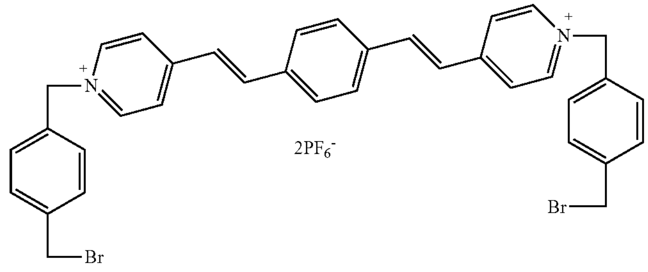

BrOPV•$2PF_6$

-continued

SCHEME 1. Synthetic routes of OPVEBox•4PF6.

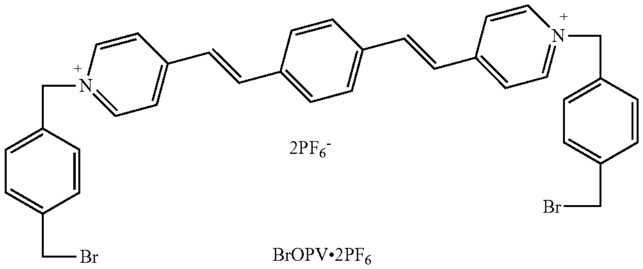

BrOPV•2PF$_6$

+

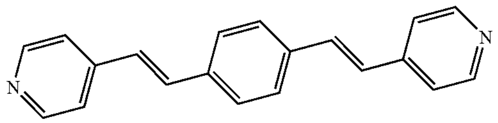

1,4-BPEB

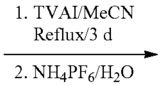

| Reaction | Catalyst | Template | Yield/% |
| --- | --- | --- | --- |
| (1) | TBAI | – | 40 |
| (2) | TBAI | Pyrene | 42 |

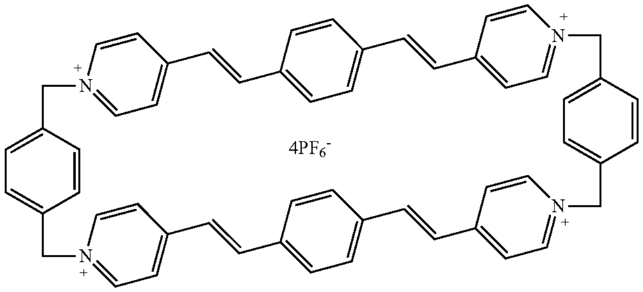

OPVEBox•4PF$_6$ (1) TBAI as a catalyst without template: BrOPV·2PF$_6$ (141 mg, 0.15 mmol) and 1,4-BPEB (43 mg, 0.15 mmol) were dissolved in dry MeCN (75 mL), followed by adding 0.2 equiv of TBAI (11 mg, 0.03 mmol) as catalyst. The resulting mixture was heated at 80° C. for 3 days under a $N_2$ atmosphere. After cooling to room temp, excess TBACl was added to quench the reaction resulting in a yellow precipitate which was collected by filtration and washed with $Me_2CO$ and $CH_2Cl_2$. The crude precipitate was then subjected to reverse-phase C18 column chromatogram, starting with $H_2O$/0.1% TFA as eluent, followed by continuous addition of MeCN/0.1% TFA over the course of 45 min. The fractions containing the desired product were combined, and followed by removal of MeCN by rotary evaporation under vacuum. The residual aqueous mixture was then treated with excess $NH_4PF_6$ The resulting yellow precipitate was separated by filtration and dried under vacuum yielding pure OPVEBox·4PF$_6$ (yield: 40%).

(2) TBAI as a catalyst and pyrene as a template: A solution of BrOPV·2PF$_6$ (141 mg, 0.15 mmol), 1,4-BPEB (43 mg, 0.15 mmol), TBAI (11 mg, 0.03 mmol) and 6 equiv of pyrene (182 mg, 0.90 mmol) in dry MeCN (75 mL) was heated under reflux at 80° C. for 3 days. After cooling to room temp, excess TBACl was added to quench the reaction. The resulting crude precipitate was separated by filtration, and then dissolved in $H_2O$ in order to remove the pyrene template by continuous liquid-liquid extraction with $CHCl_3$ over 3 days. The color of aqueous phase changed from brown to yellow. The aqueous phase was concentrated by rotary evaporation under vacuum and the resulting crude precipitate was then subjected to reverse-phase $C_{18}$ column chromatography, starting with $H_2O$/0.1% TFA as eluent, followed by continuous addition of MeCN up to an eluent mixture of 99.9% MeCN/0.1% TFA over the course of 45 min. The fractions containing the desired product were combined and concentrated by rotary evaporation under vacuum. The residue was dissolved in $H_2O$ and treated with excess $NH_4PF_6$ to afford a yellow precipitate, which after filtration and drying under a vacuum yielded pure OPVEBox·$4PF_6$ (yield: 42%).

$^1$H NMR (600 MHz, $CD_3CN$) δ 8.60 (d, J=7.0 Hz, 2H), 7.90 (d, J=7.0 Hz, 2H), 7.65 (d, J=16.1 Hz, 3H), 7.58 (s, 2H), 7.26 (d, J=16.4 Hz, 1H), 5.58 (s, 2H). $^{13}$C NMR (150 MHz, $CD_3CN$) δ 154.9, 144.5, 141.6, 137.8, 137.1, 131.0, 129.8, 125.6, 124.7, 64.4. HRMS-ESI for OPVEBox·$4PF_6$; Calcd for $C_{56}H_{48}F_{24}N_4P_4$: m/z=1211.2804 $[M-PF_6]^+$, 533.1598 $[M-2PF_6]^{2+}$; Found: 1211.2807 $[M-PF_6]^+$, 533.1595 $[M-2PF_6]^{2+}$.

OPVEBox·4Cl: A water-soluble counterpart of OPVEBox·4Cl was obtained by means of counterion exchange: Tetrabutylammonium chloride (TBACl, 300 mg) was added to a MeCN solution (4 mL) of OPVEBox·$4PF_6$ (100 mg). The resulting yellow precipitate was collected by centrifugation and washed with $Me_2CO$ to give the desired compound OPVEBox·4Cl (67 mg) as a yellow powder (yield: 99%).

$^1$H NMR (600 MHz, $D_2O$) δ 8.74 (d, J=6.6 Hz, 2H), 7.95 (d, J=6.2 Hz, 2H), 7.64 (m, 5H), 7.26 (d, J=16.3 Hz, 1H), 5.71 (s, 2H). $^{13}$C NMR (125 MHz, $D_2O$) δ 153.9, 143.2, 140.2, 136.7, 135.9, 129.9, 128.7, 124.6, 123.8, 63.4. ESI-TOF for OPVEBox·4Cl; Calcd for $C_{56}H_{48}Cl_4N_4$: m/z=194.10 $[M-4Cl]^{4+}$, 258.46 $[M-4Cl—H]^{3+}$, 423.16 $[M-2Cl]^{2+}$, Found: 194.10 $[M-4Cl]^{4+}$, 258.46 $[M-4Cl—H]^{3+}$, 423.16 $[M-2Cl]^{2+}$.

Section C. NMR Spectroscopy

Figure 7:
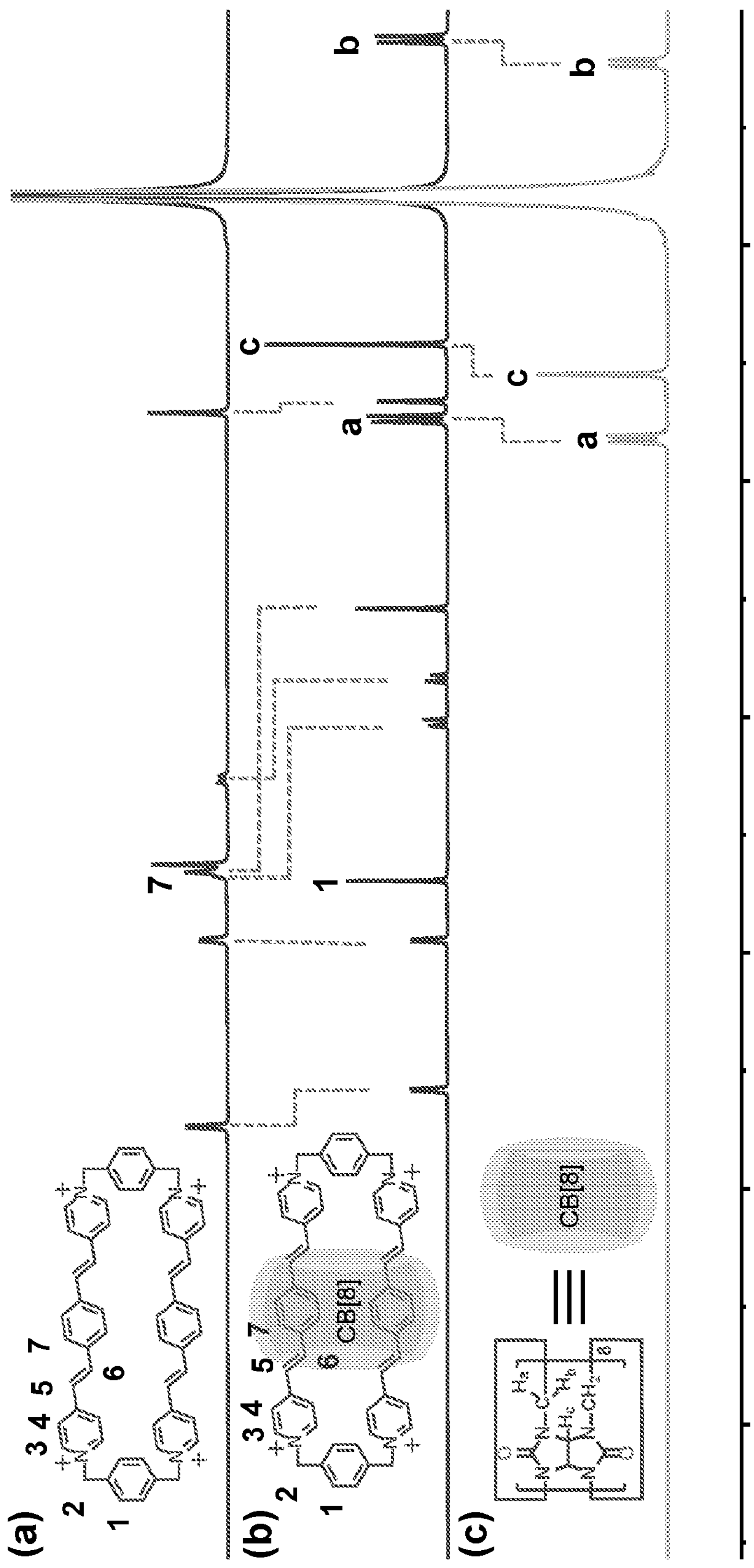
FIG. 7. $^1$H NMR Spectra (600 MHz, [OPVEBox$^{4+}$]=[CB[8]]=2.0×10$^{-4}$ M, $D_2O$, 298 K) of (a) OPVEBox$^{4+}$, (b) OPVEBox$^{4+}$⊂CB[8] ring-in-ring complex, and (c) CB[8] showing the chemical shift changes of OPVEBox$^{4+}$ and CB[8] upon forming the binary OPVEBox$^{4+}$⊂CB[8] ring-in-ring complex. The chemical shifts of proton H-7 residing on the central phenylene groups and the protons (H-5 and H-6) residing on the C═C double bonds show large upfield shifts (Δδ=−0.64, −0.43 and −1.12 for H-5, H-6, and H-7, respectively), together with the small upfield shifts of the signal for protons on CB[8] (Δδ=−0.09, −0.11 and −0.13 for H-a, H-b, and H-c, respectively), indicating that CB[8] is bound in the middle of OPVEBox$^{4+}$ to form the 1:1 ring-in-ring structure.

The one-dimensional 1H NMR spectroscopy of OPVE-Box$^{4+}$⊂CB[8] ring-in-ring complex is shown in FIG. 7.

Figure 8:
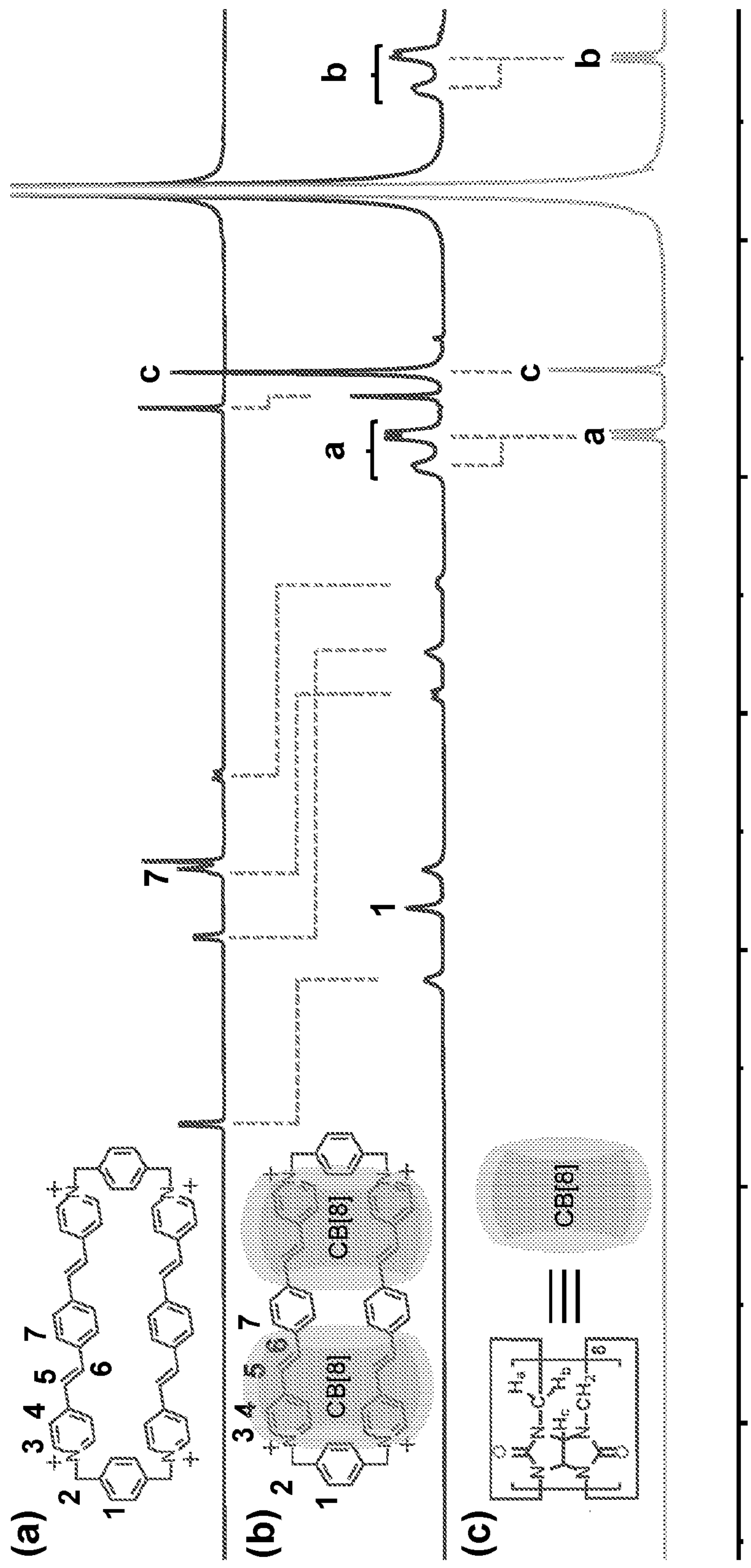
FIG. 8. $^1$H NMR Spectra (600 MHz, [OPVEBox$^{4+}$]=2.0×10$^{-4}$, [CB[8]]=4.0×10$^{-4}$ M, $D_2O$, 298 K) of (a) OPVEBox$^{4+}$, (b) OPVEBox$^{4+}$⊂2CB[8] ring-in-rings complex, and (c) CB[8], showing the chemical shift changes of OPVEBox$^{4+}$ and CB[8] upon forming the OPVEBox$^{4+}$⊂2CB[8] ring-in-rings complex. All the protons residing on the pyridinium groups and the C═C double bonds display large upfield shifts (Δδ=−0.61, −1.20, −0.75 and −0.81 for H-3, H-4, H-5, and H-6, respectively), while the chemical shift of H-7 showed no change, indicating that two CB[8] molecules are bound to the two ends of OPVEBox$^{4+}$ to form the 1:2 ring-in-rings superstructure. All the methylene protons (H-a and H-b) on CB[8] were split into two sets of peaks (δ=5.96/5.82 and 4.36/4.22 for H-a and H-b, respectively), indicating that the centrosymmetric geometry of CB[8] molecules has been broken.

The one-dimensional 1H NMR spectroscopy of OPVE-Box$^{4+}$⊂2CB[8] ring-in-rings complex is shown in FIG. 8.

Figure 9:
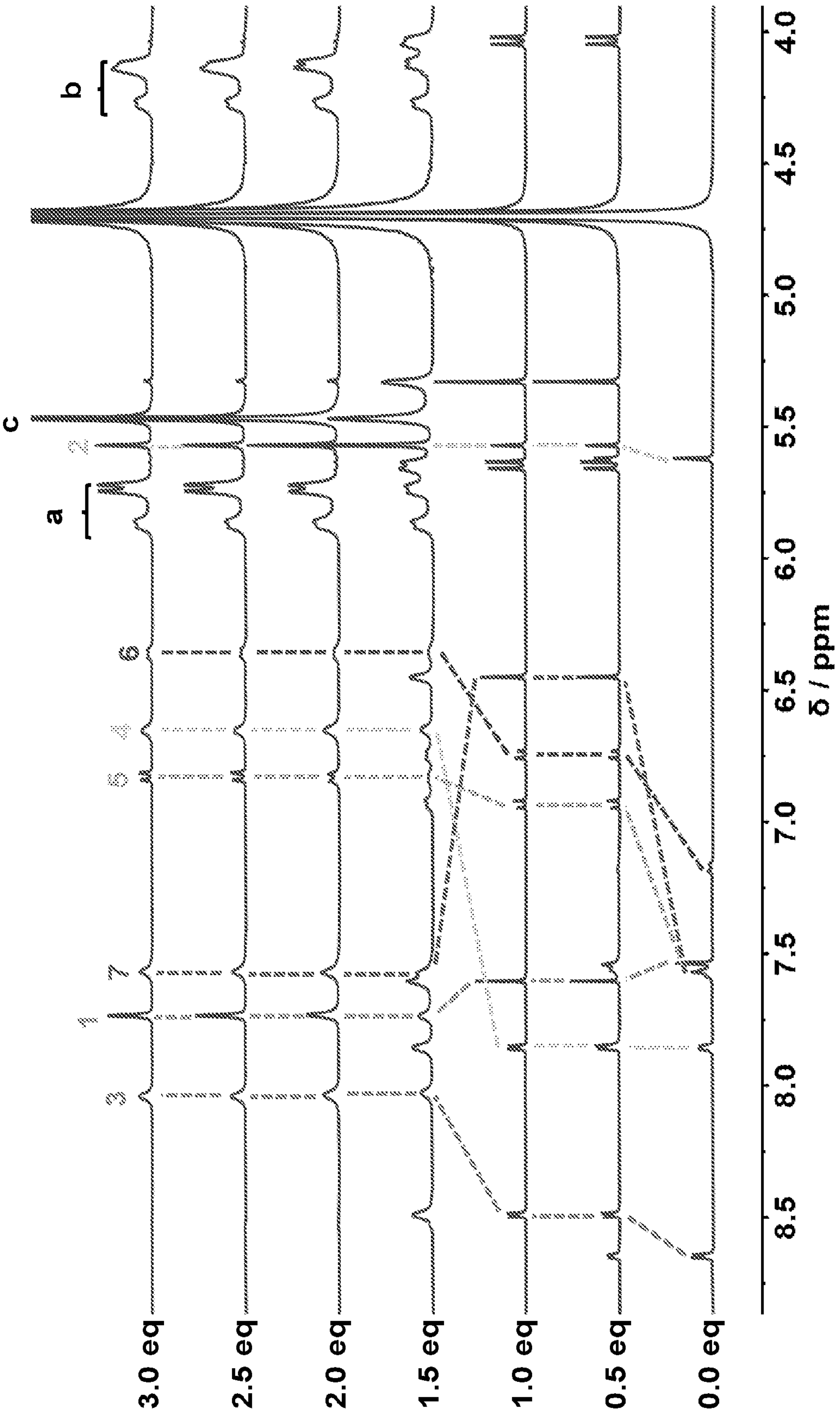
FIG. 9. $^1$H NMR Titration (600 MHz, $H_2O$, 298 K) of OPVEBox$^{4+}$ upon addition different equiv of CB[8] ([(OPVEBox$^{4+}$]=2.0×10$^{-4}$ M, [CB[8]]/[OPVEBox$^{4+}$]=0-3 eq). The annotations show the chemical shift changes of the protons in OPVEBox$^{4+}$ upon addition different equiv of CB[8].

The $^1$H NMR Titrations between OPVEBox$^{4+}$ and CB[8] is shown in FIG. 9.

Section E. Crystallographic Characterization (1) OPVEBox·4Cl (a) Method. OPVEBox·4Cl (0.5 mg, 0.5 μmop was dissolved in deionized $H_2O$ (1.0 mL), and the resulting solution was passed through a 0.45-μm filter. Then the filter was added into two 1-mL tubes with volumes of 0.2 and 0.4 mL, respectively. The tubes were placed together in one 20-mL vial containing $Me_2CO$ (~3 mL) and the vial was capped. Slow vapor diffusion of $Me_2CO$ into the aqueous solution of OPVEBox·4Cl (0.5 mM) during 1 week, yielded yellow single crystals of OPVEBox·4Cl. A suitable crystal was mounted on a MITIGEN holder with Paratone oil on a XtaLAB Synergy, Single source at home/near, HyPix diffractometer. The crystal was kept at 100.01(10) K during data collection. Using Olex2$^2$, the structure was solved with the ShelXT$^3$ structure solution program using Intrinsic Phasing and refined with the XL$^4$ refinement package using Least Squares minimisation. The solid-state (super)structure of OPVEBox·4Cl is shown in FIG. 1.

(b) Crystal Parameters. $[C_{58}H_{48}N_4\cdot(Cl)_4]\cdot(C_3H_6O)_2\cdot(H_2O)_6$. Mr=1143.03. Yellow block (0.171×0.065×0.021 $mm^3$). Monoclinic, space group $P2_1/c$ (no. 14), a=15.6756(7), b=11.7857(4), c=16.4783(8) Å, α=90.000, β=91.124(4), γ=90.000°, V=3043.7(2) $Å^3$, Z=2, T=100.01(10) K, μ(CuKα)=2.215 $mm^{-1}$, Dcalc=1.247 g/$mm^3$, 11277 reflections measured (5.638≤2Θ≤103.66), 3312 unique ($R_{int}$=0.0668, $R_{sigma}$=0.0775) which were used in all calculations. The final $R_1$ was 0.0554 (I>2σ(I)) and $wR_2$ was 0.1523 (all data). CCDC Number: 2016357.

(c) Refinement Details. No special refinement necessary.

Figure 10:
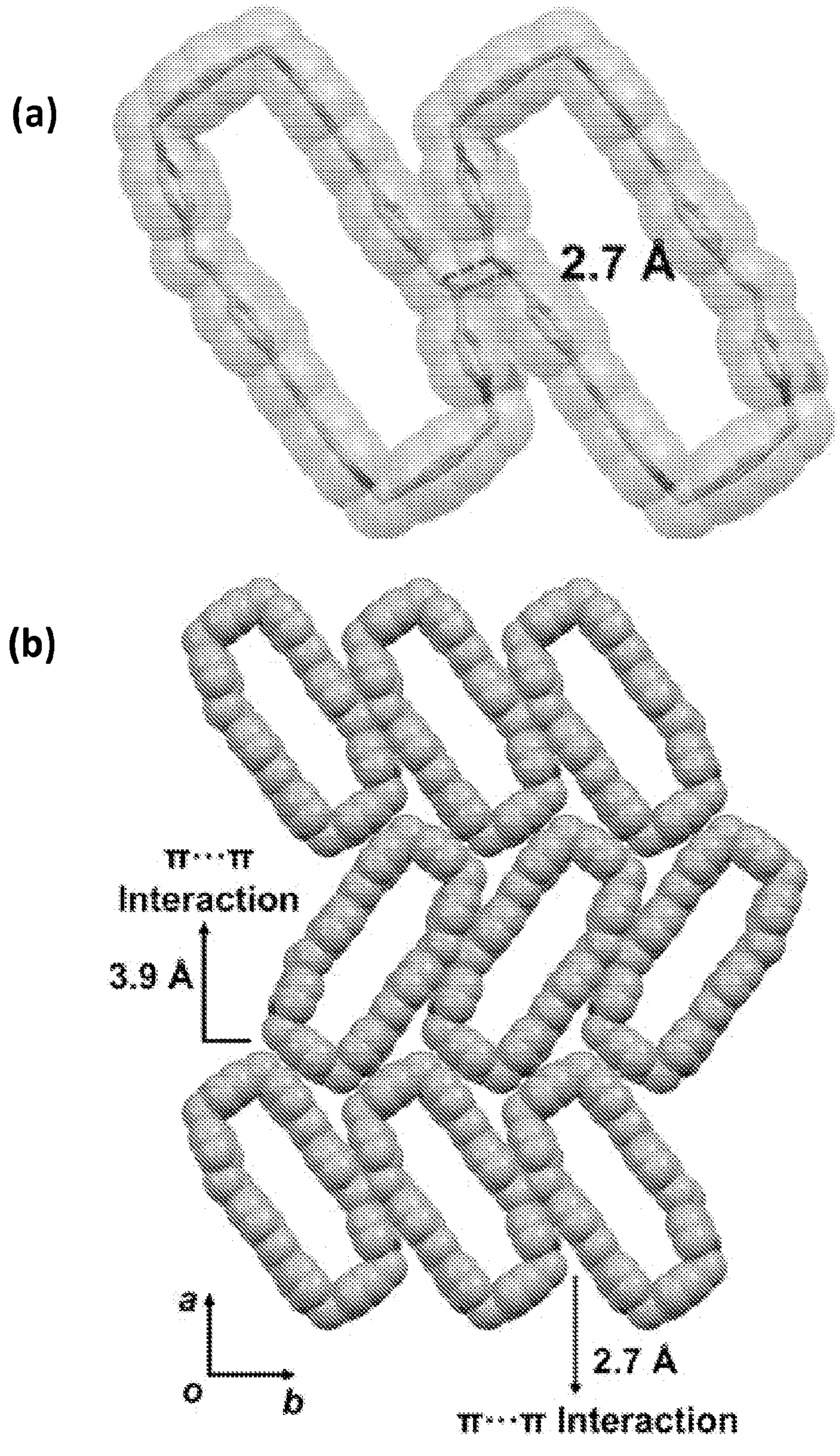
FIG. 10. Solid-state (super)structure of OPVEBox$^{4+}$ obtained from X-ray diffraction studies on single crystals of OPVEBox·4$PF_6$. (a) The solid-state superstructure showing the face-to-face stacking between the adjacent OPV$^{2+}$ units in adjacent OPVEBox$^{4+}$ molecules; (b) Solid-state superstructure of OPVEBox$^{4+}$ revealing a herringbone type of packing and two kinds of [π . . . π] interactions. The hydrogen atoms, counterions and solvent molecules are omitted for the sake of clarity.

(2) OPVEBox·$4PF_6$ (a) Method. OPVEBox·$4PF_6$ (1.4 mg, 1.0 μmol) was dissolved in MeCN (1.0 mL), and the resulting solution was passed through a 0.45-μm filter when added into two 1-mL tubes with volumes of 0.2, and 0.4 mL, respectively. The tubes were placed together in one 20-mL vial containing $iPr_2O$ (~3 mL) and the vial was capped. Slow vapor diffusion of $iPr_2O$ into the MeCN solution of OPVEBox·$4PF_6$ (1.0 mM) over the course of 3 days, yielded yellow single crystals of OPVEBox·$4PF_6$. A suitable crystal was mounted on a MITIGEN holder in Paratone oil on a Kappa Apex 2 diffractometer. The crystal was kept at 100.03 K during data collection. Using Olex22, the structure was solved with the SheXT$^3$ structure solution program using Intrinsic Phasing and refined with the XL$^4$ refinement package using Least Squares minimisation. The solid-state (super)structure of OPVEBox·$4PF_6$ is shown in FIG. 10.

(b) Crystal Parameters. $C_{56}H_{48}N_4\cdot(PF_6)_4$. Mr=1356.86. Yellow block (0.129×0.105×0.027 $mm^3$). Monoclinic, space group $P2_1/c$ (no. 14), a=19.621(8), b=12.649(4), c=14.500(5) Å, α=90.000, β=107.270(15), γ=90.000°, V=3437(2) $Å^3$, Z=2, T=100.03 K, μ(CuKα)=1.934 $mm^{-1}$, Dcalc=1.303 g/$mm^3$, 7256 reflections measured (4.716≤2Θ≤88.984), 2571 unique ($R_{int}$=0.1535, $R_{sigma}$=0.1765) which were used in all calculations. The final $R_1$ was 0.1395 (I>2σ(I)) and $wR_2$ was 0.4034 (all data). CCDC Number: 2016358.

(c) Refinement Details. Rigid bond restraints (esd 0.01) were imposed on the displacement parameters as well as restraints on similar amplitudes (esd 0.05) separated by less than 1.7 Å globally. Distance restraints were imposed on the disordered atoms.

(d) Solvent Treatment Details.

The solvent masking procedure as implemented in Olex2 was used to remove the electronic contribution of solvent molecules from the refinement. As the exact solvent content is not known, only the atoms used in the refinement model are reported in the formula here. Total solvent accessible volume/cell=693.0 Å3 [20.2%], Total electron count/cell=247.0.

Section F. Cyclic Voltammetry

Cyclic voltammetry (CV) was performed on a Gamry Multipurpose instrument (Reference 600) interfaced to a PC under $N_2$ atmosphere at 298 K. The CV experiments were recorded with a glassy carbon working electrode (0.071 $cm^2$, Cypress system), and the electrode surface was polished routinely with alumina-water slurry on a felt surface immediately before use. The counter electrode was a Pt coil, and the reference electrode was a Ag/AgCl electrode. CV Experiments were carried out in a 0.1 M solution of $TBAPF_6$ electrolyte in DMF at a 0.1 V/s scan rate, and are referenced to the reversible Fc/Fc$^+$ couple ([ferrocene]=0.5 mM). See FIG. 11.

Section G. Photophysical Characterization (1) UV-Vis Spectroscopic Analysis

See FIG. 12, FIG. 13, FIG. 14, FIG. 15, FIG. 16, and FIG. 17.

(2) Fluorescence Spectroscopic Analysis

Figure 21:
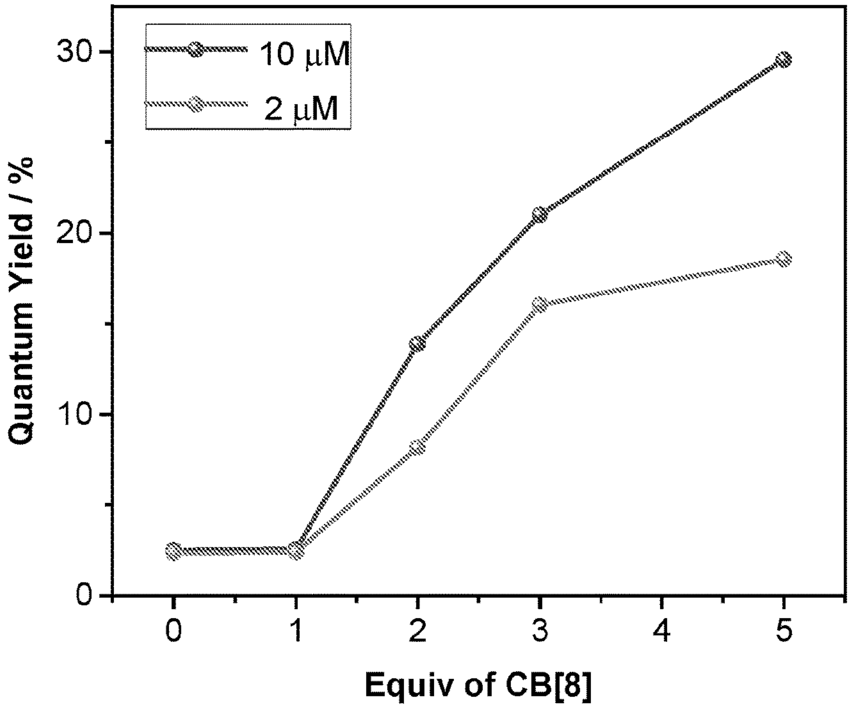
FIG. 21. The fluorescence quantum yields of $OPVEBox^{4+}$ ([$OPVEBox\cdot^{4+}$]=2 or 10 μM) at two different concentrations with adding different equiv of CB[8] in aqueous solutions FIG. 22. Fluorescent photographs of $OPVEBox^{4+}$, $OPVEBox^{4+}\subset$CB[8] and $OPVEBox^{4+}\subset$2CB[8] at the concentration of $10^{-5}$ and $10^{-4}$ M in aqueous solution, showing that both the binary and ternary ring-in-ring(s) complexes have highly fluorescent emission at relatively higher concentration (0.1 mM).

The excitation and emission spectra (FIGS. 18 and 19) were recorded for OPVEBox$^{4+}$. The red shift of emission spectra (FIG. 20) upon the addition of different equiv of CB[8] to the aqueous solution of OPVEBox·4Cl. The fluorescence quantum yield (FIG. 21 and Table 2) and lifetime (Table 3) changes of OPVEBox·4Cl upon the addition of different equiv of CB[8] in aqueous solutions. See also FIG. 22 and FIG. 23.

TABLE 2

The Fluorescence Quantum Yields of OPVEBox$^{4+}$ ($\lambda_{ex}$ = 392 nm) after Addition of 0-5 Equiv of CB[8] in Aqueous Solutions

| Concentration of OPVEBox$^{4+}$ | Sample | Quantum Yield/% |
|---|---|---|
| 2 μM | OPVEBox$^{4+}$ | 2.35 ± 0.004 |
| | 1 equiv CB[8] | 2.39 ± 0.008 |
| | 2 equiv CB[8] | 8.14 ± 0.020 |
| | 3 equiv CB[8] | 16.03 ± 0.051 |
| | 5 equiv CB[8] | 18.55 ± 0.058 |
| 10 μM | OPVEBox$^{4+}$ | 2.50 ± 0.002 |
| | 1 equiv CB[8] | 2.55 ± 0.002 |
| | 2 equiv CB[8] | 13.87 ± 0.013 |
| | 3 equiv CB[8] | 20.99 ± 0.021 |
| | 5 equiv CB[8] | 29.58 ± 0.032 |

TABLE 3

The Fluorescence Lifetimes of OPVEBox$^{4+}$ ($\lambda_{ex}$ = 374 nm, Laser) after Addition of 0-5 Equiv of CB[8] in Aqueous Solutions[a]

| Concentration | | Lifetime/ns (% contribution) | | |
|---|---|---|---|---|
| of OPVEBox$^{4+}$ | Sample | $\tau_1$ | $\tau_2$ | $\tau_{avg}$ |
| 2 μM | OPVEBox$^{4+}$ | 0.33 (100) | — | 0.33 |
| | 1 equiv CB[8] | 0.59 (85.94) | 8.11 (14.06) | 5.80 |
| | 2 equiv CB[8] | 0.67 (22.76) | 11.68 (77.24) | 11.50 |
| | 3 equiv CB[8] | 0.74 (11.95) | 11.98 (88.05) | 11.89 |
| | 5 equiv CB[8] | 0.75 (7.24) | 11.79 (92.76) | 11.74 |
| 10 μM | OPVEBox$^{4+}$ | 0.28 (100) | — | 0.28 |
| | 1 equiv CB[8] | 0.58 (86.53) | 7.87 (13.47) | 5.53 |
| | 2 equiv CB[8] | 0.81 (9.98) | 11.97 (90.02) | 11.89 |
| | 3 equiv CB[8] | 1.00 (5.74) | 11.99 (94.26) | 11.93 |
| | 5 equiv CB[8] | 1.10 (4.77) | 12.01 (95.23) | 11.96 |

[a]The fluorescence decay traces of OPVEBox$^{4+}$ with 0, 1, and 2-5 equiv of CB[8] were detected at 482, 533, 575 nm, respectively.

Section H. Isothermal Titration Calorimetry (ITC)

(1) Experiment Methods and Conditions

Figure 24:
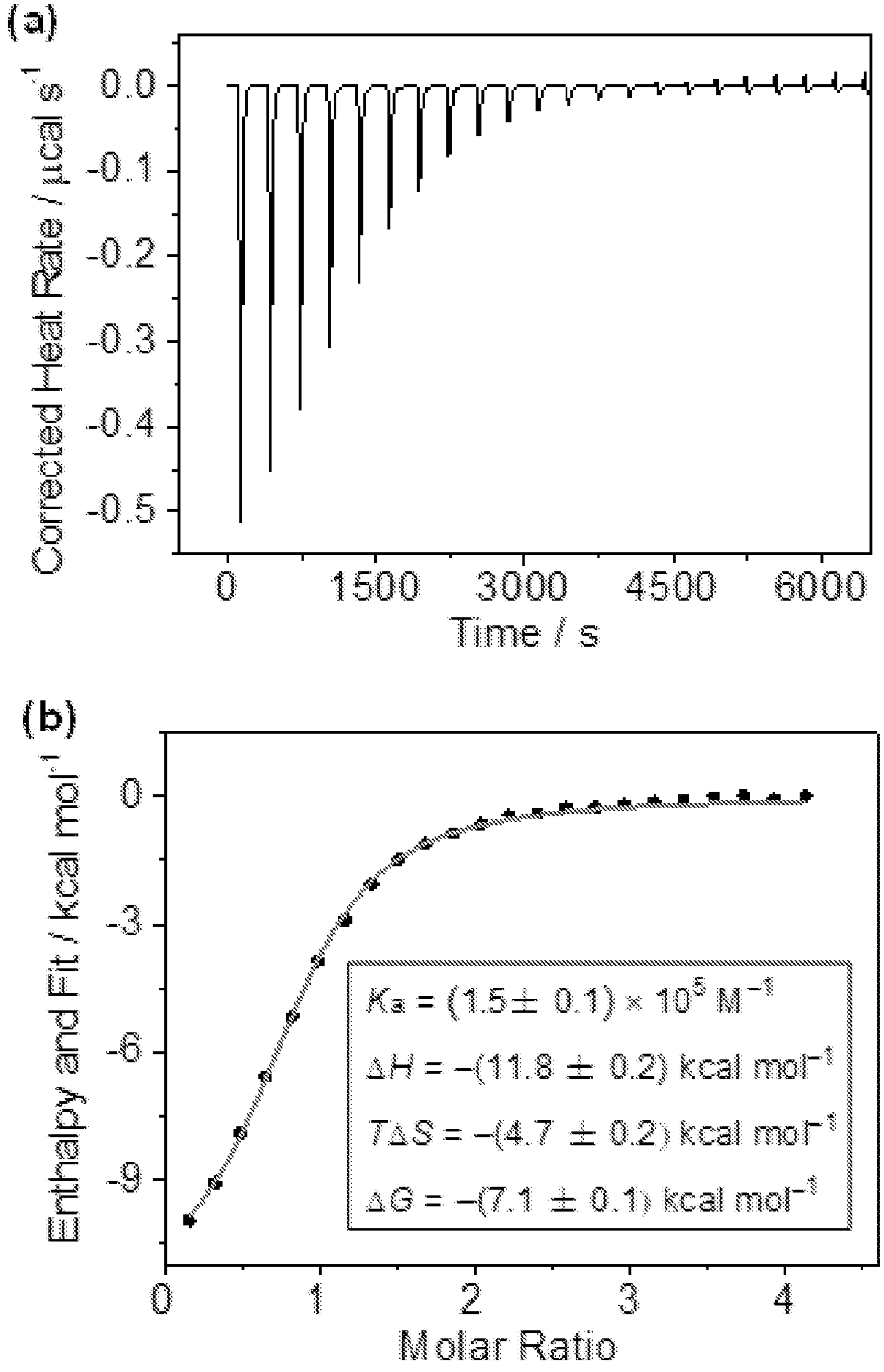
FIG. 24. Microcalorimetric titration data (a) and fitted curves (b) upon the addition of $OPVEBox^{4+}\subset$CB[8] complex (836 μM in syringe) into CB[8] (50 μM in cell) in aqueous NaCl (1 mM) solution at 298 K. The result suggested that the ternary $OPVEBox^{4+}\subset$2CB[8] complex was formed and the bonding constant K2 was found to be $1.5\times10^5$ $M^{-1}$.

All microcalorimetric titrations were performed in a thermostated TA Nano Isothermal Titration calorimeter at atmospheric pressure and 298 K. The samples were dissolved in an aqueous NaCl (1.0 mM) solution, in order to improve the solubility of CB[8], and the concentrations of sample were calibrated by UV-Vis absorption spectroscopy after filtered by a 0.45-filter. A solution of one reactant in a syringe was sequentially injected with stirring at 150 rpm into a solution of the other reactant in the sample cell with a constant volume of 185 μL. A representative titration curve is shown in FIG. 24, each titration of reactant into the sample cell gave an apparent reaction heat caused by the formation of the inclusion complex. The reaction heat decreases gradually until a balance was reached, whereupon only the dilution heat was measured. The net reaction heat was obtained by subtracting the dilution heat from the apparent reaction heat. The resulting data were analyzed with NanoAnalyze software using a 1:1 binding model to give the complex stability constant ($K_a$), standard molar reaction enthalpy ($\Delta H$), and standard deviations. Generally, the first point of the titration curve was disregarded, as there is some liquid mixing near the tip of the injection needle before ITC run. Each titration experiment was duplicated independently two times. All isotherm fittings were used to calculate the average $K_a$ and $\Delta H$, and the titration isotherm showed in FIG. 24 is one set of them. The standard free energy ($\Delta G$) and entropy changes ($\Delta S$) can be obtained according to the following equation:

$$\Delta G = -RT \ln K_a = \Delta H - T\Delta S$$

where R is the gas constant and T is the absolute temperature.

(2) Measurement of the Thermodynamic Parameters Between OPVEBox$^{4+}$ and CB[8]

Upon titrating CB[8] into the solution of OPVEBox$^{4+}$, a typical two-stage bonding process is uncovered. This process can be described using the following complexation equilibria:

First-stage:

$$\text{OPVEBox}^{4+} + \text{CB[8]} \overset{K_1}{\rightleftharpoons} \text{OPVEBox}^{4+}\subset\text{CB[8]}$$

Second-stage:

$$\text{OPVEBox}^{4+}\subset\text{CB[8]} + \text{CB[8]} \overset{K_2}{\rightleftharpoons} \text{OPVEBox}^{4+}\subset2\text{CB[8]}$$

Figure 25:
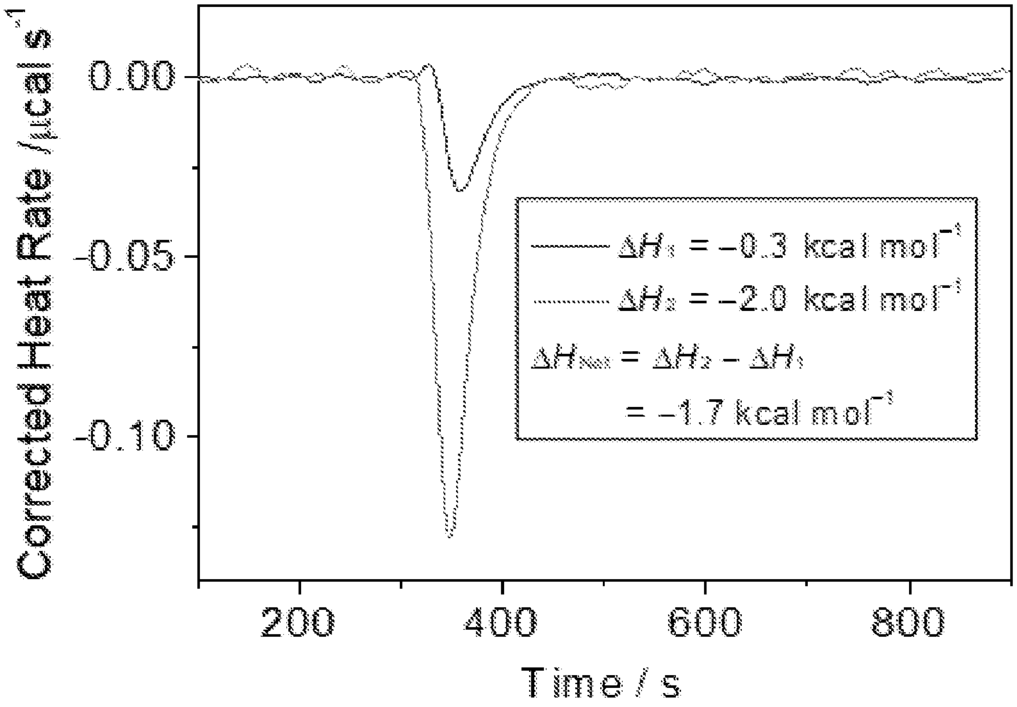
FIG. 25. Twice-independent single injection experiments, in which adding 1 equiv of $OPVEBox^{4+}$ (949 μM in syringe) into sample cell with (red line) or without (blue line) CB[8] (15 μM in cell) all at once in aqueous NaCl (1 mM) solution. The $\Delta H_1$, $\Delta H_2$ and $\Delta H_{Net}$ are represented as the dilution heat, apparent reaction heat and net reaction heat, respectively. The averaged binding enthalpy ($\Delta H_{Net}$) for the formation of $OPVEBox^{4+}\subset$CB[8] complex was estimated to be −2.0 kcal $mol^{-1}$.
Figure 25:
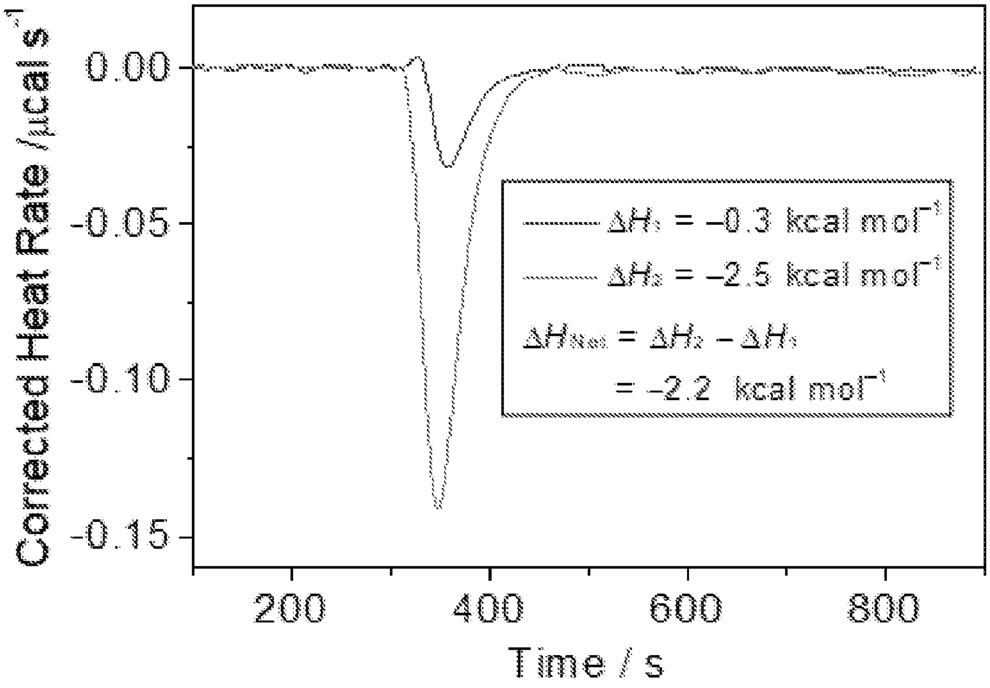
Figure 26:
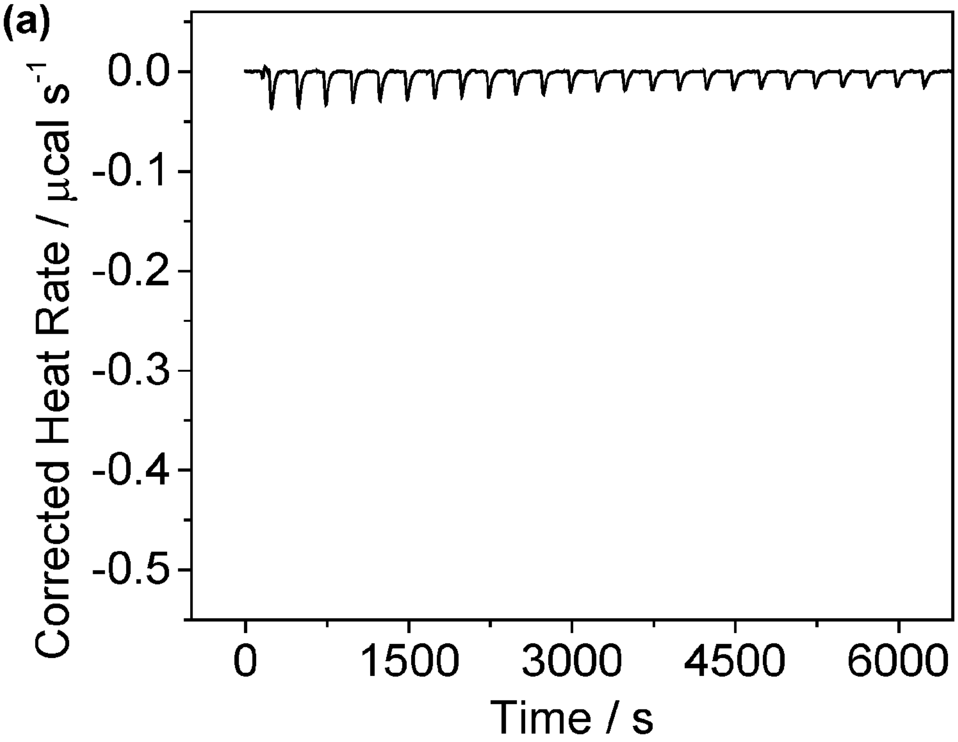
FIG. 26. Microcalorimetric titration data (a) and the change of enthalpy (b) upon the addition of $CBPQT^{4+}$ (1000 μM in syringe) into CB[8] (50 μM in cell) in aqueous NaCl (1 mM) solution at 298 K. There is no obvious enthalpy change, indicating that $CBPQT^{4+}$ does not bind inside the cavity of CB[8] to form a ring-in-ring complex.
Figure 26:
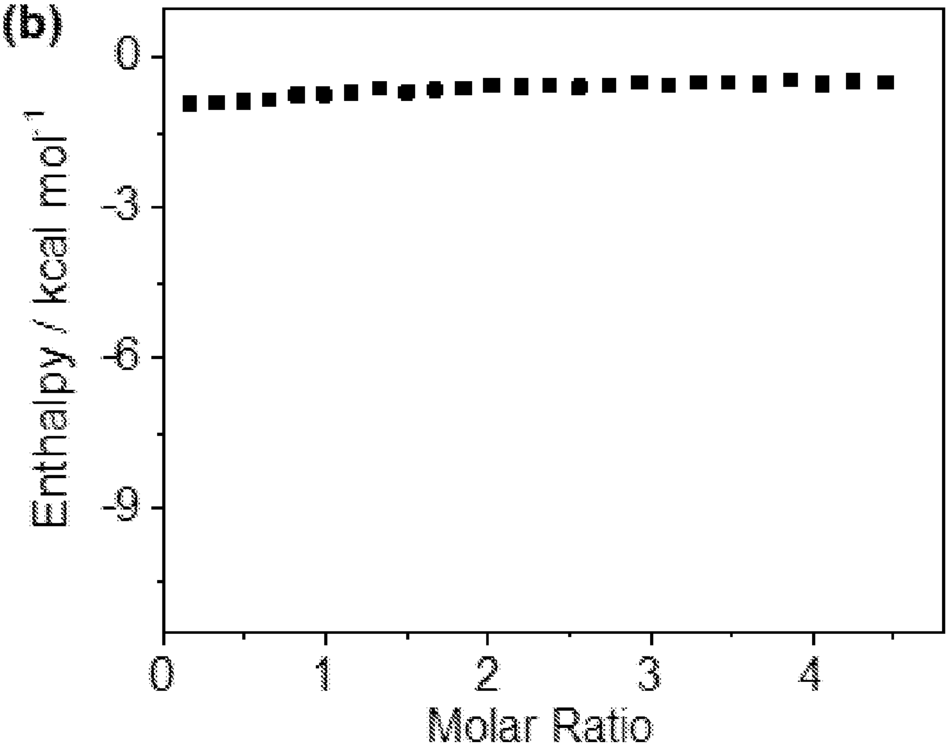
Figure 27:
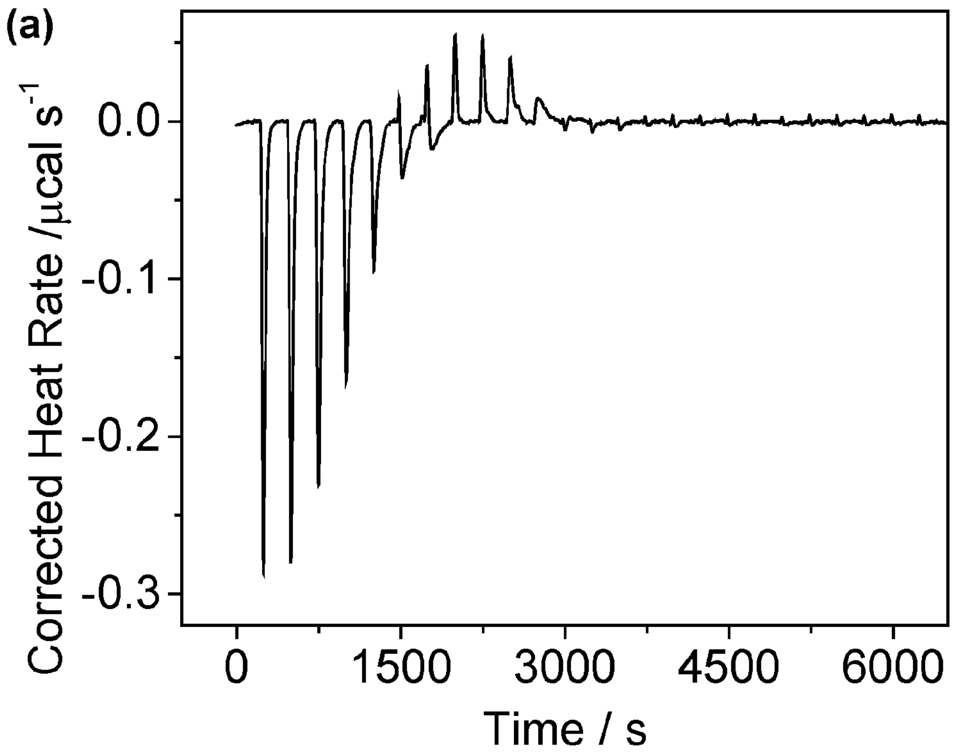
FIG. 27. Microcalorimetric titration data (a) and the change of enthalpy (b) upon the addition of $OPVEBox^{4+}$ (949 μM in syringe) into CB[8] (50 μM in cell) in aqueous NaCl (1 mM) solution at 298 K. The isotherm is too complex to fit with available programs.
Figure 27:
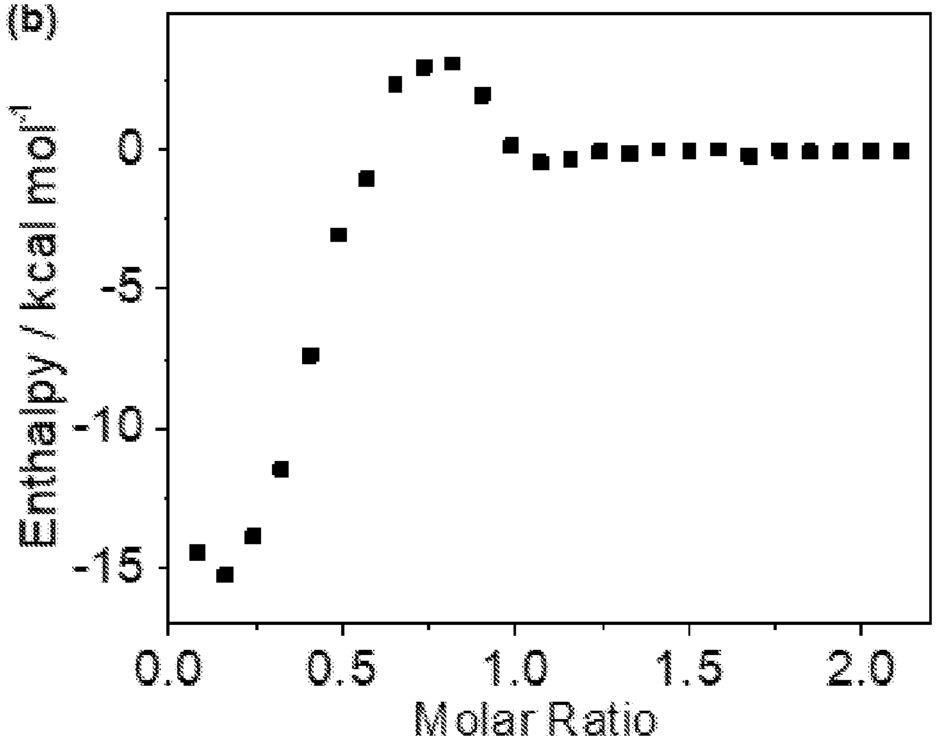
Figure 28:
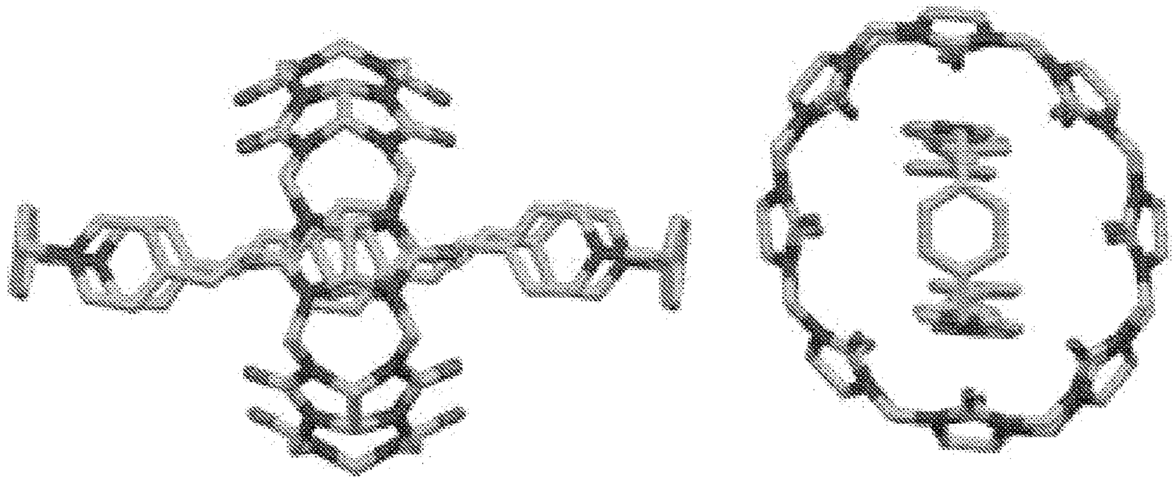
FIG. 28. Optimized superstructure of the binary $OPVEBox^{4+}\subset$CB[8] ring-in-ring complex obtained from DFT calculations. (a-b) Capped-stick representations of different views of the $OPVEBox^{4+}\subset$CB[8] complex.
Figure 29:
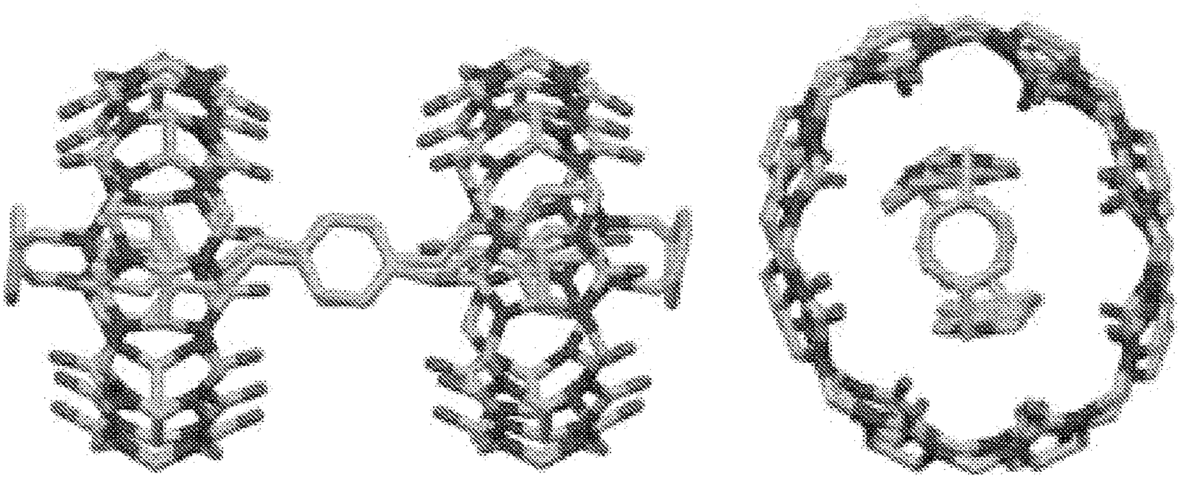
FIG. 29. Optimized superstructure of the ternary $OPVEBox^{4+}\subset$2CB[8] ring-in-rings complex obtained from DFT calculations. (a-b) Capped-stick representations of different views of the $OPVEBox^{4+}\subset$2CB[8] complex.

Hindering by the poor water solubility of CB[8], it is difficult to obtain simultaneously the $K_1$ and $K_2$ in a continuous calorimetric titration manner. The value for $K_1$ can be determined to be $5.8\times10^7$ $M^{-1}$ by analysis of the UV-Vis titration data. Such a high affinity between OPVEBox$^{4+}$ and CB[8] indicates that the OPVEBox$^{4+}$⊂CB[8] complex is formed quantitatively at high concentration. Hence, we tried using the twice-independent single injection experiments to estimate the binding enthalpy for the formation of OPVEBox$^{4+}$⊂CB[8]. The experiment data are shown in FIG. 25. On the other hand, when a solution of the OPVEBox$^{4+}$⊂CB[8] complex in a syringe was injected sequentially into a solution of CB[8] in the sample cell, the thermodynamic parameters of the second-stage recognition process were obtained. The experiment data are shown in FIG. 24. See also FIG. 26 and FIG. 27.

Section I. Density Functional Theory Calculations

Figure 30:
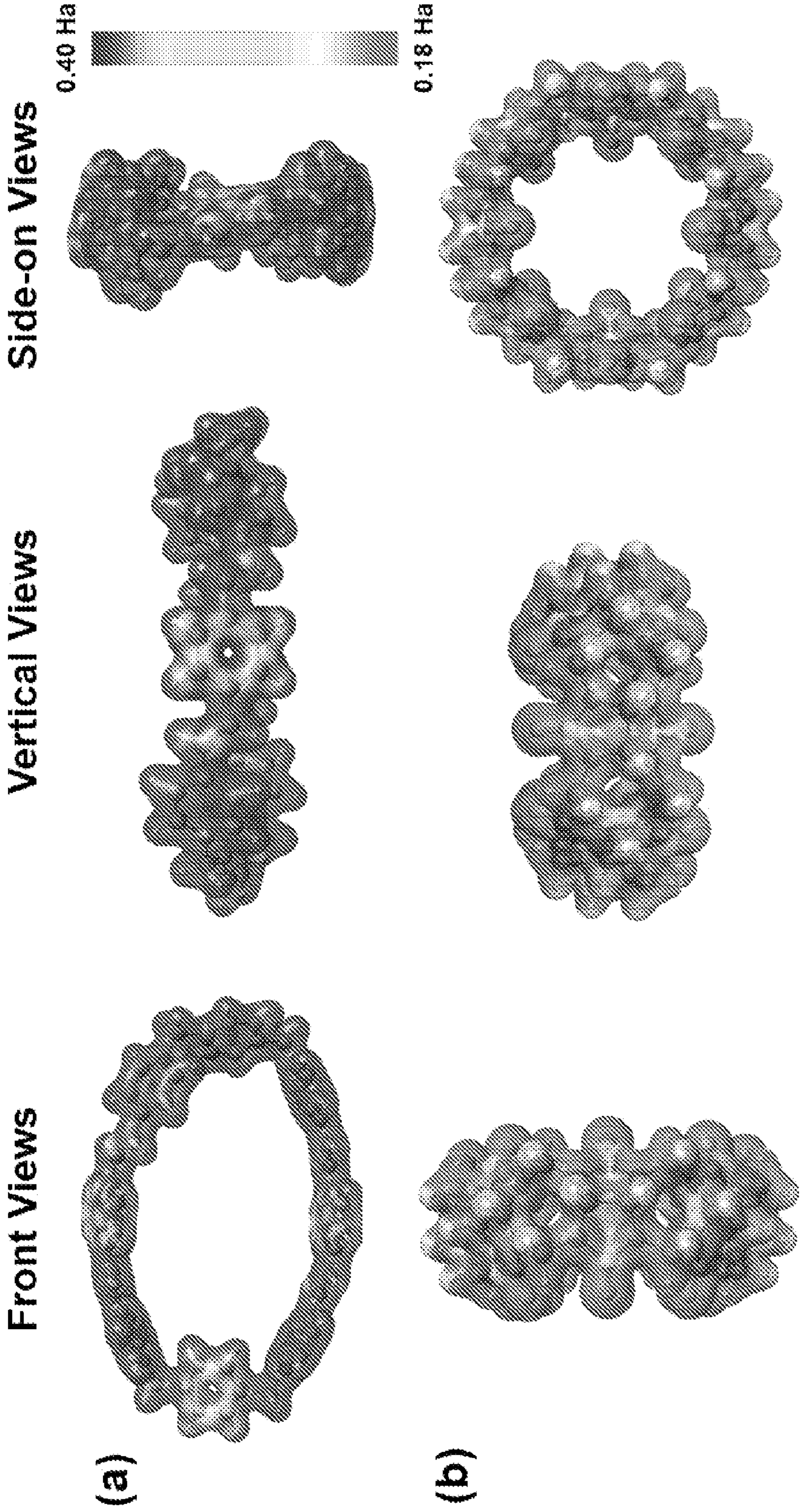
FIG. 30. Different views of electrostatic potential maps of (a) $OPVEBox^{4+}$ and (b) CB[8] obtained from DFT calculations. These maps demonstrate that the $OPVEBox^{4+}$ is electron poor, while the CB[8] is related electron negative. Red and blue colors in the maps represent negative and positive electrostatic potentials, respectively.
Figure 31:
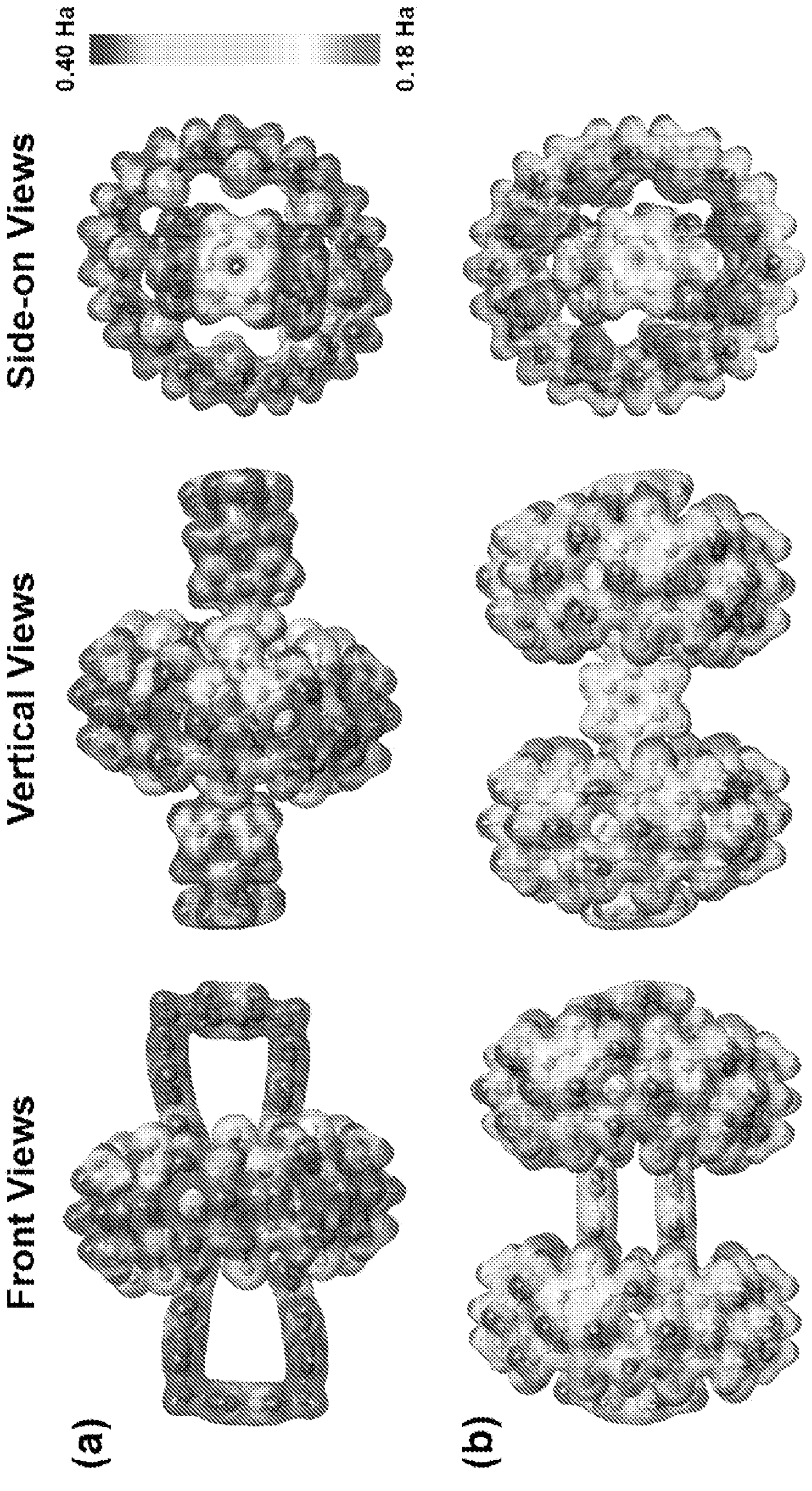
FIG. 31. Different views of electrostatic potential maps for (a) the binary $OPVEBox^{4+}\subset$CB[8] and (b) ternary $OPVEBox^{4+}\subset$2CB[8] ring-in-ring(s) complexes obtained from DFT calculations. The maps demonstrate that when combing with one or two CB[8] molecules, the $OPVEBox^{4+}\subset$CB[8] and $OPVEBox^{4+}\subset$2CB[8] complexes become more and more electron rich. Red and blue colors in the maps represent negative and positive electrostatic potentials, respectively.
Figure 32:
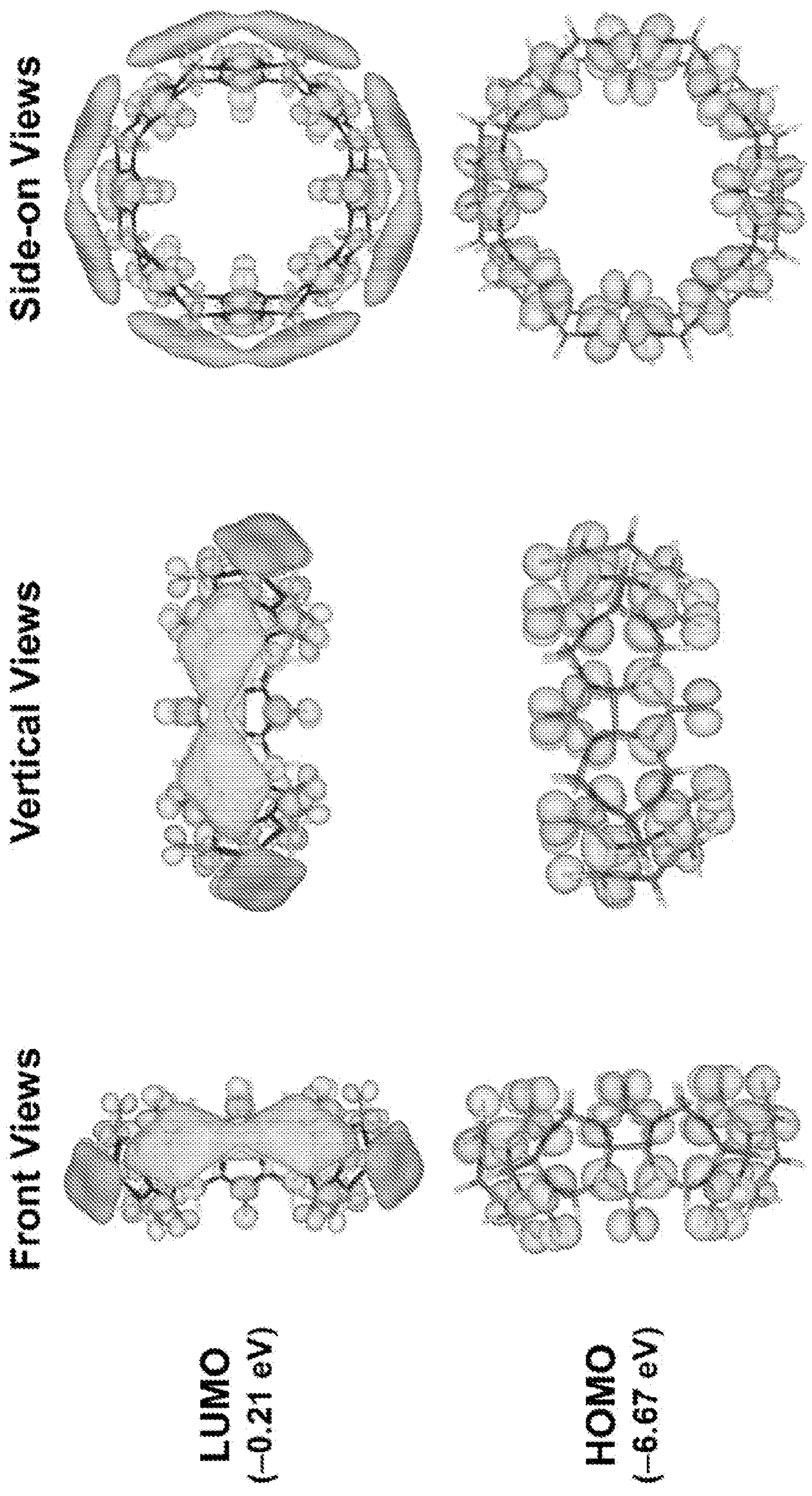
FIG. 32. Different views of frontier molecular orbitals for CB[8], which were calculated using the optimized geometry. The energy bandgap was calculated to be 6.46 eV.
Figure 33:
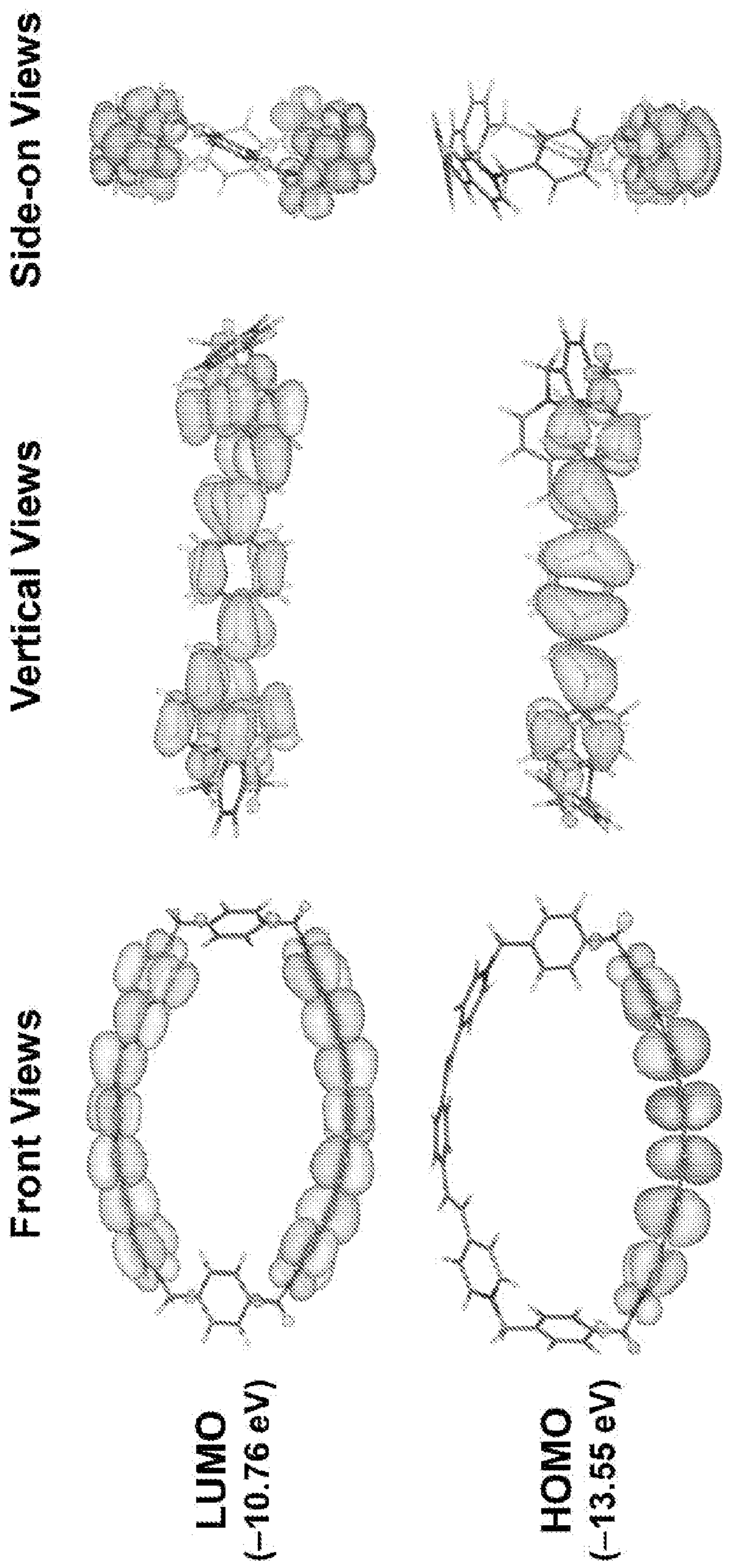
FIG. 33. Different views of frontier molecular orbitals for $OPVEBox^{4+}$, which were calculated using the optimized geometry. The energy bandgap was calculated to be 2.79 eV. There is slight symmetry breaking, which results in the HOMO being localized on one side of the cyclophane.
Figure 34:
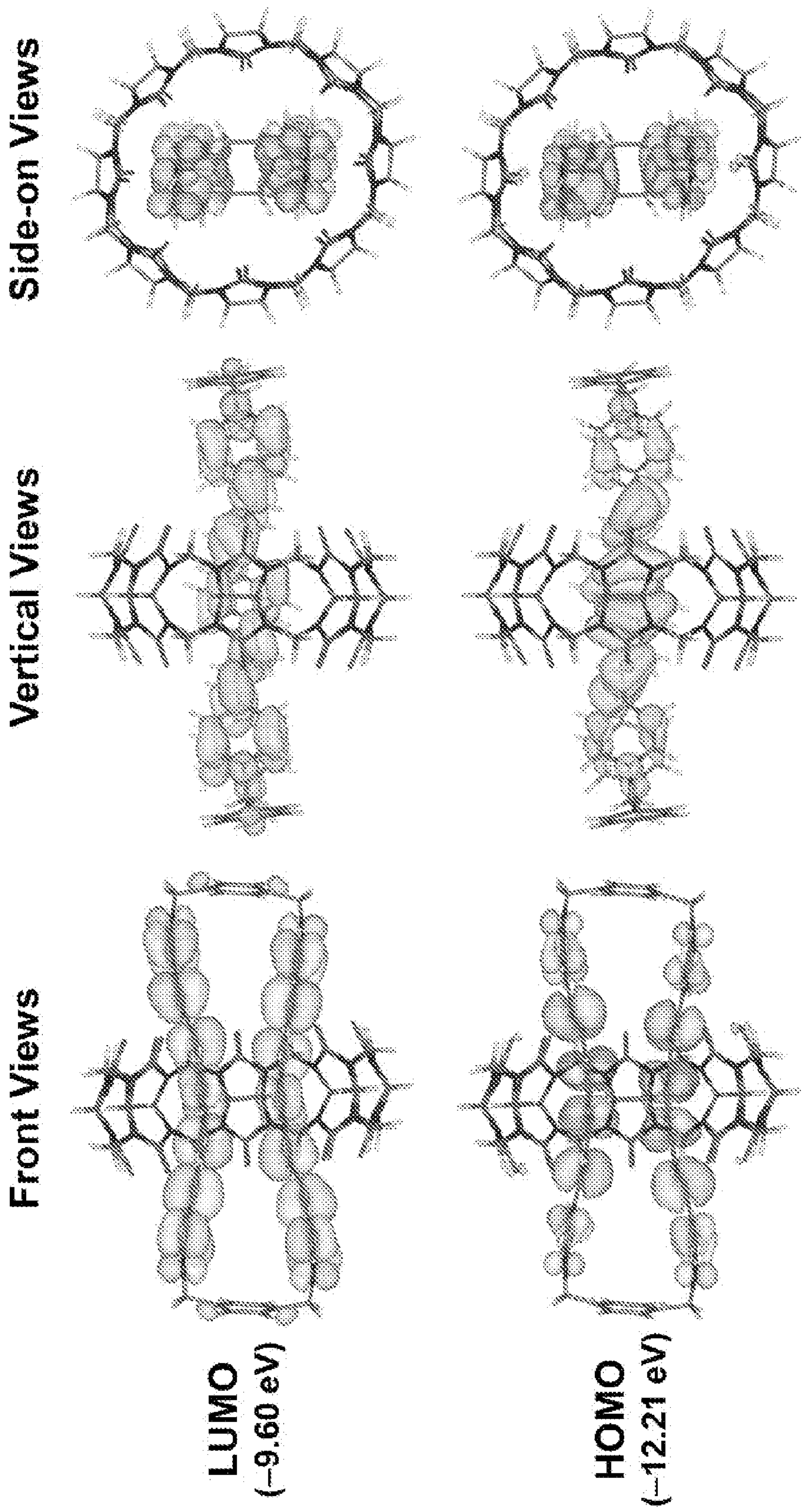
FIG. 34. Different views of frontier molecular orbitals for binary $OPVEBox^{4+}\subset$CB[8] ring-in-ring complex, which were calculated using the optimized geometry. The energy bandgap was calculated to be 2.61 eV.
Figure 35:
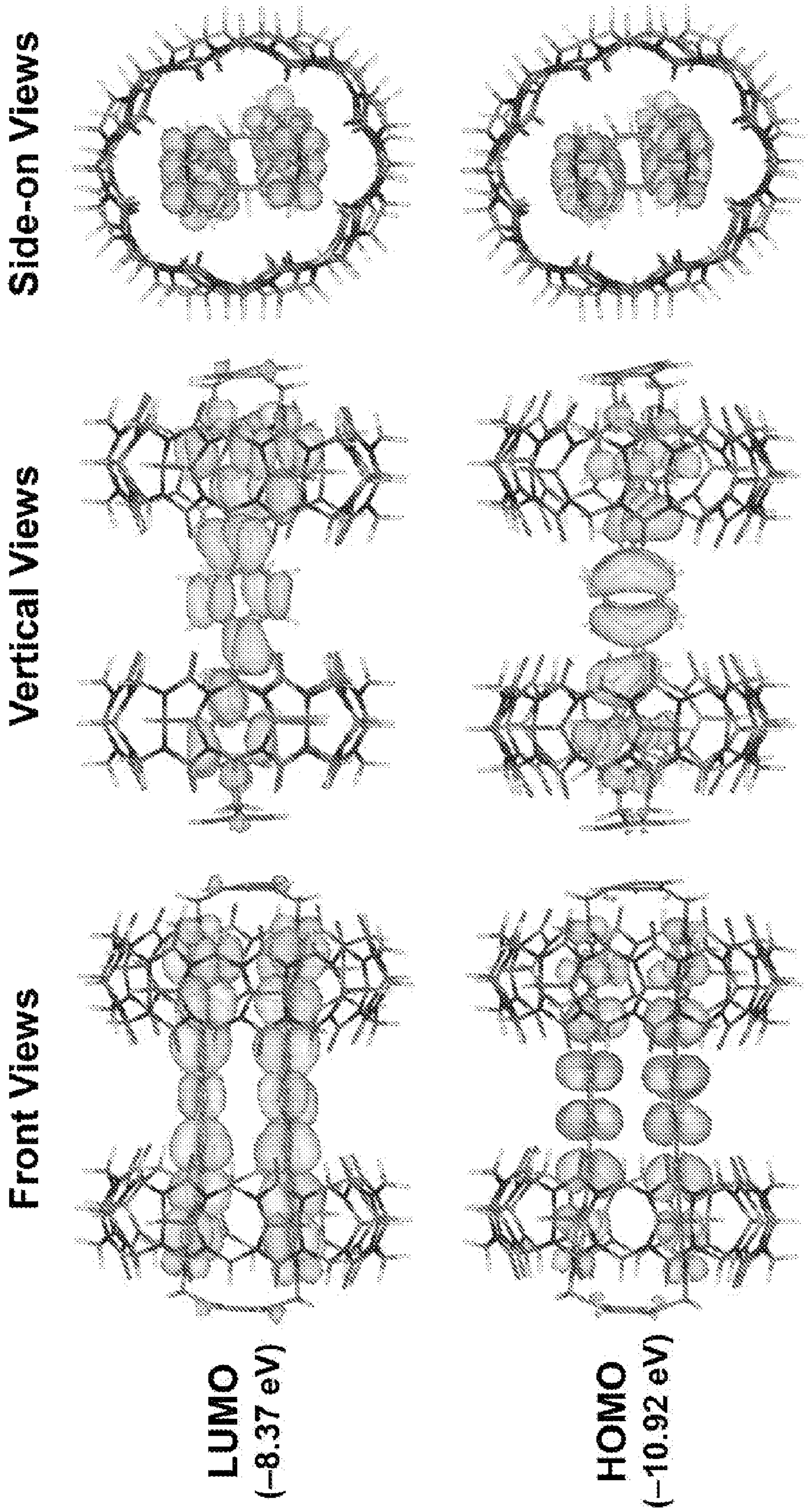
FIG. 35. Different views of frontier molecular orbitals for ternary $OPVEBox^{4+}\subset$2CB[8] ring-in-rings complex, which were calculated using the optimized geometry. The energy bandgap was calculated to be 2.55 eV.

In order to gain a better understanding of the geometrical superstructure of the binary OPVEBox$^{4+}$⊂CB[8] and ternary OPVEBox$^{4+}$⊂2CB[8] ring-in-ring(s) complexes, as well as the electronic properties and frontier molecular orbitals for all the structures, DFT calculations have been carried out based on the crystal structures of OPVEBox$^{4+}$ and CB[8]. FIGS. 30 and 31 show the DFT-optimized structures of the OPVEBox$^{4+}$⊂CB[8] and OPVEBox$^{4+}$⊂2CB[8] complexes, respectively. FIGS. 32 and 33 show the electrostatic potential maps of CB[8] and OPVEBox$^{4+}$, as well as the OPVEBox$^{4+}$⊂CB[8] and OPVEBox$^{4+}$⊂2CB[8] complexes, respectively. FIGS. 34-37 show the frontier molecular orbitals of CB[8], OPVEBox$^{4+}$, OPVEBox$^{4+}$⊂CB[8] and OPVEBox$^{4+}$⊂2CB[8], respectively. Tables 4 and 5 summarizes the energy levels for CB[8], OPVEBox$^{4+}$, and their complexes in vacuum and water, respectively. Tables 6 and 7 summarizes the strain energy for the central OPVEBox$^{4+}$ in ring-in-ring(s) complexes in vacuum and water, respectively.

The xyz coordinates from the X-ray single crystals of the OPVEBox$^{4+}$ and CB[8] were used as the starting geometries for their individual optimizations in vacuum. In order to construct the complexes, OPVEBox$^{4+}$ was carefully manipulated in the molecular editor Avogadro program[5] (version 1.1.1) and threaded through the CB[8] structure until half of each loop was sitting on either side of the CB[8] molecule; this geometry formed the basis of OPVEBox$^{4+}$⊂CB[8] complex. This superstructure was initially energy minimized at the molecular mechanics (MM) level with the universal force field[6,7] (UFF) in Avogadro. In order to form OPVEBox$^{4+}$⊂2CB[8] complex, one CB[8] molecule was moved along to one end of OPVEBox$^{4+}$ and another CB[8]

was added to the other end. This complex was also energy minimized at the same level as $OPVEBox^{4+} \subset CB[8]$. All four (super)structures, i.e., CB[8], $OPVEBox^{4+}$, $OPVEBox^{4+} \subset CB[8]$, $OPVEBox^{4+} \subset 2CB[8]$, were optimized subsequently with density functional theory (DFT) in the Orca program[8] (version 4.1.2) using the hybrid generalized gradient approximation (GGA) Becke three-parameter Lee-Yang-Parr[9] (B3LYP) functional, and the Ahlrich's double zeta basis set with a polarization function[10] Def2-SVP. In order to speed up the DFT optimizations, the Coulomb integral and numerical chain-of-sphere integration for the HF exchange[11,12] (RIJCOSX) method was applied with the Def2/J auxiliary basis[13,14] (AuxJ). The Frontier Molecular Orbitals (FMO) were visualized in ChemCraft (version b574b). The electrostatic potential maps were computed with B3LYP and the Slater-type basis see[15] DZP in the Amsterdam Density Functional program[16] (version 2018.104) for CB[8], $OPVEBox^{4+}$ and $OPVEBox^{4+} \subset CB[8]$ complex, while that of $OPVEBox^{4+} \subset 2CB[8]$ complex was computed at the B3LYP/SZ level on account of its size, as any larger basis was computationally intractable. Frozen cores were used as implemented in ADF (which for C, O and N relates to the is core being frozen) to reduce the computational cost. The optimized structures in vacuum were re-optimized at the same theoretical level with the Solvation Model based on Density[17] (SMD) variant of the Conductor-like Polarizable Continuum Model[18] (CPCM) in a water continuum, in the Orca program. These CPCM structures were found to have several stationary points that equilibrated and thus no single minimum was found; except for slight xyz displacements the overall structures in a water continuum remained chemically identical to their vacuum counterparts. These can therefore be considered as semi-optimized but serve the purpose of analyzing the FMO energies in experimental conditions.

TABLE 4

The Calculated Energy Levels of the Frontier Molecular Orbitals in Vacuum

| Energy/eV | CB[8] | $OPVEBox^{4+}$ | $OPVEBox^{4+} \subset CB[8]$ | $OPVEBox^{4+} \subset 2CB[8]$ |
|---|---|---|---|---|
| $\Psi_{LUMO}$ | −0.21 | −10.76 | −9.60 | −8.37 |
| $\Psi_{HOMO}$ | −6.67 | −13.55 | −12.21 | −10.92 |
| $\Delta E_{HOMO\text{-}LUMO}$ | 6.46 | 2.79 | 2.61 | 2.55 |

TABLE 5

The Calculated Energy Levels of the Frontier Molecular Orbitals in Water

| Energy/eV | CB[8] | $OPVEBox^{4+}$ | $OPVEBox^{4+} \subset CB[8]$ | $OPVEBox^{4+} \subset 2CB[8]$ |
|---|---|---|---|---|
| $\Psi_{LUMO}$ | 0.54 | −3.21 | −3.10 | −3.04 |
| $\Psi_{HOMO}$ | −6.82 | −6.18 | −5.81 | −5.64 |
| $\Delta E_{HOMO\text{-}LUMO}$ | 7.36 | 2.97 | 2.71 | 2.60 |

(4) Strain Energy Calculations

TABLE 6

The Calculated Strain Energy for the Central $OPVEBox^{4+}$ in Ring-in-Ring(s) Complexes in Vacuum

| Strain Energy | $OPVEBox^{4+}$ | $OPVEBox^{4+} \subset CB[8]$ | $OPVEBox^{4+} \subset 2CB[8]$ |
|---|---|---|---|
| E/ha | −2377.4934 | −2377.4478 | −2377.4251 |
| $\Delta E$/kal $mol^{-1}$ | — | 28.59 | 42.85 |

TABLE 7

The Calculated Strain Energy for the Central $OPVEBox^{4+}$ in Ring-in-Ring(s) Complexes in Water

| Strain Energy | $OPVEBox^{4+}$ | $OPVEBox^{4+} \subset CB[8]$ | $OPVEBox^{4+} \subset 2CB[8]$ |
|---|---|---|---|
| E/ha | −2378.3322 | −2378.3354 | −2378.3250 |
| $\Delta E$/kal $mol^{-1}$ | — | −2.01 | 4.52 |

Section J. References (1) Wu, H.; Chen, Y.; Zhang, L.; Anamimoghadam, O.; Shen, D.; Liu, Z.; Cai, K.; Pezzato, C.; Stern, C. L.; Liu, Y.; Stoddart, J. F. A Dynamic Tetracationic Macrocycle Exhibiting Photoswitchable Molecular Encapsulation. *J. Am. Chem. Soc.* 2019, 141, 1280-1289.

(2) Dolomanov, O. V.; Bourhis, L. J.; Gildea, R. J.; Howard, J. A. K.; Puschmann, H. OLEX2: A Complete Structure Solution, Refinement and Analysis Program. *J. Appl. Cryst.* 2009, 42, 339-341.

(3) Sheldrick, G. M. SHELXT—Integrated Space-Group and Crystal-Structure Determination. *Acta. Cryst.* 2015, A71, 3-8.

(4) Sheldrick, G. M. A Short History of SHELX. *Acta. Cryst.* 2008, A64, 112-122.

(5) Hanwell, M. D.; Curtis, D. E.; Lonie, D. C.; Vandermeersch, T.; Zurek, E.; Hutchison, G. R. Avogadro: An Advanced Semantic Chemical Editor, Visualization, and Analysis Platform. *J. Cheminf.* 2012, 4, 17.

(6) Rappe, A. K.; Casewit, C. J.; Colwell, K. S.; Goddard, W. A.; Skiff, W. M. UFF, A Full Periodic Table Force Field for Molecular Mechanics and Molecular Dynamics Simulations. *J. Am. Chem. Soc.* 1992, 114, 10024-10035.

(7) Rappe, A. K.; Colwell, K. S.; Casewit, C. J. Application of a Universal Force Field to Metal Complexes. *Inorg. Chem.* 1993, 32, 3438-3450.

(8) Neese, F. The ORCA Program System. *Wiley Interdiscip. Rev.: Comput. Mol. Sci.,* 2012, 2, 73-78.

(9) Becke, A. D. Density Functional Thermochemistry. III. The Role of Exact Exchange. *J. Chem. Phys.* 1993, 98, 5648-5652.

(10) Weigend, F.; Ahlrichs, R. Balanced Basis Sets of Split Valence, Triple Zeta Valence and Quadruple Zeta Valence Quality for H to Rn: Design and Assessment of Accuracy. *Phys. Chem. Chem. Phys.* 2005, 7, 3297-3305.

(11) Neese, F. An Improvement of the Resolution of the Identity Approximation for the Calculation of the Coulomb Matrix. *J. Comp. Chem.,* 2003, 24, 1740-1747.
(12) Izsak, R.; Neese, F. An Overlap Fitted Chain of Spheres Exchange Method, *J. Chem. Phys.,* 2011, 135, 144105.
(13) Weigend, F. Accurate Coulomb-Fitting Basis Sets for H to Rn. *Phys. Chem. Chem. Phys.* 2006, 8, 1057-1065.
(14) Stoychev, G. L.; Auer, A. A.; Neese, F. Automatic Generation of Auxiliary Basis Sets. *J. Theo. Comp. Chem.* 2017, 13, 554-562.
(15) Van Lenthe, E.; Baerends, E. J. Optimized Slater-Type Basis Sets for the Elements 1-118. *J. Comput. Chem.* 2003, 24, 1142-1156.
(16) to Velde, G.; Bickelhaupt, F. M.; Baerends, E. J.; Fonseca Guerra, C.; van Gisbergen, S. J. A.; Snijders, J. G.; Ziegler, T. Chemistry with ADF. *J. Comput. Chem.* 2001, 22, 931-967.
(17) Marenich, A. V.; Cramer, C. J.; Truhlar, D. G. Universal Solvation Model Based on Solute Electron Density and on a Continuum Model of the Solvent Defined by the Bulk Dielectric Constant and Atomic Surface Tensions. *J. Phys. Chem. B,* 2009, 113, 6378-6396.
(18) Barone, V.; Cossi, M. Quantum Calculation of Molecular Energies and Energy Gradients in Solution by a Conductor Solvent Model. *J. Phys. Chem. A,* 1998, 102, 1995-2001.

We claim:

1. A ring-in-ring photoluminescent complex comprising a host cyclophane and a guest cyclophane threaded through the host cyclophane, wherein the host cyclophane is a cucurbit[n]uril, wherein the complex is a 1:1 host-guest complex, a 2:1 host-guest complex, or a combination thereof and wherein the guest cyclophane has a first photoluminescent emission maxima, the 1:1 host-guest complex has a second photoluminescent emission maxima, the 2:1 host-guest complex with the host cyclophane has a third photoluminescent emission maxima, and each of the first, second, and third photoluminescent emission maxima are different.

2. The complex of claim 1, wherein the complex is the 1:1 host-guest complex.

3. The complex of claim 1, wherein the complex is the 2:1 host-guest complex.

4. The complex of claim 1, wherein the host cyclophane is cucurbit[8]uril.

5. The complex of claim 1, wherein the guest cyclophane is

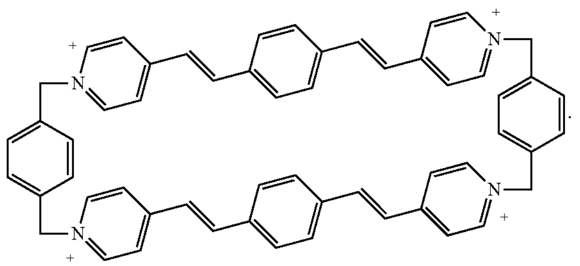

6. The complex of claim 1, wherein the guest cyclophane is the tetracationic cyclophane.

7. The complex of claim 6, wherein the host cyclophane is cucurbit[8]uril and the guest cyclophane is

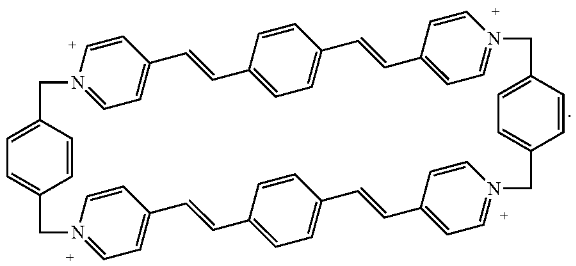

8. A photoluminescent composition comprising the host cyclophane and the guest cyclophane, wherein the composition is capable of forming the ring-in-ring photoluminescent complex according to claim 1 and wherein molar ratio of the host cyclophane to the guest cyclophane in the composition determines the frequency of emitted radiation after irradiation.

9. The composition of claim 8, wherein the composition comprises two or more of the 1:1 host-guest complex, the 2:1 host-guest complex, an uncomplexed host cyclophane, and an uncomplexed guest cyclophane.

10. The composition of claim 9, wherein the composition comprises the 1:1 host-guest complex and the 2:1 host-guest complex.

11. The composition of claim 8 further comprising a competitive complexation agent.

12. The composition of claim 11, wherein the competitive complexation agent is a competitive guest.

13. The composition of claim 11, wherein the competitive complexation agent is a competitive host.

14. A method of inducing photoluminescence, the method comprising irradiating the ring-in-ring photoluminescent complex according to claim 1.

15. A method of inducing photoluminescence, the method comprising irradiating the composition according to claim 8.

16. A method for tuning photoluminescence, the method comprising providing a host cyclophane and a guest cyclophane, contacting the guest cyclophane with the host cyclophane thereby forming the ring-in-ring photoluminescent complex according to claim 1, and irradiating the complex, wherein a molar ratio of host cyclophane to the guest cyclophane determines the frequency of emitted radiation.

17. The method of claim 16 further comprising providing a competitive complexation agent.

18. The method of claim 17, wherein the competitive complexation agent is a competitive guest.

19. The method of claim 17, wherein the competitive complexation agent is a competitive host.

* * * * *